(12) United States Patent
Soliman et al.

(10) Patent No.: US 9,616,109 B2
(45) Date of Patent: Apr. 11, 2017

(54) INSULIN VITAMIN D CONJUGATES

(71) Applicant: Extend Biosciences, Inc., Cambridge, MA (US)

(72) Inventors: Tarik Soliman, Cambridge, MA (US); Laura M. Hales, Cambridge, MA (US); Daniel B. Hall, Easton, MA (US); Howard Sard, Arlington, MA (US); Vishnumurthy Hegde, Chelmsford, MA (US)

(73) Assignee: Extend Biosciences, Inc., Newton, MA (US)

( * ) Notice: Subject to any disclaimer, the term of this patent is extended or adjusted under 35 U.S.C. 154(b) by 0 days.

(21) Appl. No.: 14/919,572

(22) Filed: Oct. 21, 2015

(65) Prior Publication Data

US 2016/0114001 A1 Apr. 28, 2016

Related U.S. Application Data

(60) Provisional application No. 62/067,398, filed on Oct. 22, 2014, provisional application No. 62/203,385, filed on Aug. 10, 2015.

(51) Int. Cl.
*A61K 38/28* (2006.01)
*A61K 9/00* (2006.01)
*A61K 47/48* (2006.01)
*C07K 14/62* (2006.01)

(52) U.S. Cl.
CPC ............ *A61K 38/28* (2013.01); *A61K 9/0019* (2013.01); *A61K 47/48023* (2013.01); *A61K 47/48107* (2013.01); *A61K 47/48215* (2013.01); *A61K 47/48246* (2013.01); *C07K 14/62* (2013.01)

(58) Field of Classification Search
None
See application file for complete search history.

(56) References Cited

U.S. PATENT DOCUMENTS

| | | | |
|---|---|---|---|
| 4,179,337 A | 12/1979 | Davis et al. | |
| 4,292,250 A | 9/1981 | DeLuca et al. | |
| 4,410,515 A | 10/1983 | Holick et al. | |
| 4,456,553 A | 6/1984 | Oshida et al. | |
| 4,675,189 A | 6/1987 | Kent et al. | |
| 4,816,567 A | 3/1989 | Cabilly et al. | |
| 5,108,921 A | 4/1992 | Low et al. | |
| 5,116,964 A | 5/1992 | Capon et al. | |
| 5,122,614 A | 6/1992 | Zalipsky | |
| 5,214,170 A | 5/1993 | Tanabe et al. | |
| 5,232,836 A | 8/1993 | Bouillon et al. | |
| 5,416,016 A | 5/1995 | Low et al. | |
| 5,428,023 A | 6/1995 | Russell-Jones et al. | |
| 5,447,851 A | 9/1995 | Beutler et al. | |
| 5,545,806 A | 8/1996 | Lonberg et al. | |
| 5,545,807 A | 8/1996 | Surani et al. | |
| 5,550,111 A | 8/1996 | Suhadolnik et al. | |
| 5,569,825 A | 10/1996 | Lonberg et al. | |
| 5,574,018 A | 11/1996 | Habberfield et al. | |
| 5,605,690 A | 2/1997 | Jacobs et al. | |
| 5,625,126 A | 4/1997 | Lonberg et al. | |
| 5,629,384 A | 5/1997 | Veronese et al. | |
| 5,633,425 A | 5/1997 | Lonberg et al. | |
| 5,661,016 A | 8/1997 | Lonberg et al. | |
| 5,688,488 A | 11/1997 | Low et al. | |
| 5,691,328 A | 11/1997 | Peterson et al. | |
| 5,714,142 A | 2/1998 | Blaney et al. | |
| 5,739,277 A | 4/1998 | Presta et al. | |
| 5,767,254 A | 6/1998 | Polt | |
| 5,869,466 A | 2/1999 | Russell-Jones et al. | |
| 5,876,969 A | 3/1999 | Fleer et al. | |
| 5,919,452 A | 7/1999 | Le et al. | |
| 5,932,462 A | 8/1999 | Harris et al. | |
| 6,093,701 A | 7/2000 | Wolff et al. | |
| 6,342,225 B1 | 1/2002 | Jones et al. | |
| 6,395,492 B1 | 5/2002 | Manoharan et al. | |
| 6,455,714 B1 | 9/2002 | Holick et al. | |
| 6,660,843 B1 | 12/2003 | Feige et al. | |
| 6,713,280 B1 | 3/2004 | Huang et al. | |
| 6,787,660 B1 | 9/2004 | Armbruster et al. | |
| 6,858,227 B1 | 2/2005 | Lal et al. | |
| 6,887,470 B1 | 5/2005 | Bridon et al. | |
| 6,929,797 B2 | 8/2005 | Mazess et al. | |
| 7,045,318 B2 | 5/2006 | Ballance | |
| 7,141,547 B2 | 11/2006 | Rosen et al. | |
| 7,176,278 B2 | 2/2007 | Prior | |

(Continued)

FOREIGN PATENT DOCUMENTS

EP 0312360 B1 6/1992
EP 0486525 B1 6/1994

(Continued)

OTHER PUBLICATIONS

American Peptide Company, "The case for PEG conjugation", 2008.
Drug Lib.com, "Vitamin D2", copyright, 2006-2015.
Kojima et al. "Ghrelin: From Gene to Physiological Function", 2010, p. 185-205.
Akamizu, et al. Pharmacokinetics, safety, and endocrine and appetite effects of ghrelin administration in young healthy subjects. European Journal of Endocrinology ,150:447-455 (2004).
Bertrand, et al. Apelin and Energy Metabolism. Frontiers in Physiology 6:115 (2015).
Castan-Laurell, et al. Apelin, Diabetes, and Obesity. Endocrine 40(1):1-9 (2011).
Fishwild et al. High-Avidity Human IgGk Monoclonal Antibodies from a Novel Strain of Minilocus Transgenic Mice. Nature Biotechnology 14:845-851 (1996).

(Continued)

*Primary Examiner* — James H Alstrum Acevedo
*Assistant Examiner* — Tara Martinez
(74) *Attorney, Agent, or Firm* — Kaplan IP Law, P.C.; Jonathan M. Kaplan

(57) ABSTRACT

The invention provides non-hormonal vitamin D conjugated to insulin peptides that result in the peptides having increased absorption, bioavailability or circulating half-life when compared to non-conjugated forms. The vitamin D targeting groups are coupled to the insulin peptides via the third carbon on the vitamin D backbone.

22 Claims, 7 Drawing Sheets

(56) References Cited

U.S. PATENT DOCUMENTS

| | | |
|---|---|---|
| 7,186,797 B2 | 3/2007 | West et al. |
| 7,217,689 B1 | 5/2007 | Elliott et al. |
| 7,256,253 B2 | 8/2007 | Bridon et al. |
| 7,307,148 B2 * | 12/2007 | Bousquet-Gagnon ........... A61K 47/48284 530/364 |
| 7,579,324 B2 | 8/2009 | Burnet et al. |
| 7,601,332 B2 | 10/2009 | Vlahov et al. |
| 7,608,681 B2 | 10/2009 | Dennis et al. |
| 7,741,286 B2 | 6/2010 | Bridon et al. |
| 7,741,453 B2 | 6/2010 | Erickson et al. |
| 7,803,777 B2 | 9/2010 | DeFrees |
| 7,982,018 B2 | 7/2011 | Ulich et al. |
| 8,076,476 B2 | 12/2011 | Reeves et al. |
| 8,129,348 B2 | 3/2012 | Besman et al. |
| 8,178,495 B2 | 5/2012 | Chilkoti |
| 8,188,223 B2 | 5/2012 | Beirnaert et al. |
| 8,252,755 B2 | 8/2012 | Yamada et al. |
| 8,551,937 B2 | 10/2013 | Wakabayashi et al. |
| 8,779,109 B2 | 7/2014 | Behrens et al. |
| 8,785,603 B2 | 7/2014 | Sahakian et al. |
| 8,796,443 B2 | 8/2014 | Khvorova et al. |
| 9,173,950 B2 | 11/2015 | Soliman et al. |
| 9,289,507 B2 | 3/2016 | Soliman et al. |
| 2002/0136731 A1 | 9/2002 | Mazess et al. |
| 2002/0141996 A1 | 10/2002 | Le et al. |
| 2003/0113305 A1 | 6/2003 | Osborne et al. |
| 2003/0129194 A1 | 7/2003 | Mazess et al. |
| 2003/0203359 A1 | 10/2003 | Uhlmann et al. |
| 2004/0132104 A1 | 7/2004 | Sackrison et al. |
| 2004/0186063 A1 | 9/2004 | Gutke et al. |
| 2005/0260237 A1 | 11/2005 | Byun et al. |
| 2006/0045880 A1 | 3/2006 | Krieg |
| 2006/0153839 A1 | 7/2006 | Mohamed et al. |
| 2007/0249571 A1 | 10/2007 | Tamarkin |
| 2008/0199960 A1 | 8/2008 | Juliano et al. |
| 2008/0242595 A1 | 10/2008 | Doyle |
| 2009/0131360 A1 | 5/2009 | Woolf et al. |
| 2009/0176253 A1 | 7/2009 | Bieniarz et al. |
| 2009/0305986 A1 | 12/2009 | Belouski et al. |
| 2010/0015046 A1 | 1/2010 | Govindan et al. |
| 2010/0074885 A1 | 3/2010 | Schiff et al. |
| 2010/0104626 A1 | 4/2010 | Leamon et al. |
| 2010/0168033 A1 | 7/2010 | Ghigo et al. |
| 2010/0234303 A1 | 9/2010 | Millar et al. |
| 2010/0323973 A1 | 12/2010 | Leamon et al. |
| 2011/0166063 A1 | 7/2011 | Bossard et al. |
| 2011/0293579 A1 | 12/2011 | Nielsen et al. |
| 2011/0312027 A1 | 12/2011 | Young et al. |
| 2012/0028887 A1 | 2/2012 | Shai et al. |
| 2012/0129766 A1 | 5/2012 | Boettcher et al. |
| 2012/0129767 A1 | 5/2012 | Tulipano et al. |
| 2012/0165377 A1 | 6/2012 | Takizawa et al. |
| 2012/0177646 A1 | 7/2012 | Belouski et al. |
| 2013/0129724 A1 | 5/2013 | Boettcher et al. |
| 2013/0164310 A1 | 6/2013 | Annathur et al. |
| 2013/0172251 A1 | 7/2013 | Kangawa et al. |
| 2013/0231277 A1 | 9/2013 | Mohammadi et al. |
| 2013/0261013 A1 | 10/2013 | Baltzer et al. |
| 2013/0331316 A1 | 12/2013 | Mohammadi et al. |
| 2014/0058063 A1 | 2/2014 | Vlahov et al. |
| 2014/0135260 A1 | 5/2014 | Dong et al. |
| 2014/0170704 A1 | 6/2014 | Young et al. |
| 2014/0179560 A1 | 6/2014 | Olson et al. |
| 2014/0194352 A1 | 7/2014 | Ling et al. |
| 2014/0200261 A1 | 7/2014 | Hoge et al. |
| 2014/0213512 A1 | 7/2014 | Ellison et al. |
| 2014/0256626 A1 | 9/2014 | Santi et al. |
| 2014/0323396 A1 | 10/2014 | Belouski et al. |
| 2015/0104469 A1 | 4/2015 | Soliman et al. |

FOREIGN PATENT DOCUMENTS

| | | |
|---|---|---|
| EP | 0804456 B1 | 8/2002 |
| EP | 1151102 B1 | 4/2006 |
| EP | 1931711 B1 | 4/2009 |
| EP | 2085406 A1 | 8/2009 |
| EP | 2423233 A2 | 2/2012 |
| EP | 2288375 B1 | 4/2012 |
| EP | 2481427 A1 | 8/2012 |
| EP | 2316854 B1 | 12/2013 |
| EP | 2695617 A2 | 2/2014 |
| WO | 9110741 A1 | 7/1991 |
| WO | 9214493 A1 | 9/1992 |
| WO | 9216221 A1 | 10/1992 |
| WO | 9307883 A1 | 4/1993 |
| WO | 9312145 A1 | 6/1993 |
| WO | 9510302 A1 | 4/1995 |
| WO | 9633735 A1 | 10/1996 |
| WO | 9634096 A1 | 10/1996 |
| WO | 9734637 A2 | 9/1997 |
| WO | 9824893 A2 | 6/1998 |
| WO | 9961055 A1 | 12/1999 |
| WO | 0066090 A1 | 11/2000 |
| WO | 0074721 A1 | 12/2000 |
| WO | 0069900 A3 | 2/2001 |
| WO | 0145746 A3 | 10/2001 |
| WO | 02062844 A2 | 8/2002 |
| WO | 02066511 A2 | 8/2002 |
| WO | 02076489 A1 | 10/2002 |
| WO | 03011213 A2 | 2/2003 |
| WO | 02046227 A3 | 4/2003 |
| WO | 03025139 A3 | 8/2003 |
| WO | 2004009124 A2 | 1/2004 |
| WO | 2004011498 A3 | 6/2004 |
| WO | 2004011498 A3 | 6/2004 |
| WO | 2004014865 A3 | 7/2004 |
| WO | 2005097158 A1 | 10/2005 |
| WO | 2005105071 A1 | 11/2005 |
| WO | 2007035922 A2 | 3/2007 |
| WO | WO2007035922 A2 | 3/2007 |
| WO | 2007049941 A1 | 5/2007 |
| WO | 2006116156 A3 | 10/2007 |
| WO | 2007097934 A3 | 11/2007 |
| WO | 2007103455 A3 | 11/2007 |
| WO | 2007012188 A1 | 2/2008 |
| WO | 2008036841 A3 | 10/2008 |
| WO | 2008118013 A2 | 10/2008 |
| WO | 2009121884 A1 | 10/2009 |
| WO | 2011146902 A1 | 11/2011 |
| WO | 2011123813 A3 | 12/2011 |
| WO | 2012041451 A1 | 4/2012 |
| WO | 2012158962 A2 | 11/2012 |
| WO | 2013033230 A1 | 3/2013 |
| WO | 2013163162 A1 | 10/2013 |
| WO | WO2013172967 A1 | 11/2013 |
| WO | 2014041024 A1 | 3/2014 |
| WO | 2013040093 A3 | 5/2014 |
| WO | 2014081864 A1 | 5/2014 |
| WO | 2014083427 A2 | 6/2014 |

OTHER PUBLICATIONS

Frolik, et al. Anabolic and Catabolic Bone Effects of Human Parathyroid Hormone (1-34) are Predicted by Duration of Hormone Exposure. Bone 33: 372-379 (2003).

Presta. Antibody Engineering. Current Opinion in Biotechnology 3:394-398 (1992).

Presta, et al. Humanization of an Anti-Vascular Endothelial Growth Factor Monoclonal Antibody for the Therapy of Solid Tumors and Other Disorders. Cancer Research 57:4593-4599 (1997).

Satterwhite, et al. Pharmacokinetics of Teriparatide (rhPTH[1-34]) and Calcium Pharmacodynamics in Postmenopausal Women with Osteoporosis. Calcif Tissue Int. 87:485-492 (2010).

Speeckaert, et al. Biological and clinical aspects of the vitamin D binding protein (Gc-globulin) and its polymorphism. Clinica Chimica Acta 372: 33-42 (2006).

Winer K.K., et al. Synthetic Human Parathyroid Hormone 1-34 Replacement Therapy: A Randomized Crossover Trial comparing

(56) References Cited

OTHER PUBLICATIONS

Pump Versus Injections in the Treatment of Chronic Hypoparathyroidism. J. Clin. Endocrinal. Metab. 97(2):391-399 (2012).
PCT Search Report and Written Opinion dated Jun. 5, 2013, from PCT App. No. PCT/US13/31788, filed on Mar. 14, 2013.
Kozbor, "A Human Hybrid Myeloma for Production of Human Monoclonal Antibodies," J. Immunol, 133: 3001 (1984).
Kutner A, et al., 1986, "Photoactivable Analogues for Labeling 25-Hydroxyvitamin D3 Serum Binding Protein and for 1,25-Dihydroxyvitamin D3 Intenstinal Receptor Protein," Bioorganic Chemistry 14: 134-147.
Langenheim JF and Chen WY, 2009, "Improving the Pharmacokinetics/Pharmacodynamics of Prolactin, GH, and Their Antagonists by Fusion to a Synthetic Albumin-Binding Peptide," Journal of Endocrinology 203:375-387.
Leamon CP and Low PS, 2001, "Folate-Mediated Targeting: From Diagnostics to Drug and Gene Delivery," Drug Discovery Today 6(1): 44-51.
Leamon CP and Reddy JA, 2004, "Folate-Targeted Chemotherapy," Advanced Drug Delivery Reviews 56: 1127-1141.
Lee et al., "Bivalent antibody phage display mimics natural immunoglobulin," J. Immunol. Methods 284(1-2): 119-132 (2004).
Lee et al., "High-affinity Human Antibodies from Phage-displayed Synthetic Fab Libraries with a Single," J. Mol. Biol. 340(5): 1073-1093 (2004).
Leyssens C, et al., 2014, "The Future of Vitamin D Analogues," Frontiers in Physiology 5: Article 122.
Liang S, et al., 2013, "Structural Basis for Treating Tumor Necrosis Factor alpha (TNFalpha)-associated Diseases with the Therapeutic Antibody Infliximab," Journal of Biological Chemistry 288: 13799-13807.
Liebner R, et al., 2014, "Protein HESylation for Half-Life Extension: Synthesis, Characterization and Pharmacokinetics of HESylated Anakinra," European Journal of Pharmaceutics and Biopharmaceutics 87: 378-385.
Link RP, et al., 1987, "Photoaffinity Labeling of Serum Vitamin D Binding Protein by 3-Deoxy-3-azido-25-hydroxyvitamin D3," Biochemistry 26: 3957-3964.
Lips P, 2006, "Vitamin D Physiology," Progress in Biophysics and Molecular Biology 92: 4-8.
Lonberg 2008, "Fully human antibodies from transgenic mouse and phage display platforms" Curr Opin Immunol. Aug. 2008;20(4):450-9.
Lonberg and Huszar, Intern. Rev. Immunol. 13: 65-93 (1995).
Lonberg et al.,"Antigen-specific human antibodies from mice comprising four distinct genetic modifications," Nature 368: 856-859 (1994).
Lu Y, et al., 2004, "Folate Receptor-Targeted Immunotherapy of Cancer: Mechanism and Therapeutic Potential," Advanced Drug Delivery Reviews 56: 1161-1176.
Makrides SC, et al., 1996, "Extended in Vivo Half-Life of Human Soluble Complement Receptor Type 1 Fused to a Serum Albumin-Binding Receptor," Journal of Pharmacology and Experimental Therapeutics 277(1): 534-542.
Marks et al., "By-passing Immunization Human Antibodies from V-gene Libraries Displayed on Phage," J. Mol. Biol, 222: 581-597 (1991).
Marks et al., "By-Passing Immunization: Building High Affinity Human Antibodies by Chain Shuffling," Bio. Technology 10: 779-783 (1992).
McIntyre et al., "Effects of new analogues of vitamin D on bone cells: Implications for treatment of uremic bone disease," Kidney Int. 55: 500 (1999).
McLeod et al, "The Vitamin D-binding Protein, &-Fetoprotein, Albumin Multigene Family: Detection of Transcripts in Multiple Tissues," J Biol Chem. 264(2):1260-7 (1989).
Mero A, et al., 2013, "Conjugation of Hyaluronan to Proteins," Carbohydrate Polymers 92: 2163-2170.

Misbah S, et al., 2009, "Subcutaneous immunoglobulin: opportunities and outlook," Clinical and Experimental Immunology 158(Suppl 1): 51-59.
Morrison, "Success in Specification," Nature 368: 812-813 (1994).
Mu J, et al, 2012, "FGF21 Analogs of Sustained Action Enabled by Orthogonal Biosynthesis Demonstrate Enhanced Antidiabetic Pharmacology in Rodents," Diabetes 61:505-512.
Müler DN, et al., 2011, "Vitamin D Review," Journal of the Renin-Angiotensin-Aldosterone System 12: 125-8.
Nanocs PEG Products located at: http://www.nanocs.com/PEG/VTPEG.htm.
Neary NM, et al., 2004, "Ghrelin Increases Energy Intake in Cancer Patients with Impaired Appetite: Acute, Randomized, Placebo-Controlled Trial," The Journal of Clinical Endocrinology & Metabolism 89(6): 2832-2836.
Nestor, J.J., Jr. (2007) Comprehensive Medicinal Chemistry II 2: 573-601.
Neuberger, "Generating high-avidity human Mabs in mice," Nature Biotechnol. 14: 826 (1996).
Norman AW, et al., 2001, "Ligands for the Vitamin D Endocrine System: Different Shapes Function as Agonists and Antagonists for Genomic and Rapid Response Receptors or as a Ligand for the Plasma Vitamin D Binding Protein," Journal of Steroid Biochemistry and Molecular Biology 76: 49-59.
Notice of Allowance dated Jun. 23, 2009, for U.S. Appl. No. 10/765,336.
Ono Y, 2014, "Multifunctional and Potent Roles of the 3-Hydroxypropoxy Group Provide Eldecalcitol's Benefit in Dsteoporosis Treatment," Journal of Steroid Biochemistry & Molecular Biology 139: 88-97.
Park S, et al., 2014, "A Novel Delivery Platform for Therapeutic Peptides," Biochemical and Biophysical Research Communications 450(1): 13-18.
Payne RJ, et al., 2004, "Synthesis and Protein Conjugation Studies of Vitamin K Analogues," Bioorganic & Medicinal Chemistry 12: 5785-5791.
Peleg S and Posner GH, 2003, "Vitamin D Analogs as Modulators of Vitamin D Receptor Action," Current Topics in Medicinal Chemistry 3(14): 1555-72.
Petrus AK, et al., 2009, "Exploring the Implications of Vitamin B12 Conjugation to Insulin on Insulin Receptor Binding," ChemMedChem 4: 421-426.
Pfutzner, A and Forst, T, 2005, "Pulmonary insulin delivery by means of the Technosphere™ drug carrier mechanism," Expert Opin Drug Deliv 2:1097-1106.
Presta, "Antibody Engineering," Current Opinion in Biotechnology, 3:394-398 (1992).
Punj V, et al., 2004, "Effect of Vitamin D Analogue (1alpha Hydroxy D5) Immunoconjugated to Her-2 Antibody on Breast Cancer," International Journal of Cancer 108: 922-929.
Rattan, S.I., et al. (1992), "Protein Synthesis, Post translational Modifications, and Aging," Ann N Y Acad Sci 663: 48-62.
Ray R, et al., 1986, "Photoathnity Labeling of the Rat Plasma Vitamin D Binding Protein with [26,27-3H]-25-Hydroxyvitamin D3 3beta-[N-(4-azido-2-nitrophenyl)glycinate]," Biochemistry 25(17): 4729-4733.
Reddy JA, et al., 2007, "Folate Receptor-Specific Antitumor Activity of EC131, a Folate-Maytansinoid Conjugate," Cancer Research 67: 6376-6382.
Revelle et al., "Synthesis and Biological Activity of 3beta-Fluorovitamin D3,: Comparison of the Biological Activity of 3beta-Fluorovitamin D3, and 3-Deoxyvitamin D3," J. Steroid Biochem. 22:469-474 (1985).
Riechmann et al., "Reshaping human antibodies for therapy," Nature 332:323-329 (1988).
Rosenstock J, et al., 2009, "Potential of Albiglutide, a Long-Acting GLP-1 Receptor Agonist, in Type 2 Diabetes," Diabetes Care 32(10): 1880-1886.
Salmaso S, et al., 2009, "Targeting Glioma Cells in Vitro with Ascorbate-Conjugated Pharmaceutical Nanocarriers," Bioconjugate Chemistry 20: 2348-2355.

(56) References Cited

OTHER PUBLICATIONS

Sasson K, et al., 2010, "Engineering Prolonged Acting Prodrugs Employing an Albumin-Binding Probe that Undergoes Slow Hydrolysis at Physiological Conditions," Journal of Controlled Release 142: 214-220.
Schlapschy M, et al., 2013,"PASylation: A Biological Alternative to PEGylation for Extending the Plasma Half-Life of Pharmaceutically Active Proteins," Protein Engineering, Design & Selection 26: 489-501.
Erben and Musculoskel, "Vitamin D analogs and bone," Neuron Interact. 2(1):59-69 (2001).
Fellouse, "Synthetic antibodies from a four-amino-acid code: A dominant role for tyrosine in antigen recognition," Proc. Natl. Acad. Sci. USA 101(34): 12467-12472 (2004).
Fishbum, "The Pharmacology of PEGylation: Balancing PD with PK to Generate Novel Therapeutics," J. Pharm. Sci. 97:4167-4183 (2008).
Fisher CJ, et al., 1996, "Treatment of Septic Shock with the Tumor Necrosis Factor Receptor:Fc Fusion Protein," The New England Journal of Medicine 334: 1697-1702.
Freeman JN, et al., 2013, "Chronic central ghrelin infusion reduces blood pressure and heart rate despite increasing appetite and promoting weight gain in normotensive and hypertensive rats," Peptides 42: 35-42.
Gabizon A, et al., 2004, "Tumor Cell Targeting of Liposome-Entrapped Drugs with Phospholipid-Anchored Folic Acid-PEG Conjugates," Advanced Drug Delivery Reviews 56: 1177-1192.
Gaich G, et al., 2013, "The Effects of LY2405319, an FGF21 Analog, in Obese Human Subjects with Type 2 Diabetes," Well Metabolism 18: 333-340.
Garay RP, et al., 2012, "Antibodies against Polyethylene Glycol in Healthy Subjects and in Patients Treated with PEG-conjugated Agents," Expert Opinion on Drug Delivery 9(11): 1319-1323.
Gong N, et al., 2011, "Site-Specific PEGylation of Exenatide Analogues Markedly Improved Their Glucoregulatory Activity," British Journal of Pharmacology 163: 399-412.
Gourlet, P., et al. (1998), "Interaction of lipophilic VIP derivatives with recombinant VIP rPACAP 1 and VIP rPACAP receptors," Eur J Pharmacol 354: 105-111.
Haddad JG, 1995, "Plasma Vitamin D-Binding Protein (Gc-Globulin): Multiple Tasks," Journal of Steroid Biochemistry and Molecular Biology 53: 579-82.
Haddad JG, et al., 1992, "Identification of the Sterol- and Actin-Binding Domains of Plasma Vitamin D Binding Protein (Gc-Globulin)," Biochemistry 31: 7174-7181.
Haddad JG, et al., 1993, "Human Plasma Transport of Vitamin D After its Endogenous Synthesis," Journal of Clinical Investigation 91: 2552-2555.
Hakimelahi GH, et al., 2001, "Design and Synthesis of a Cephalosporin-Retinoic Acid Prodrug Activated by a Monoclonal Antibody-betaLactamase Conjugate," Bioorganic & Medicinal Chemistry 9: 2139-2147.
Harris JM and Chess RB, 2003, "Effect of PEGylation on Pharmaceuticals," Nature Reviews in Drug Discovery 2: 214-221.
Harris, "Therapeutic Monoclonals," Biochem. Soc. Transactions 23: 1035-1038 (1995).
Harvill ET and Morrison SL, 1995, "An IgG3-IL2 Fusion Protein Activates Complement, Binds Fc(gamma)RI, Generates LAK Activity and Shows Enhanced Binding to the High Affinity IL-2R," Immunotechnology 1: 95-105.
Havelund S, et al., 2004, "The Mechanism of Protraction of Insulin Determir, a Long-Acting Acylated Analog of Human Insulin," Pharmaceutical Research 21(8): 1498-1504.
Herbst RS, 2009, "Safety, Pharmacokinetics, and Antitumor Activity of AMG 386, a Selective Angiopoietin Inhibitor, in Adult Patients with Advanced Solid Tumors," Journal of Clinical Oncology 27: 3557-3565.

Hiura et. al., "Effects of Ghrelin Administration During Chemotherapy With Advanced Esophageal Cancer Patients," cancer Jan. 26, 2012, http://onlinelibrary.wiley.com/doi/10.1002/cncr.27430/abstract.
Hoffmann E, et al., 2013, "PK Modulation of Haptenylated Peptides via Non-covalent Antibody Complexation," Journal of Controlled Release 171: 48-56.
Holick MF (editor), 2010, "Vitamin D: Physiology, Molecular Biology, and Clinical Applications," Humana Press pp. 0-1155.
Holt LJ, et al., 2008, "Anti-serum Albumin Domain Antibodies for Extending the Life-Time of Short Lived Drugs," Protein Engineering, Design, & Selection 21(5): 283-288.
Hoogenboom et al., "Multi-subunit proteins on the surface of filamentous phage: methodologies for displaying antibody (Fab) heavy andlight chains," Nucl. Acids Res., 19: 4133-4137 (1991).
Huang A, et al., "A Better Anti-Diabetic Recombinant Human Fibroblast Growth Factor 21 (rhFGF21) Modified with Polyethylene Glycol," PLoS ONE 6(6): e20669.
Hurle and Gross, "Protein engineering techniques for antibody humanization," Curr. Op. Biotech. 5:428-433 (1994).
Islam I, et al., 1994, "Evaluation of a Vitamin-Cloaking Strategy for Oligopeptide Therapeutics: Biotinylated HIV1-Protease Inhibitors," Journal of Medicinal Chemistry 37: 293-304.
Itoh N, 2014, "FGF21 as a Hepatokine, Adipokine, and Myokine in Metabolism and Diseases," Frontiers in Endocrinology 5: article 107.
Jain, "PEGylation: An Approach for Drug Delivery. A Review," Grit. Rev. Ther. Drug Carrier Syst. 25:403-447 (2008).
Jakobovits et al., "Analysis of homozygous mutant chimeric mice: Deletion of the immunoglobulin heavy-chain joining region blocks B-cell," Proc. Natl. Acad. Sci USA, 90: 2551 (1993).
Jakobovits et al.,"Germ Line Transmission and Expression of a Human-Derived Yeast Artificial Chromosome," Nature 362: 255-258 (1993).
Jevsevar S, et al., 2010, "PEGylation of Therapeutic Proteins," Biotechnology Journal 5: 113-128.
Jia ZQ, et al., 2012, "Cardiovascular Effects of a PEGylated Apelin," Peptides 38: 181-188.
Jones et al., Replacing the Complementarity-determining Regions in a Human Antibody with those from a Mouse, Nature 321 :522-525 (1986).
Katre NV, et al., 1987, "Chemical Modification of Recombinant Interleukin 2 by Polyethylene Glycol Increases its Potency in the Murine Meth A Sarcoma Model," Proceedings of the National Academy of Sciences, USA 84: 1487-1491.
Kaul, R. and Balaram, P. (1999), "Stereochemical Control of Peptide Folding," Bioorg Med Chem 7: 105-117.
Kaya T, et al., 2009, "Covalent Labeling of Nuclear Vitamin D Receptor with Affinity Labeling Reagents Containing a cross-linking Probe at Three Different Positions of the Parent Ligand: Structural and Biochemical Implications," Bioorganic Chemistry 37: 57-63.
Kharitonenkov A and Adams AC, 2014, "Inventing New Medicines: The FGF21 Story," Molecular Metabolism 3: 221-229.
Kharitonenkov and Shanafelt, Curr. Opin. Investig. Drugs 10:359-364 (2009), Abstract Only.
Kharitonenkov et al., "FGF-21 as a novel metabolic regulator," J. Clin. Invest. 115:1627-1635 (2005).
Kim KH and Lee M-S, 2014, "FGF21 as a Stress Hormone: The Roles of FGF21 in Stress Adaptation and the Treatment of Metabolic Diseases," Diabetes & Metabolism Journal 38: 245-251.
Kliewer and Mangelsdorf,"Fibroblast growth factor 21: from pharmacology to physiology1-4," Am. J. Clin. Nutr. 91:254S-257S (2010).
Knight DM, et al., 1993,"Construction and Initial Characterization of a Mouse-Human Chimeric Anti-TNF Antibody," Molecular Immunology 30(16): 1443-1453.
Knutson et al., Biochem Pharmacol 53: 829 (1997).
Kobayashi N, et al., 1992, "Production and Specificity of Antisera Raised against 25-Hydroxyvitamin D3-[C-3]-Bovine Serum Albumin Conjugates," Steroids 57: 488-493.

(56) References Cited

OTHER PUBLICATIONS

Kobayashi N, et al., 1994, "Production of a Group-Specific Antibody to 1alpha,25-dihydroxyvitamin D and its Derivatives Having the 1alpha,3beta-dihydroxylated A-Ring Structure," Steroids 59: 404-411.
Kobayashi N, et al., 1994, "Specificity of the Polyclonal Antibodies Raised against a Novel 25-Hydroxyvitamin D3-Bovine Serum Albumin Conjugate Linked through the C11alpha Position," Journal of Steroid Biochemistry & Molecular Biology 48: 567-572.
Kohler et al, "Continuous cultures of fused cells secreting antibody of predefined specificity," Nature, 256: 495 (1975).
Kong J-H, et al., 2010, "Long-Acting Hyaluronate-Exendin 4 Conjugate for the Treatment of Type 2 Diabetes," Biomaterials 31: 4121-4128.
Kontermann R (editor), 2012, "Therapeutic Proteins: Strategies to Modulate Their Plasma Half-lives," Wiley-Blackwell, pp. 0-339.
Abe et al., Synthetic analogues of vitamin D3 with an oxygen atom in the side chain skeleton, FEBS Lett. 226:58-62 (1987).
Addo JK, et al., 2002, "The C19 Position of 25-Hydroxyvitamin D3 Faces Outward in the Vitamin D Sterol-Binding Pocket of Vitamin D-Binding Protein," Bioorganic & Medicinal Chemistry Letters 12: 279-281.
Ahsan, F et al., 2001, Enhanced Bioavailability of Calcitonin Formulated with Alkylglycosides following Nasal and Ocular Administration in Rats, Pharm Res 18:1742-1746.
Amiram M, et al., 2013, "A Depot-Forming Glucagon-Like Peptide-1 Fusion Protein Reduces Blood Glucose for Five Days with a Single Injection," Journal of Controlled Release 172: 144-151.
Amiram M, et al., 2013, "Injectable Protease-Operated Depots of Glucagon-Like Peptide-1 Provide Extended and Tunable Glucose Control," Proceedings of the National Academy of Sciences, USA 110(8): 2792-2797.
Arnaud J and Constans J, 1993, "Affinity Differences for Vitamin D Metabolites Associated with the Genetic Isoforms of the Human Serum Carrier Protein (DBP)," Human Genetics 92: 183-188.
Arnold, JJ et al., 2004, Correlation of Tetradecylmaltoside Induced Increases in Nasal Peptide Drug Delivery with Morphological Changes in Nasal Epithelial Cells, J Pharm Sci 93: 2205-13.
Amusch CJ, et al., 2012, "Ultrashort Peptide Bioconjugates Are Exclusively Antifungal Agents and Synergize with Cyclodextrin and Amphotericin B," Antimicrobial Agents and Chemotherapy 56(1) 1-9.
Baggio LL, et al., 2004, "A Recombinant Human Glucagon-Like Peptide (GLP)-1-Albumin Protein (Albugon) Mimics Peptidergic Activation of GLP-1 Receptor-Dependent Pathways Coupled with Satiety, Gastrointestinal Motility, and Glucose Homeostasis," Diabetes 53: 2492-2500.
Bailon P, et al., 2001, "Rational Design of a Potent, Long-Lasting Form of Interferon: a 40 kDa Branched Polyethylene Glycol-Conjugated Interferon Alpha-2a for the Treatment of Hepatitis C," Bioconjugate Chemistry 12(2): 195-202.
Bao W, et al., 2013, "Novel Fusion of GLP-1 with a Domain Antibody to Serum Albumin Prolongs Protection against Myocardial Ischemia/Reperfusion Injury in the Rat," Cardiovascular Diabetology 12: 148.
Barrington P, et al., 2011, "A 5-Week Study of the Pharmacokinetics and Pharmacodynamics of LY2189265, a Novel, Long-Acting Glucagon-Like Peptide 1 Analogue, in Patients with Type 2 Diabetes," Diabetes, Obesity, and Metabolism 13:426-433.
Barrington P, et al., 2011, "LY2189265, a Long-Acting Glucagon-Like Peptide 1 Analogue, Showed a Dose-Dependent Effect on Insulin Secretion in Healthy Patients," Diabetes, Obesity, and Metabolism 13:434-438.
Ben-Shabat S, et al., 2005, "Vitamin D3-Based Conjugates for Topical Treatment of Psoriasis: Synthesis, Antiproliferative Activity, and Cutaneous Penetration Studies," Pharmaceutical Research 22(1): 50-57.

Bishop JE, et al., 1994, "Profile of Ligand Specificity of the Vitamin D Binding Protein for 1alpha-25-dihydroxyvitamin D3 and its Analogues," Journal of Bone and Mineral Research 9(8): 1277-1288.
Blouch K, et al., 1997, "Molecular Configuration and Glomerular Size Selectivity in Healthy and Nephrotic Humans," American Journal of Physiology 273 (Renal Physiology 42): F430-F437. (May 20, 1997).
Boemer et al., Human mAb From in Vitro-Primed Lymphocytes, J. Immunol, 147: 86-95 (1991).
Bouillon R, et al., 1980, "Comparative Study of the Affinity of the Serum Vitamin D Binding Protein," Journal of Steroid Biochemistry 13: 1029-1034.
Bouillon R, et al., 1991, "Vitamin D Analogues with Low Affinity for the Vitamin D Binding Protein: Enhanced in Vitro and Decreased in Vivo Activity," Journal of Bone and Mineral Research 6(10): 1051-1057.
Bouman-Theo E, et al., 2008, "A Phase I, Single and Fractionated, Ascending-Dose Study Evaluating the Safety, Pharmacokinetics, Pharmacodynamics, and Immunogenicity of an Erythropoietin Mimetic Antibody Fusion Protein (CNTO 528) in Healthy Male Subjects," Journal of Clinical Pharmacology 48: 1197-1207.
Cai Y, et al., 2013, "Long-Acting Preparations of Exenatide," Drug Design, Development, and Therapy 7: 963-970.
Camacho RC, et al., 2013, "PEGylated FGF21 Rapidly Normalizes Insulin-Stimulated Glucose Utilization in Diet-Induced Insulin Resistant Mice," European Journal of Pharmacology 715: 41-45.
Capon DJ, et al., 1989, "Designing CD4 Immunoadhesions for AIDS Therapy," Nature 337: 525-531.
Carlberg C, 2003, "Molecular Basis for the Selective Activity of Vitamin D Analogues," Journal of Cellular Biochemistry 88:274-281.
Chae SY, et al., 2009, "Pharmacokinetic and Pharmacodynamic Evaluation ofSite-Specific PEGylated Glucagon-Like Peptide-1 Analogs asFlexible Postprandial-Glucose Controllers," Journal of Pharmaceutical Sciences 98(4): 1556-1567.
Chae SY, et al., 2010, "Biochemical, Pharmaceutical, and Therapeutic Properties of Long-Acting Lithocholic Acid Derivatized Exendin-4 Analogues," Journal of Controlled Release 142: 206-213.
Chae SY, et al., 2010, "The Fatty Acid Conjugated Exendin-4 Analogues for Type 2 Antidiabetic Therapeutics," Journal of Controlled Release 144: 10-16.
Chalasani KB, et al., 2007, "Effective Oral Delivery of Insulin in Animal Models Using Vitamin B12-coated Dextran Nanoparticles," Journal of Controlled Release 122: 141-150.
Chen et al., Selection and Analysis of an Optimized Anti-VEGF Antibody: Crystal Structure of an Affinity-matured Fab, J. Mol. Biol. 293:865-881 (1999).
Chen S, et al., 2010, "Mechanism-Based Tumor-Targeting Drug Delivery System. Validation of Efficient Vitamin Receptor-Mediated Endocytosis and Drug Release," Bioconjugate Chemistry 21: 979-987.
Choi H-I, et al., 2009, "A Novel L-Ascorbic Acid and Peptide Conjugate with Increased Stability and Collagen Biosynthesis," BMB Reports 42(11): 743-746.
Clackson et al., Making antibody fragments using phage display libraries, Nature, 352: 624-628 (1991).
Clardy-James S, et al., 2013, "Synthesis, Characterization, and Pharmacodynamics of Vitamin-B12-Conjugated Glucagon-Like Peptide-1," ChemMedChem 8: 582-586.
Clark et al. Long-acting Growth Hormones Produced by Conjugation with Polyethylene Glycol*, J. Biol. Chem. 271:21969-21977 (1996).
Cleland JL, et al., 2012, "A Novel Long-Acting Human Growth Hormone Fusion Protein (VRS-317): Enhanced in Vivo Potency and Half-Life," Journal of Pharmaceutical Sciences 101(8): 2744-2754.
Clemens TL, et al., 1983, "A Simple Method for Generation of Antibodies with Specificity for 1,25-Dihydroxyergocalciferol and 1,25-Dihydroxycholecalciferol," Steroids 42(5): 503-509.

(56) References Cited

OTHER PUBLICATIONS

Conforti A, et al., 1987, "PEG Superoxide Dismutase Derivatives: Anti-Inflammatory Activity in Carrageenan Pelurisy in Rats," Pharmacological Research Communications 19: 287-294.
Cooke NE and Haddad JG, 1989, "Vitamin D Binding Protein (Gc-Globulin)," Endocrinology Reviews 10: 294-307.
Datta-Mannan A, et al, 2012, "Influence of improved FcRn binding on the subcutaneous bioavailability of monoclonal antibodies in cynomolgus monkeys," MAbs. 4(2):267-73.
de Schepper J, et al., 2011, "Long-Acting PEGylated Human GH in Children with GG Deficiency: A Single-Dose, Dose-Escalation Trial Investigating Safety, Tolerability, Pharmacokinetics and Pharmacodynamics," European Journal of Endocrinology 165(3): 401-409.
de Smidt PC, et al., 1991, "Association of Antisense Oligonucleotides with Lipoproteins Prolongs the Plasma Half-Life and Modifies the Tissue Distribution," Nucleic Acids Research 19(17): 4695-4700.
DeLuca HF, 2008, "Evolution of our Understanding of Vitamin D," Nutrition Reviews 66(suppl. 2): S73-8.
Dennis MS, et al., 2002, "Albumin Binding as a General Strategy for Improving the Pharmacokinetics of Proteins," Journal of Biological Chemistry 277: 35035-35043.
Dennis MS, et al., 2007, "Imaging Tumors with an Albumin-Binding Fab, a Novel Tumor-Targeting Agent," Cancer Research 67: 254-261.
Ding S, et al., 2014, "Multivalent Antiviral XTEN-Peptide Conjugates with Long in Vivo Half-Life and Enhanced Solubility," Bioconjugate Chemistry 25(7): 1351-9.
Doores, K., et al., "Direct deprotected glycosyl-asparagine ligation" Chem. Commun., 1401-1403, 2006.
Elliott S, et al. 2003, "Enhancement of in Vivo Therapeutic Protein Activities through Glycoengineering," Nature Biotechnology 21: 414-421.
SciFinder, Maleimide Side, Nov. 6, 2012.
SciFinder, Minimal Vitamin D side, Nov. 6, 2012.
SciFinder, Vitamin D side, Nov. 6, 2012.
Seifter, S. and Englard, S. (1990), "Analysis for Protein Modifications and Nonprotein Cofactors," Methods Enzymol 182: 626-646.
Sidhu et al., "Phage-displayed Antibody Libraries of Synthetic Heavy Chain Complementarity Determining Regions," J. Mol. Biol. 338(2): 299-310 (2004).
Slatopolsky et al., "A New Analog of Calcitriol, 19-Nor-1,25-(OH),D Suppresses Parathyroid Hormone Secretion in Uremic Rats in theAbsence of Hypercalcemia," Am J. Kidney Dis. 26: 852 (1995).
So et al., "A Novel Gemini Vitamin D Analog Represses the Expression of a Stem Cell Marker CD44 in Breast cancer," Mol Pharmacol. 79(3):360-7 (2011).
Stamatov SD and Gronowitz S, 1990, "Glyceroamidothiophosphates of Cholecalciferol (Vitamin D3)," Lipids 25: 149-151.
Steddon et al. "Vitamin D analogues: how do they differ and what is their clinical role," Nephrol. Dial. Transplant. 16 (10): 1965-1967 (2001).
Sun C, et al., 2013, "Bifunctional PEGylated Exenatide-Amylinomimetic Hybrids to Treat Metabolic Disorders: An Example of Long-Acting Dual Hormonal Therapeutics," Journal of Medicinal Chemistry 56: 9328-9341.
Swamy N, et al., 1995, "Affinity Purification of Human Plasma Vitamin D-Binding Protein," Protein Expression and Purification 6: 185-188.
Swamy N, et al., 1997, "Roles of Structure and Orientation of Ligands and Ligand Mimics inside the Ligand-Binding Pocket of the Vitamin D-Binding Protein," Biochemistry 36: 7432-7436.
Swamy N, et al., 2000, "Probing the Vitamin D Sterol Binding Pocket of Human Vitamin D Binding Protein with Bromoacetate Affinity Labeling Reagents Containing the Affinity Probe at C-3, C-6, C-11, and C-19 Positions of Parent Vitamin D Sterols," Archives of Biochemistry and Biophysics 373(2): 471-478.
Teegarden et. al.," Determination of the Affinity of Vitamin D Metabolites to Serum Vitamin D Binding Protein Using AssayEmploying Lipid-Coated Polystyrene Beads," Anal. Biochemistry 199(2):293-299 (1991).
Touraine P, et al., 2009, "Lipoatrophy in GH Deficient Patients Treated with a Long-Acting PEGylated GH," European Journal of Endocrinology 161(4): 533-40.
Trussel S, et al., 2009, "New Strategy for the Extension of the Serum Half-Life of Antibody Fragments," Bioconjugate Themistry 20: 2286-2292.
Vaswani and Hamilton, Ann. Allergy, Asthma & Immunol. 1:105-115 (1998).
Verboven C, et al., 2002, "A Structural Basis for the Unique Binding Features of the Human Vitamin D-Binding Protein," Nature Structural Biology 9: 131-6.
Vestergaard ET, et al., "Constant intravenous infusion in healthy men: clinical pharmacokinetics and metabolic effects," Am J Physiol Endocrinol Metab 292:E1829-E1836.
Vlahov IR, et al., 2006, "Design and Regioselective Synthesis of a New Generation of Targeted Chemotherapeutics. Part 1: EC145, a Folic Acid Conjugate of Desacetylvinblastine Monohydrazide," Bioorganic & Medicinal Chemistry Letters 16: 5093-5096.
Nang X-F, et al., 2007, "A Peptide Conjugate of Vitamin E Succinate Targets Breast Cancer Cells with High ErbB2 Expression," Cancer Research 67: 3337-3344.
Wootton AM, 2005, "Improving the Measurement of 25-Hydroxyvitamin D," Clinical Biochemist Reviews 26: 33-6.
Nu B and Sun Y-N, 2014, "Pharmacokinetics of Peptide-Fc Fusion Proteins," Journal of Pharmaceutical Sciences 103:53-64.
Ku J et al., 2009. "Acute glucose-lowering and insulin-sensitizing action of FGF21 in insulin-resistant mouse models—association with liver and adipose tissue effects," Am J Physiol Endocrinol Metab 297: E1105-E1114.
Xu et al., 2014, Long-acting hypoglycemic effects of PEGylated FGF21 and insulin glargine in mice with type 1 diabetes, Journal of Diabetes and Its Complications, in press, http://dx.doi.org/10.1016/j.diacomp.2014.10.001.
Zeidler J, et al., 2012, "Biologic TNF inhibiting agents for treatment of inflammatory rheumatic diseases: dosing patterns and related costs in Switzerland from a payers perspective" Health Economics Review 2:20.
Zhang J, et al. 2010, "Identification of Two Distinct Cell Binding Sequences in the Vitamin D Binding Protein," Biochimica et Biophysica Acta 1803: 623-629.
Zhang Q, et al., 2010, "Synthesis of C-11 Linked Active Ester Derivatives of Vitamin D3 and Their Conjugations to 42-Residue Helix-Loop-Helix Peptides," Tetrahedron 66: 4577-4586.
Zhang, L and Bulaj, G. (2012). "Converting Peptides into Drug Leads by Lipidation," Curr Med Chem 19: 1602-1618.
Zhao J, et al., 2013, "Targeted Co-delivery of Docetaxel and siPlk1 by Herceptin-conjugated Vitamin E TPGS Based Immunomicelles," Biomaterials 34: 3411-3421.
Zhou K, et al., 2009, "Studies of Poly(ethylene glycol) Modification of HM-3 Polypeptides," Bioconjugate Chemistry 20: 932-936.
Gozes, "Potential clinical applications of vasoactive intestinal peptide: a selected update," Best Practice & Research clinical Endocrinology & Metabolism vol. 18, No. 4, pp. 623-640, 2004.
Hernandez-Martin, et al. "Synthesis of vitamin D3 analogues with A-ring modifications to directly measure vitamin D levels in biological samples," Bioorganic & Medicinal Chemistry 21, Oct. 2013.
PCT Search Report and Written Opinion for PCT application No. PCT/US2015/056737, mailed on Mar. 31, 2016.
PCT Search Report and Written Opinion for PCT application No. PCT/US2015/056723, mailed on Mar. 31, 2016.
PCT Invitation to Pay Additional Fees for PCT application No. PCT/US2015/056737, mailed on Feb. 3, 2016.
PCT Invitation to Pay Additional Fees for PCT application No. PCT/US2015/056723, mailed on Feb. 3, 2016.

\* cited by examiner

Figure 2
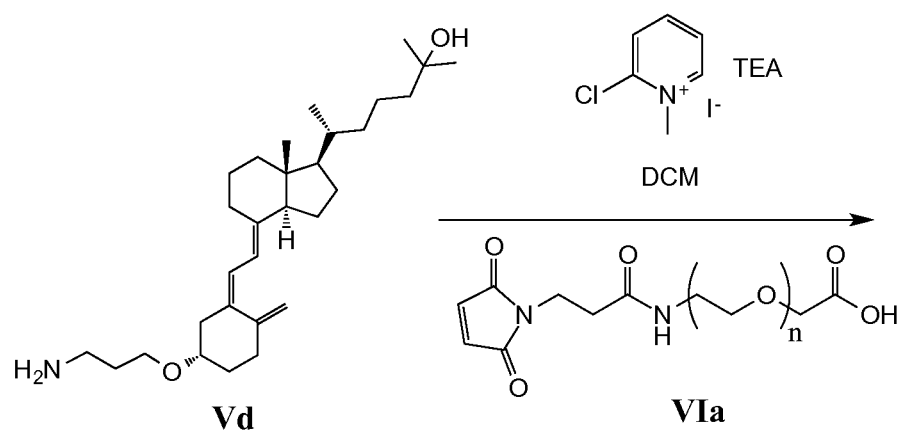
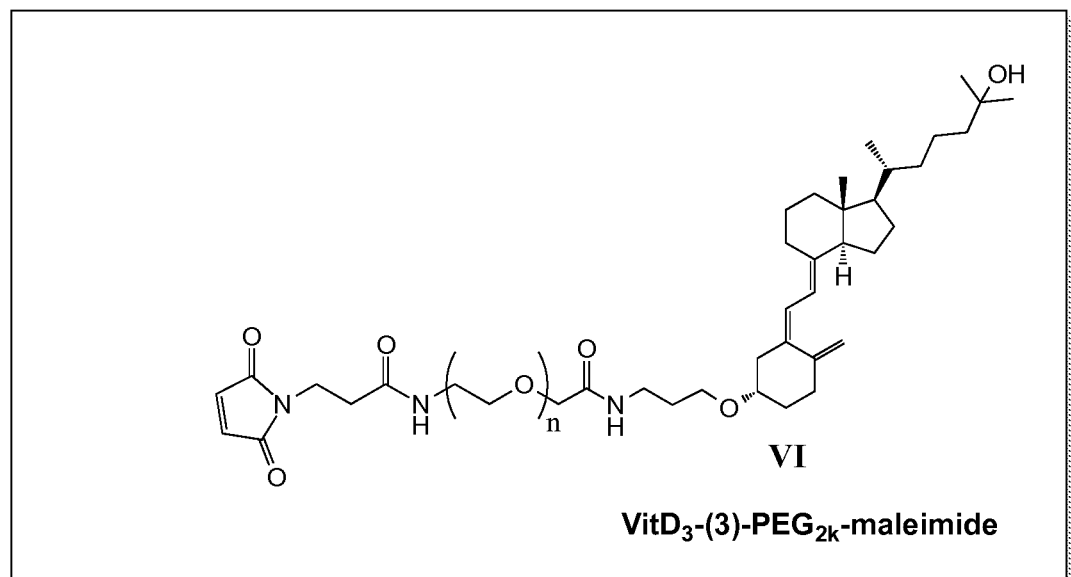
VI
VitD$_3$-(3)-PEG$_{2k}$-maleimide

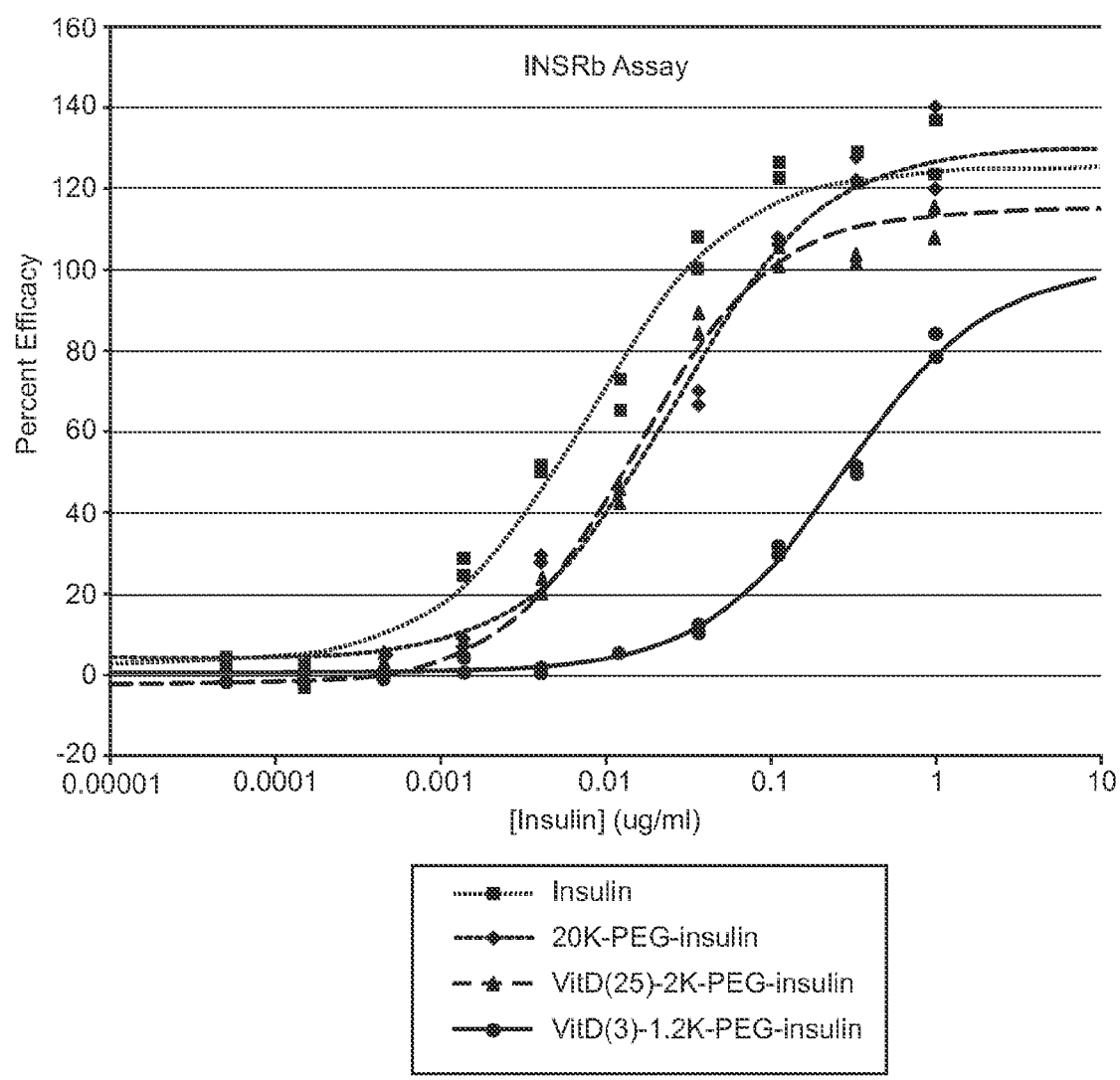

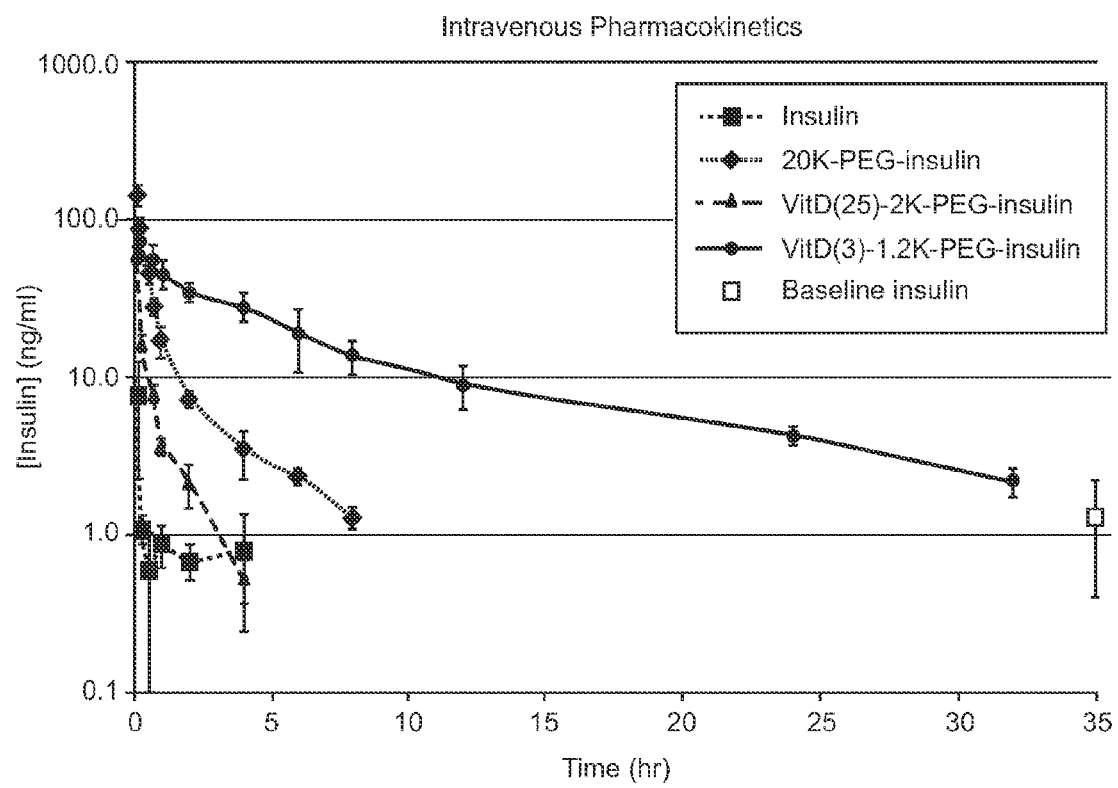

SEQUENCE LISTING

```
<160> NUMBER OF SEQ ID NOS: 8

<210> SEQ ID NO 1
<211> LENGTH: 21
<212> TYPE: PRT
<213> ORGANISM: Homo sapiens

<400> SEQUENCE: 1

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 2
<211> LENGTH: 30
<212> TYPE: PRT
<213> ORGANISM: Homo sapiens

<400> SEQUENCE: 2

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 3
<211> LENGTH: 474
<212> TYPE: PRT
<213> ORGANISM: Homo sapiens

<400> SEQUENCE: 3

Met Lys Arg Val Leu Val Leu Leu Ala Val Ala Phe Gly His Ala
1               5                   10                  15

Leu Glu Arg Gly Arg Asp Tyr Glu Lys Asn Lys Val Cys Lys Glu Phe
            20                  25                  30

Ser His Leu Gly Lys Glu Asp Phe Thr Ser Leu Ser Leu Val Leu Tyr
        35                  40                  45

Ser Arg Lys Phe Pro Ser Gly Thr Phe Glu Gln Val Ser Gln Phe Val
    50                  55                  60

Lys Glu Val Val Ser Phe Thr Glu Ala Cys Cys Ala Glu Gly Ala Asp
65                  70                  75                  80

Pro Asp Cys Tyr Asp Thr Arg Thr Ser Ala Phe Ser Ala Lys Ser Cys
```

```
                        85                  90                  95
Glu Ser Asn Ser Pro Phe Pro Val His Pro Gly Thr Ala Glu Cys Cys
                100                 105                 110
Thr Lys Glu Gly Phe Glu Arg Lys Leu Cys Met Ala Ala Leu Lys His
            115                 120                 125
Gln Pro Gln Glu Phe Pro Thr Tyr Val Glu Pro Thr Asn Asp Glu Ile
        130                 135                 140
Cys Glu Ala Phe Arg Lys Asp Pro Lys Glu Tyr Ala Asn Gln Phe Met
145                 150                 155                 160
Trp Glu Tyr Ser Thr Asn Tyr Gly Gln Ala Pro Leu Ser Leu Leu Val
                165                 170                 175
Ser Tyr Thr Lys Ser Tyr Leu Ser Met Val Gly Ser Cys Cys Thr Ser
                180                 185                 190
Ala Ser Pro Thr Val Cys Phe Leu Lys Glu Arg Leu Gln Leu Lys His
            195                 200                 205
Leu Ser Leu Leu Thr Thr Leu Ser Asn Arg Val Cys Ser Gln Tyr Ala
        210                 215                 220
Ala Tyr Gly Glu Lys Lys Ser Arg Leu Ser Asn Leu Ile Lys Leu Ala
225                 230                 235                 240
Gln Lys Val Pro Thr Ala Asp Leu Glu Asp Val Leu Pro Leu Ala Glu
                245                 250                 255
Asp Ile Thr Asn Ile Leu Ser Lys Cys Cys Glu Ser Ala Ser Glu Asp
                260                 265                 270
Cys Met Ala Lys Glu Leu Pro Glu His Thr Val Lys Leu Cys Asp Asn
            275                 280                 285
Leu Ser Thr Lys Asn Ser Lys Phe Glu Asp Cys Cys Gln Glu Lys Thr
        290                 295                 300
Ala Met Asp Val Phe Val Cys Thr Tyr Phe Met Pro Ala Ala Gln Leu
305                 310                 315                 320
Pro Glu Leu Pro Asp Val Glu Leu Pro Thr Asn Lys Asp Val Cys Asp
                325                 330                 335
Pro Gly Asn Thr Lys Val Met Asp Lys Tyr Thr Phe Glu Leu Ser Arg
                340                 345                 350
Arg Thr His Leu Pro Glu Val Phe Leu Ser Lys Val Leu Glu Pro Thr
            355                 360                 365
Leu Lys Ser Leu Gly Glu Cys Cys Asp Val Glu Asp Ser Thr Thr Cys
        370                 375                 380
Phe Asn Ala Lys Gly Pro Leu Leu Lys Lys Glu Leu Ser Ser Phe Ile
385                 390                 395                 400
Asp Lys Gly Gln Glu Leu Cys Ala Asp Tyr Ser Glu Asn Thr Phe Thr
                405                 410                 415
Glu Tyr Lys Lys Lys Leu Ala Glu Arg Leu Lys Ala Lys Leu Pro Asp
                420                 425                 430
Ala Thr Pro Thr Glu Leu Ala Lys Leu Val Asn Lys His Ser Asp Phe
            435                 440                 445
Ala Ser Asn Cys Cys Ser Ile Asn Ser Pro Pro Leu Tyr Cys Asp Ser
        450                 455                 460
Glu Ile Asp Ala Glu Leu Lys Asn Ile Leu
465                 470

<210> SEQ ID NO 4
<211> LENGTH: 1801
<212> TYPE: DNA
<213> ORGANISM: Homo sapiens
```

-continued

<400> SEQUENCE: 4

```
tttaataata attctgtgtt gcttctgaga ttaataattg attaattcat agtcaggaat      60
ctttgtaaaa aggaaaccaa ttacttttgg ctaccactt tacatggtca cctacaggag      120
agaggaggtg ctgcaagact ctctggtaga aaaatgaaga gggtcctggt actactgctt     180
gctgtggcat ttggacatgc tttagagaga ggccgggatt atgaaaagaa taaagtctgc    240
aaggaattct cccatctggg aaaggaggac ttcacatctc tgtcactagt cctgtacagt    300
agaaaatttc ccagtggcac gtttgaacag gtcagccaac ttgtgaagga agttgtctcc    360
ttgaccgaag cctgctgtgc ggaaggggct gaccctgact gctatgacac caggacctca    420
gcactgtctg ccaagtcctg tgaaagtaat tctccattcc ccgttcaccc aggcactgct    480
gagtgctgca ccaaagaggg cctggaacga aagctctgca tggctgctct gaaacaccag    540
ccacaggaat ccctaccta cgtggaaccc acaaatgatg aaatctgtga ggcgttcagg     600
aaagatccaa aggaatatgc taatcaattt atgtgggaat attccactaa ttacggacaa    660
gctcctctgt cacttttagt cagttacacc aagagttatc tttctatggt agggtcctgc    720
tgtacctctg caagcccaac tgtatgcttt ttgaaagaga gactccagct taaacattta    780
tcacttctca ccactctgtc aaatagagtc tgctcacaat atgctgctta gggagaag     840
aaatcaaggc tcagcaatct cataaagtta gcccaaaaag tgcctactgc tgatctggag    900
gatgttttgc cactagctga agatattact aacatcctct ccaaatgctg tgagtctgcc    960
tctgaagatt gcatggccaa agagctgcct gaacacacag taaaactctg tgacaattta    1020
tccacaaaga attctaagtt tgaagactgt tgtcaagaaa aacagccat ggacgttttt     1080
gtgtgcactt acttcatgcc agctgcccaa ctcccgagc ttccagatgt agagttgccc     1140
acaaacaaag atgtgtgtga tccaggaaac accaaagtca tggataagta tacatttgaa    1200
ctaagcagaa ggactcatct tccggaagta ttcctcagta aggtacttga gccaacccta    1260
aaaagccttg gtgaatgctg tgatgttgaa gactcaacta cctgttttaa tgctaagggc    1320
cctctactaa agaaggaact atcttctttc attgacaagg gacaagaact atgtgcagat    1380
tattcagaaa atacatttac tgagtacaag aaaaaactgg cagagcgact aaaagcaaaa    1440
ttgcctgatg ccacacccac ggaactggca aagctggtta acaagcactc agactttgcc    1500
tccaactgct gttccataaa ctcacctcct ctttactgtg attcagagat tgatgctgaa    1560
ttgaagaata tcctgtagtc ctgaagcatg tttattaact ttgaccagag ttggagccac    1620
ccaggggaat gatctctgat gacctaacct aagcaaaacc actgagcttc tgggaagaca    1680
actaggatac tttctacttt ttctagctac aatatcttca tacaatgaca agtatgatga    1740
tttgctatca aataaattg aaatataatg caaaccataa aaaaaaaaaa aaaaaaaaa     1800
a                                                                    1801
```

<210> SEQ ID NO 5
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 5

Gly Ile Val Glu Gln Cys Cys Thr Ser Ile Cys Ser Leu Tyr Gln Leu
1               5                   10                  15

```
Glu Asn Tyr Cys Gly
            20

<210> SEQ ID NO 6
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Phe Val Asn Gln His Leu Cys Gly Ser His Leu Val Glu Ala Leu Tyr
1               5                   10                  15

Leu Val Cys Gly Glu Arg Gly Phe Phe Tyr Thr Lys Pro Thr
            20                  25                  30

<210> SEQ ID NO 7
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Asp Thr
            20                  25                  30

<210> SEQ ID NO 8
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Lys Lys
            20                  25                  30
```

INSULIN VITAMIN D CONJUGATES

CROSS-REFERENCE TO RELATED APPLICATIONS

This application claims priority to U.S. Provisional Application No. 62/203,385 filed Aug. 10, 2015 and U.S. Provisional Application No. 62/067,398 filed Oct. 22, 2014, the contents of which are incorporated by reference herein in their entirety.

This invention was made with Government support under Grant No. IIP-1430894 awarded by the National Science Foundation, and Grant No. W911NF-14-C-0071 awarded by the Department of Defense. The Government has certain rights in this invention.

SEQUENCE LISTING

The instant application contains a Sequence Listing which has been submitted electronically in ASCII format and is hereby incorporated by reference in its entirety. Said ASCII copy, created on Nov. 5, 2015, is named XTND007US1_SL.txt and is 9,002 bytes in size.

FIELD OF THE INVENTION

The invention provides non-hormonal vitamin D conjugated to insulin peptides that result in the peptides having increased absorption, bioavailability or circulating half-life when compared to non-conjugated forms. The vitamin D targeting groups are coupled to the insulin peptides via the third carbon on the vitamin D backbone.

BACKGROUND OF THE INVENTION

The invention relates to improving the potency, absorption or pharmacokinetic properties of insulin peptides conjugated to certain vitamin D forms. Vitamin D plays a role in calcium, phosphate, and bone homeostasis. The hormonal activity of vitamin D is mediated through binding to the vitamin D receptor (VDR). It enters the nucleus where it binds to the vitamin D receptor element (VDRE) present in the promoters of a subset of genes that are thus responsive to hormonal vitamin D.

Vitamin D is a group of fat-soluble secosteroids. Several forms (vitamers) of vitamin D exist. The two major forms are vitamin D2 or ergocalciferol, and vitamin D3 or cholecalciferol. Vitamin D without a subscript refers to vitamin D2, D3 or other forms known in the art. In humans, vitamin D can be ingested as cholecalciferol (vitamin D3) or ergocalciferol (vitamin D2). The major source of vitamin D for most humans is sunlight. Once vitamin D is made in the skin or ingested, it needs to be activated by a series of hydroxylation steps, first to 25-hydroxyvitamin D (25(OH)D3) in the liver and then to 1,25-dihydroxyvitamin D3 ($1\alpha,25(OH)2D3$) in the kidney. $1\alpha,25(OH)2D3$ is the active "hormonal" form of vitamin D because it binds to VDR. 25(OH)D3 is the "non-hormonal" form of vitamin D and is the major circulating form in the human body. It binds the vitamin D Binding Protein (DBP). It is only converted to the hormonal form as needed. An example of a non-hormonal vitamin D form is one that lacks a $1\alpha$-hydroxyl group. Non-hormonal vitamin D forms have a greatly reduced affinity for VDR and a greatly increased affinity for DBP.

DBP is the principal transporter of vitamin D metabolites (Haddad, J. *Steroid Biochem. Molec. Biol.* (53)579-582 (1995)). Its concentration in the plasma is 6-7 μM and has been detected in all fluid compartments. DBP concentrations exceed the physiological vitamin D metabolite concentrations. DBP is important for the translocation of vitamin D from the skin into circulation, and across cell membranes into the cytoplasm where vitamin D is activated into the hormonal form. The affinity of non-hormonal vitamin D for DBP is significantly higher than the affinity of the hormonal form. In contrast, the affinity of the hormonal form to VDR is significantly more than the non-hormonal form.

Vitamin D and vitamin D analogs have been approved for the treatment of osteoporosis and secondary hyperparathyroidism. Vitamin D has also been shown to inhibit proliferation and induce differentiation in normal as well as cancer cells. The level of vitamin D required for this activity causes severe toxicity in the form of hypercalcemia. Analogs of vitamin D have been approved for the treatment of psoriasis and others are currently being tested for cancer treatment. Many of the analogs discovered to have a reduced calcemic effect contain side-chain modifications (Leyssens et al, Frontiers in Physiology 5: Article 122, 1-18 (2014)). These modifications do not greatly affect VDR binding, and thus, in cell-based proliferation assays, show equal or even increased efficacy. It was shown, however, that many of these modifications reduce binding to DBP and thereby reduce the half-life in the bloodstream.

The addition of poly(ethylene glycol) or (PEG) is a known method of increasing the half-life of some peptides by reducing kidney clearance, reducing aggregation, and diminishing potentially unwanted immune recognition (Jain, Crit. Rev. Ther. Drug Carrier Syst. 25:403-447 (2008)). The PEG is typically used at a considerably large size (20-40 kDa) to maximize the half-life in circulation. This can be accomplished by using either a single large PEG or multiple smaller PEGs attached to the peptide. (Clark et al. J. Biol. Chem. 271:21969-21977 (1996); Fishburn, J. Pharm. Sci. 97:4167-4183 (2008)).

Absorption is a primary focus in drug development and medicinal chemistry because a drug must be absorbed before any medicinal effects can take place. A drug's absorption profile can be affected by many factors. Additionally, the absorption properties of therapeutic peptides vary significantly from peptide to peptide. Some therapeutic peptides are poorly absorbed following dermal administration and cannot be administered orally. Alternate routes of administration such as intravenous, subcutaneous, or intramuscular injections are routinely used for some of peptides; however, these routes often result in slow absorption and exposure of the therapeutic peptides to enzymes that can degrade them, thus requiring much higher doses to achieve efficacy.

A number of peptides have been identified as therapeutically promising. The chemical and biological properties of peptides and proteins make them attractive candidates for use as therapeutics. Peptides and proteins are naturally-occurring molecules made up of amino acids and are involved in numerous physiological processes. Peptides and proteins display a high degree of selectivity and potency, and may not suffer from potential adverse drug-drug interactions or other negative side effects. Thus peptides and proteins hold great promise as a highly diverse, highly potent, and highly selective class of therapeutics with low toxicity. Peptides and proteins, however, may have short in vivo half-lives. For such peptides, this may be a few minutes. This may render them generally impractical, in their native form (also referred to as "wild", "wild type" or "wt" herein), for therapeutic administration. Additionally, peptides may have a short duration of action or poor bioavailability.

Insulin is a peptide hormone produced by beta cells in the pancreas that regulates the metabolism of carbohydrates and fats (SEQ ID NO:1 and 2). The human insulin protein is composed of 51 amino acids, and has a molecular weight of 5808 Daltons. It is a dimer of an A-chain and a B-chain that are linked by disulfide bonds. It promotes the absorption of glucose from the blood to skeletal muscles and fat tissue and causes fat to be stored rather than used for energy. In some preferred embodiments, insulin derivatives are conjugated to the carriers of the invention. In more preferred embodiments, the A-chain is modified at residue 21 where the asparagine is replaced with a glycine. In other preferred embodiments, the B-chain is modified at position 3 (the asparagine is replaced with a lysine), position 28 (proline is replaced with aspartic acid), positions 28 and 29 (the proline and lysine are swapped), position 29 (lysine is replaced with aspartic acid), or at the carboxyl terminus (addition of residues that may include 1, 2, or more arginine residues).

Under normal physiological conditions, insulin is produced at a constant proportion to remove excess glucose from the blood. When control of insulin levels fails, however, diabetes mellitus can result. Thus, diabetic patients often receive injected insulin. Patients with type 1 diabetes depend on external insulin for their survival because the hormone is no longer sufficiently produced internally. Insulin is most commonly injected subcutaneously. Patients with type 2 diabetes are often insulin resistant and may suffer from an "apparent" insulin deficiency.

SUMMARY OF THE INVENTION

The invention provides carrier-drug conjugates comprising a targeting group that is non-hormonal vitamin D, an analog, or metabolite thereof linked at the carbon 3 position to insulin. In some embodiments, the non-hormonal vitamin D molecules are not hydroxylated at the carbon 1 position. The carriers enhance the absorption, stability, half-life, duration of effect, potency, or bioavailability of insulin. Optionally, the carriers further comprise scaffolding moieties that are non-releasable such as PEG and others described in this disclosure.

Thus, the invention provides a carrier-drug conjugate comprising a targeting group that is a non-hormonal vitamin D, analog, or metabolite thereof conjugated to an insulin peptide at the carbon 3 position of the non-hormonal vitamin D targeting group. In a preferred embodiment, the non-hormonal vitamin D is not hydroxylated at the carbon 1 position. In another preferred embodiment, the targeting group is conjugated to the insulin peptide via a scaffold that is selected from the group consisting of poly(ethylene glycol), polylysine, polyethyleneimine, poly(propyleneglycol), a peptide, serum albumin, thioredoxin, an immunoglobulin, an amino acid, a nucleic acid, a glycan, a modifying group that contains a reactive linker, a water-soluble polymer, a small carbon chain linker, and an additional therapeutic peptide.

The invention provides a pharmaceutical composition comprising a carrier-drug conjugate comprising a targeting group that is a non-hormonal vitamin D, analog, or metabolite thereof conjugated via a scaffold at the carbon 3 position to an insulin peptide having an amino acid sequence with at least a 90% sequence identity to SEQ ID NO:1, 2, or 5-8. In a preferred embodiment, the carrier increases the absorption, bioavailability, or half-life of said insulin peptide in circulation. In another preferred embodiment, the non-hormonal vitamin D is not hydroxylated at the carbon 1 position.

In another embodiment, the scaffold is selected from the group consisting of poly(ethylene glycol), polylysine, polyethyleneimine, poly(propyleneglycol), a peptide, serum albumin, thioredoxin, an immunoglobulin, an amino acid, a nucleic acid, a glycan, a modifying group that contains a reactive linker, a water-soluble polymer, a small carbon chain linker, and an additional therapeutic peptide. In a most preferred embodiment, the scaffold is poly(ethylene glycol).

The invention provides a method of treating a patient in need of an insulin peptide, comprising administering an effective amount of any of the pharmaceutical compositions described herein. In a preferred embodiment, the pharmaceutical composition is delivered to said patient by a transdermal, oral, parenteral, subcutaneous, intracutaneous, intravenous, intramuscular, intraarticular, intrasynovial, intrasternal, intrathecal, intralesional, intracranial injection, infusion, inhalation, ocular, topical, rectal, nasal, buccal, sublingual, vaginal, or implanted reservoir mode.

The invention provides the use of any of the pharmaceutical compositions described herein for the manufacture of a medicament for the treatment of a patient in need of said medicament.

The invention provides a method of manufacturing any of the pharmaceutical compositions described herein comprising conjugating a targeting group and an insulin peptide, wherein the conjugating step utilizes a coupling group. In some embodiments, the coupling group is selected from the group consisting of an amine-reactive group, a thiol-reactive group, a maleimide group, a thiol group, an aldehyde group, an NHS-ester group, a haloacetyl group, an iodoacetyl group, a bromoacetyl groups, a SMCC group, a sulfo SMCC group, a carbodiimide group, bifunctional cross-linkers, NHS-maleimido, and combinations thereof. In other embodiments, the invention provides pharmaceutical compositions resulting from the method described herein, wherein the compositions comprise a carrier-drug compound containing a linkage selected from the group consisting of a thiol linkage, an amide linkage, an oxime linkage, a hydrazone linkage, and a thiazolidinone linkage. In another embodiment, the conjugating step is accomplished by cycloaddition reactions.

The invention provides a pharmaceutical carrier comprising a formula I:

$$B\text{-}(L)^a\text{-}S\text{-}(M)^b\text{-}C \quad \quad I$$

Wherein:

B is a targeting group that is a non-hormonal vitamin D, analog, or metabolite thereof conjugated at the carbon 3 position to $L^1$;

S is a scaffold moiety, comprising poly(ethylene glycol), polylysine, polyethyleneimine, poly(propyleneglycol), a peptide, serum albumin, thioredoxin, an immunoglobulin, an amino acid, a nucleic acid, a glycan, a modifying group that contains a reactive linker, polylactic acid, a water-soluble polymer, a small carbon chain linker, or an additional therapeutic moiety;

C is an amine-reactive group, a thiol-reactive group, a maleimide group, a thiol group, a disulfide group, an aldehyde group, an NHS-ester group, a 4-nitrophenyl ester, an acylimidazole, a haloacetyl group, an iodoacetyl group, a bromoacetyl groups, a SMCC group, a sulfo SMCC group, a carbodiimide group and bifunctional cross-linkers such as NHS-Maleimido or combinations thereof;

$L^1$ and $L^2$ are linkers independently selected from —$(CH_2)_n$—, —C(O)NH—, —HNC(O)—, —C(O)O—, —OC(O)—, —O—, —S—S—, —S—, —S(O)—, —$S(O)_2$— and —NH—;

$L^3$ is —$(CH_2)_o$—;

n is an integer from 0-3; and o is an integer from 0-3.

In a preferred embodiment, the pharmaceutical carrier comprises formula V:

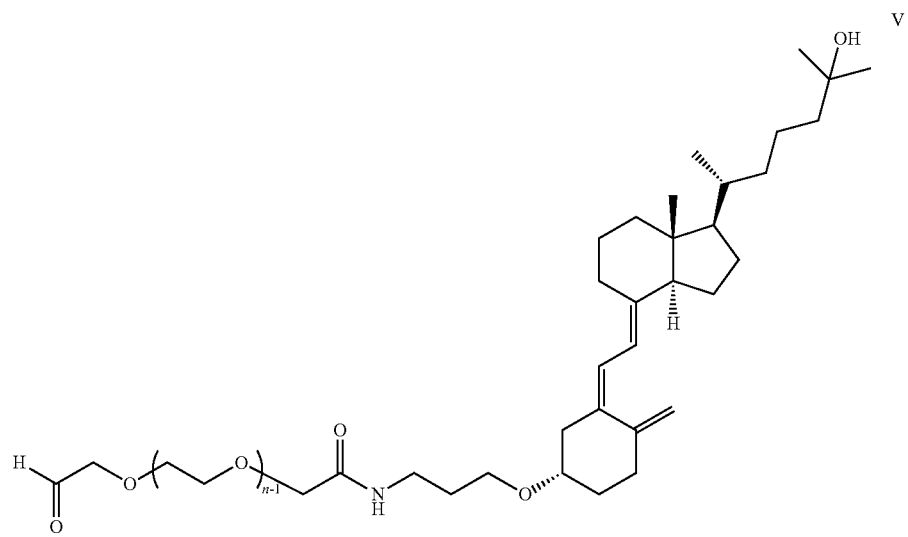

In another preferred embodiment, the pharmaceutical carrier comprises formula VI:

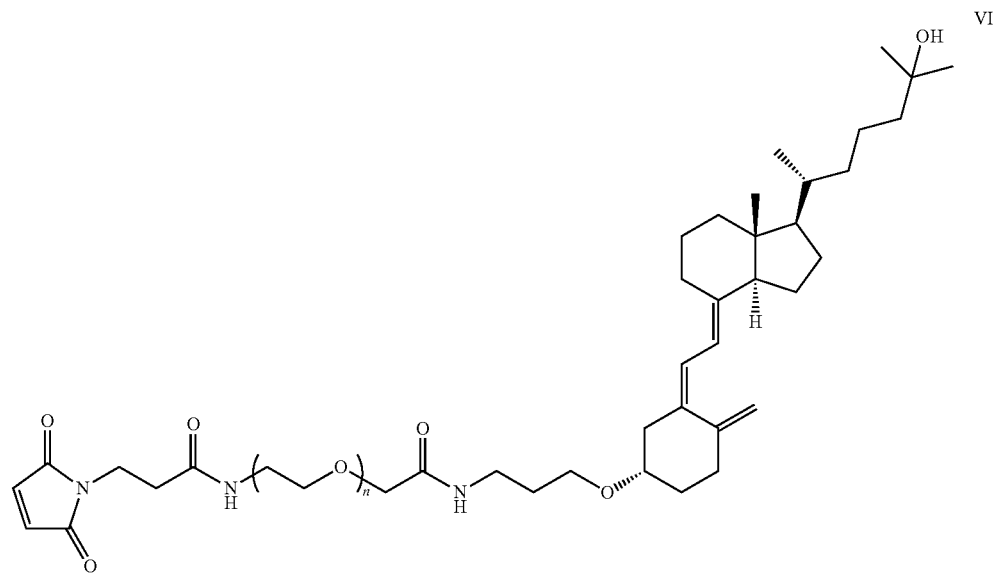

In another preferred embodiment, the pharmaceutical carrier comprises formula VII:

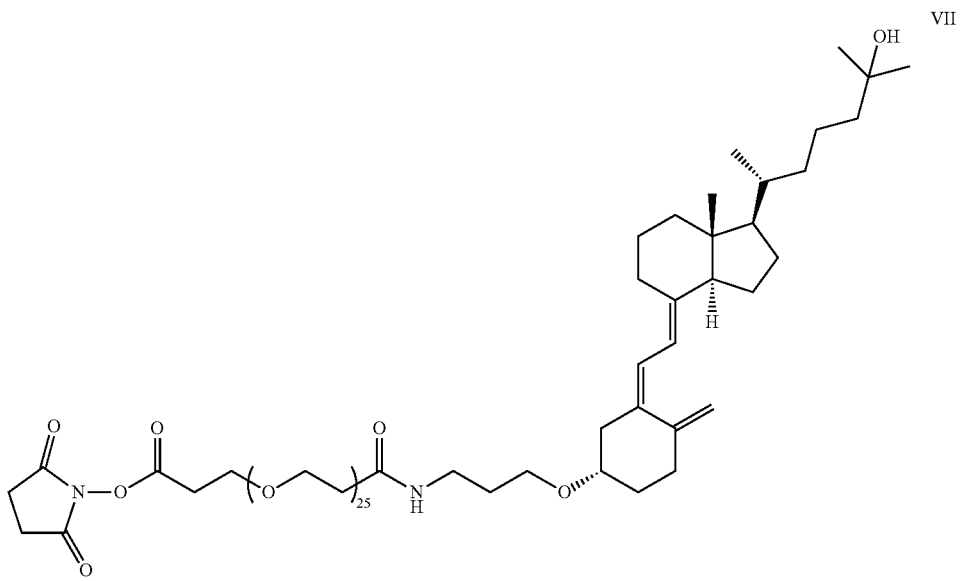

The invention provides a pharmaceutical composition, comprising an insulin peptide, a stably attached scaffold, a targeting group that is a non-hormonal vitamin D, analog, or metabolite thereof conjugated at the carbon 3 position, wherein after administration to a first test subject, the insulin peptide has a half-life measured by ELISA or other analyses of blood samples taken at a plurality of time points that is greater than a half-life of said insulin peptide administered to a second test subject without said stably attached scaffold moiety and targeting group as measured by the ELISA or other analyses of blood samples taken at said plurality of time points. In a preferred embodiment, the administration to said first and second subjects is accomplished by subcutaneous injection.

In another preferred embodiment, the insulin peptide stably attached to the scaffold and targeting group retains substantially the same activity as the insulin peptide not stably attached to said scaffold and targeting group as measured by a functional assay.

In another embodiment, a scaffold mass range is selected from the group consisting of about 100 Da. to 20,000 Da., 200 Da. to 15,000 Da., 300 Da. to 10,000 Da., 400 Da. to 9,000 Da., 500 Da. to 5,000 Da., 600 Da. to 2,000 Da., 1000 Da. to 200,000 Da., 20.00 Da. to 200,000 Da., 100,000 to 200,000 Da., 5000 Da. to 100,000 Da., 10,000 Da. to 80,000 Da., 20,000 Da. to 60,000 Da., and 20,000 Da. to 40,000 Da. In preferred embodiments, the scaffold mass is about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0 KDa. In another preferred embodiment, the scaffold is approximately the same mass as the insulin peptide.

The invention provides a carrier-drug conjugate comprising a targeting group that is vitamin D, an analog, or a metabolite thereof non-releasably conjugated to an insulin peptide. In a preferred embodiment, the vitamin D is non-hormonal. In a more preferred embodiment, the non-hormonal vitamin D is not hydroxylated at the carbon 1 position. In another preferred embodiment, the insulin peptide is conjugated at the carbon 3 position of said non-hormonal vitamin D targeting group. In another preferred embodiment, the insulin peptide retains substantially the same activity as said insulin peptide not conjugated to said targeting group as measured by a functional assay. In another preferred embodiment, the targeting group is conjugated to the insulin peptide via a scaffold that is selected from the group consisting of poly(ethylene glycol), polylysine, polyethyleneimine, poly(propyleneglycol), a peptide, serum albumin, thioredoxin, an immunoglobulin, an amino acid, a nucleic acid, a glycan, a modifying group that contains a reactive linker, a water-soluble polymer, a small carbon chain linker, and an additional therapeutic peptide. In a more preferred embodiment, the scaffold is approximately the same mass as the insulin peptide.

BRIEF DESCRIPTION OF THE DRAWINGS

FIG. 2: Reaction scheme showing the chemical structure and syntheses used to generate a carrier, a vitamin D-(3)-PEG$_{2k}$-maleimide adduct. The carrier was generated by conjugating 1) a vitamin D analog, 2) a PEG scaffold, and 3) a maleimide coupling group.

FIG. 4: Determination of the bioactivity of insulin conjugates compared to unconjugated insulin at the insulin receptor, isoform B (INSRb).

FIGS. 5A-5B: Determination of the pharmacokinetics of insulin conjugates compared to unconjugated insulin upon intravenous (FIG. 5A) and subcutaneous (FIG. 5B) injection.

DETAILED DESCRIPTION OF THE INVENTION

Figure 1:
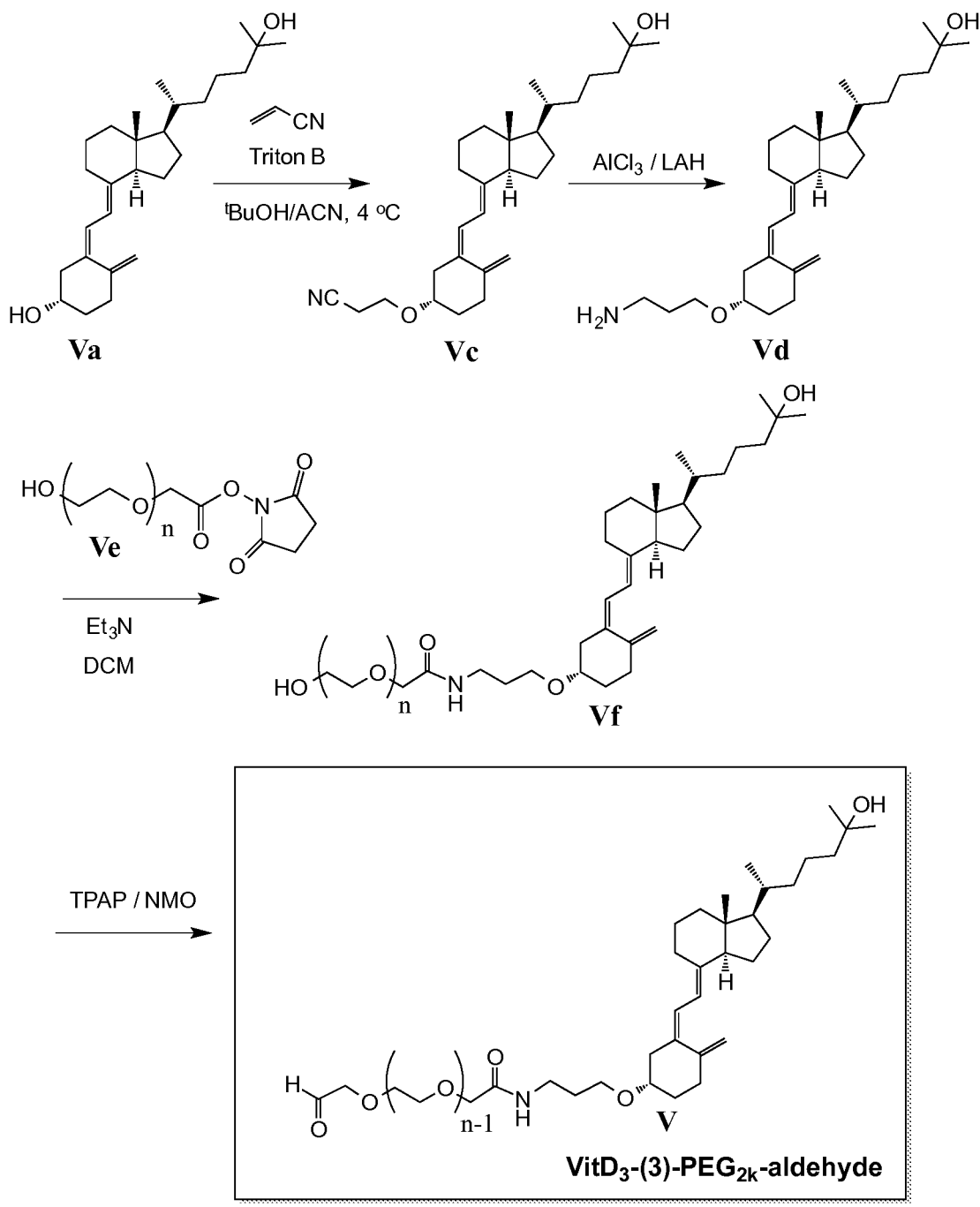
FIG. 1: Reaction scheme showing the chemical structure and syntheses used to generate a carrier, a vitamin D-(3)-PEG$_{2k}$-aldehyde adduct. The carrier was generated by conjugating 1) a vitamin D analog, 2) a PEG scaffold, and 3) an aldehyde coupling group.

The invention provides carrier-insulin conjugates comprising targeting groups that are non-hormonal vitamin D, vitamin D analogs, or vitamin D metabolites. Examples include vitamin D-based molecules that are not hydroxylated at the carbon 1 (C1) position. The carriers are linked to insulin peptides at the carbon 3 (C3) position. As disclosed herein, carrier groups are surprisingly effective when non-hormonal vitamin D forms are used and the insulin peptide is linked to the carbon 3 position. While not wishing to be bound by theory, it is believed that the hormonal forms of vitamin D are not appropriate for the carriers described herein because they can be toxic due to the induction of hypercalcemia. Also, because the hormonal forms bind the vitamin D receptor in cells, they may improperly target the carrier-drug conjugates to undesired cells or tissues. In contrast, non-hormonal vitamin D forms bind the Vitamin D Binding Protein (DBP) and remain in circulation longer.

The carrier molecules are attached to the insulin peptides using chemistries described herein, described in WO2013172967, incorporated herein in its entirety, or that are otherwise known in the art. The carriers improve the potency, absorption, bioavailability, circulating half-life or pharmacokinetic properties of the insulin peptides. In certain embodiments, the carriers further comprise what will be described herein as a "scaffold" that acts, among other things, as a non-releasable "spacer" between the targeting group and the insulin peptide. In other embodiments, the carriers lack a scaffold.

The carriers are designed to be suitable for use in humans and animals. The carriers serve the purpose of improving the pharmacokinetic properties of a biological or chemical entity that is coupled, conjugated, or fused to the carrier. This occurs through the interaction of the targeting group with DBP. DBP can actively transport molecules quickly and effectively from the site of administration to the circulating plasma, thereby reducing exposure of the drug to degradative enzymes. The carriers, by binding to DBP, also improve the circulating half-life of the drug. This increases the potency and therapeutic efficacy of the drug by preventing kidney filtration and other elimination processes.

In describing and claiming one or more embodiments of the present invention, the following terminology will be used in accordance with the definitions described below.

The term "absorption" is the movement of a drug into the bloodstream. A drug needs to be introduced via some route of administration (e.g. oral, topical dermal, subcutaneous, intramuscular, or intravenous) or in a specific dosage form such as a tablet, capsule, patch, suspension, emulsion, or liquid.

The term "bioavailability" refers to the fraction of an administered dose of unchanged drug that reaches the systemic circulation, one of the principal pharmacokinetic properties of drugs. When a medication is administered intravenously, its bioavailability is 100%. When a medication is administered via other routes (such as orally), its bioavailability generally decreases (due to incomplete absorption and first-pass metabolism) or may vary from patient to patient. Bioavailability is an important parameter in pharmacokinetics that is considered when calculating dosages for non-intravenous routes of administration.

"Carriers" are compounds that can be conjugated to, fused to, coupled to or formulated with insulin peptides to improve the absorption, half-life, bioavailability, pharmacokinetic or pharmacodynamic properties of the drugs. They comprise a targeting group, a coupling group, and optionally, a scaffold moiety. In some embodiments, carriers may carry insulin peptides from the site of subcutaneous injection into circulation as well as carry the insulin peptides in circulation for an extended period of time.

An "effective amount" refers to an amount of insulin peptide that is effective, at dosages and for periods of time necessary, to achieve the desired therapeutic or prophylactic result. A "therapeutically effective amount" of an insulin peptide may vary according to factors such as the disease state, age, sex, and weight of the individual. A therapeutically effective amount may be measured, for example, by improved survival rate, more rapid recovery, or amelioration, improvement or elimination of symptoms, or other acceptable biomarkers or surrogate markers. A therapeutically effective amount is also one in which any toxic or detrimental effects of the insulin peptide are outweighed by the therapeutically beneficial effects. A "prophylactically effective amount" refers to an amount of insulin peptide that is effective, at dosages and for periods of time necessary, to achieve the desired prophylactic result. Typically, but not necessarily, since a prophylactic dose is used in subjects prior to or at an earlier stage of disease, the prophylactically effective amount will be less than the therapeutically effective amount.

"Half-life" is a scientific term known in the art that refers to the amount of time that elapses when half of the quantity of a test molecule is no longer detected. An in vivo half-life refers to the time elapsed when half of the test molecule is no longer detectable in circulating serum or tissues of a human or animal.

A "hormone" is a biological or chemical messenger that communicates between one cell (or group of cells) to another cell. As described herein, hormones for use in the invention may be peptides, steroids, pheromones, interleukins, lymphokines, cytokines, or members of other hormone classes known in the art.

"Homologs" are bioactive molecules that are similar to a reference molecule at the nucleotide sequence, peptide sequence, functional, or structural level. Homologs may include sequence derivatives that share a certain percent identity with the reference sequence. Thus, in one embodiment, homologous or derivative sequences share at least a 70 percent sequence identity. In a preferred embodiment, homologous or derivative sequences share at least an 80 or 85 percent sequence identity. In a more preferred embodiment, homologous or derivative sequences share at least an 86, 87, 88, 89, 90, 91, 92, 93, 94, 95, 96, 97, 98, or 99 percent sequence identity. Homologous or derivative nucleic acid sequences may also be defined by their ability to remain bound to a reference nucleic acid sequence under high stringency hybridization conditions. Homologs having a structural or functional similarity to a reference molecule may be chemical derivatives of the reference molecule. Methods of detecting, generating, and screening for structural and functional homologs as well as derivatives are known in the art.

"Hybridization" generally depends on the ability of denatured DNA to reanneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so. For additional details and explanation of stringency of hybridization reactions, see Ausubel et al, Current Protocols in Molecular Biology, Wiley Interscience Publishers (1995).

An "individual," "subject" or "patient" is a vertebrate. In certain embodiments, the vertebrate is a mammal. Mammals include, but are not limited to, primates (including human and non-human primates) and rodents (e.g., mice, hamsters, guinea pigs, and rats). In certain embodiments, a mammal is a human. A "control subject" refers to a healthy subject who has not been diagnosed as having a disease, dysfunction, or condition that has been identified in an individual, subject, or patient. A control subject does not suffer from any sign or symptom associated with the disease, dysfunction, or condition.

A "medicament" is an active drug that has been manufactured for the treatment of a disease, disorder, or condition.

"Nucleic acids" are any of a group of macromolecules, either DNA, RNA, or variants thereof, that carry genetic information that may direct cellular functions.

"Patient response" or "response" can be assessed using any endpoint indicating a benefit to the patient, including, without limitation, (1) inhibition, to some extent, of disease progression, including slowing down and complete arrest; (2) reduction in the number of disease episodes and/or symptoms; (3) inhibition (i.e., reduction, slowing down or complete stopping) of a disease cell infiltration into adjacent peripheral organs and/or tissues; (4) inhibition (i.e. reduction, slowing down or complete stopping) of disease spread; (5) decrease of an autoimmune condition; (6) favorable change in the expression of a biomarker associated with the disorder; (7) relief, to some extent, of one or more symptoms associated with a disorder; (8) increase in the length of disease-free presentation following treatment; or (9) decreased mortality at a given point of time following treatment.

As used herein, the term "peptide" is any peptide comprising two or more amino acids. The term peptide includes short peptides (e.g., peptides comprising between 2-14 amino acids), medium length peptides (15-50) or long chain peptides (e.g., proteins). The terms peptide, medium length peptide and protein may be used interchangeably herein. As used herein, the term "peptide" is interpreted to mean a polymer composed of amino acid residues, related naturally occurring structural variants, and synthetic non-naturally occurring analogs thereof linked via peptide bonds, related naturally-occurring structural variants, and synthetic non-naturally occurring analogs thereof. Synthetic peptides can be synthesized, for example, using an automated peptide synthesizer. Peptides can also be synthesized by other means such as by cells, bacteria, yeast or other living organisms. Peptides may contain amino acids other than the 20 gene-encoded amino acids. Peptides include those modified either by natural processes, such as processing and other post-translational modifications, but also by chemical modification techniques. Such modifications are well described in basic texts and in more detailed monographs, and are well-known to those of skill in the art. Modifications occur anywhere in a peptide, including the peptide backbone, the amino acid side chains, and the amino or carboxyl termini.

As used herein, a "pharmaceutically acceptable carrier" or "therapeutic effective carrier" is aqueous or nonaqueous (solid), for example alcoholic or oleaginous, or a mixture thereof, and can contain a surfactant, emollient, lubricant, stabilizer, dye, perfume, preservative, acid or base for adjustment of pH, a solvent, emulsifier, gelling agent, moisturizer, stabilizer, wetting agent, time release agent, humectant, or other component commonly included in a particular form of pharmaceutical composition. Pharmaceutically acceptable carriers are well known in the art and include, for example, aqueous solutions such as water or physiologically buffered saline or other solvents or vehicles such as glycols, glycerol, and oils such as olive oil or injectable organic esters. A pharmaceutically acceptable carrier can contain physiologically acceptable compounds that act, for example, to stabilize or to increase the absorption of specific inhibitor, for example, carbohydrates, such as glucose, sucrose or dextrans, antioxidants such as ascorbic acid or glutathione, chelating agents, low molecular weight proteins or other stabilizers or excipients.

The term "pharmacokinetics" is defined as the time course of the absorption, distribution, metabolism, and excretion of an insulin peptide. Improved "pharmacokinetic properties" are defined as: improving one or more of the pharmacokinetic properties as desired for a particular therapeutic peptide. Examples include but are not limited to: reducing elimination through metabolism or secretion, increasing drug absorption, increasing half-life, and/or increasing bioavailability.

"Scaffolds" are molecules to which other molecules can be covalently or non-covalently attached or formulated. The scaffolds of the invention may act as "spacers" between the targeting group and the drug. Spacers are molecular entities that provide physical distance between the two distinct molecular entities. Scaffolds may also contain a reactive "linker" or may have beneficial therapeutic properties in addition to the drug. Linkers are the sites of attachment from one molecular entity to another. Thus, the scaffolds of the invention may be, for example, PEG; serum albumin, thioredoxin, an immunoglobulin, a modifying group that contains a reactive linker, a water-soluble polymer, or a therapeutic compound. The scaffolds and linkers of the invention are stable (i.e. non-releasable). Non-releasable linkers have more stable chemical bonds than releasable linkers to allow the attached molecular entities to remain attached in vivo. In certain embodiments, however, they may be "releasable" under specific conditions. Releasable linkers have inherent instability and allow for the release of the attached molecules under certain conditions over time.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures.

"Stringent conditions" or "high stringency conditions", as defined herein, can be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) overnight hybridization in a solution that employs 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µl/ml), 0.1% SDS, and 10% dextran sulfate at 42° C., with a 10 minute wash at 42° C. in 0.2×SSC (sodium chloride/sodium citrate) followed by a 10 minute high-stringency wash consisting of 0.1×SSC containing EDTA at 55° C.

As used herein, "treatment" refers to clinical intervention in an attempt to alter the natural course of the individual or cell being treated, and can be performed before or during the course of clinical pathology. Desirable effects of treatment include preventing the occurrence or recurrence of a disease or a condition or symptom thereof, alleviating a condition or symptom of the disease, diminishing any direct or indirect pathological consequences of the disease, decreasing the rate of disease progression, ameliorating or palliating the disease state, and achieving remission or improved prognosis. In some embodiments, methods and compositions of the invention are useful in attempts to delay development of a disease or disorder.

A "vitamin" is a recognized term in the art and is defined as a fat-soluble or water-soluble organic substance essential in minute amounts for normal growth and activity of the body and is obtained naturally from plant and animal foods or supplements.

"Vitamin D" is a group of fat-soluble secosteroids. Several forms (vitamers) of vitamin D exist. The two major forms are vitamin D2 or ergocalciferol, and vitamin D3 or cholecalciferol. Vitamin D without a subscript refers to vitamin D2, D3 or other forms known in the art. In humans, vitamin D can be ingested as cholecalciferol (vitamin D3) or ergocalciferol (vitamin D2). Additionally, humans can synthesize it from cholesterol when sun exposure is adequate. Cholecalciferol may be modified in the liver or in vitro to 25-hydroxycholecalciferol ("25-hydroxy vitamin D"). In the kidney or in vitro, 25-hydroxy vitamin D can be modified into the distinct hormonal form of 1, 25-hydroxy vitamin D.

"Vitamin D binding protein" or "DBP" is a naturally circulating serum protein found in all mammals that, among other activities, can bind to and transport vitamin D and its analogs to sites in the liver and kidney where the vitamin is modified to its active form, and it retains vitamin D in its various forms in circulation for, on average, 30 days in humans. A DBP protein sequence is disclosed in SEQ ID NO:3 and an exemplary nucleic acid sequence encoding the DBP protein sequence is disclosed in SEQ ID NO:4. DBP has multiple naturally-occurring isoforms. Exemplary isoforms are available in the public sequence databases (e.g. Accession Nos. NM_001204306.1, NM_001204307.1, NM_000583.3, BCO36003.1, M12654.1, X03178.1, AK223458, P_001191235.1, NP_000574.2, AAA61704.1, AAD13872.1, NP_001191236.1, AAA19662.2, 154269, P02774.1, EAX05645.1, AAH57228.1, AAA52173.1, AAB29423.1, AAD14249.1, AAD14250.1, and BAD97178.1).

The invention contemplates non-hormonal vitamin D conjugates that bind DBP or functional DBP variants and homologs that contain conservative or non-conservative amino acid substitutions that substantially retain DBP activity. DBP binding molecules or functional DBP variants may be identified using known techniques and characterized using known methods (Bouillon et al., *J. Bone Miner Res.* 6(10):1051-7 (1991), Teegarden et. al., *Anal. Biochemistry* 199(2):293-299 (1991), McLeod et al, *J. Biol Chem.* 264 (2):1260-7 (1989), Revelle et al., *J. Steroid Biochem.* 22:469-474 (1985)). The foregoing references are incorporated by reference herein in their entirety.

The term "water-soluble" refers to moieties that have some detectable degree of solubility in water. Methods to detect and/or quantify water solubility are well known in the art. Exemplary water-soluble polymers include peptides, saccharides, poly(ethers), poly(amines), poly(carboxylic acids) and the like.

The invention provides effective routes for administering insulin. In preferred embodiments, the invention provides effective routes of drug administration via transdermal, oral, parenteral, subcutaneous, intracutaneous, intravenous, intramuscular, intraarticular, intrasynovial, intrasternal, intrathecal, intralesional, intracranial injection, infusion, inhalation, ocular, topical, rectal, nasal, buccal, sublingual, vaginal, or implanted reservoir modes. The preferred route of administration is via subcutaneous injection.

In addition, the inventions described herein provide compositions and methods for maintaining target binding activity, i.e. pharmacodynamics (PD), for insulin peptides. It further provides compositions and methods for improving the pharmacokinetic (PK) profiles of insulin peptides as described herein. The invention further provides compositions and methods for improved drug absorption profiles as compared to the drug absorption profiles for the drugs using the same routes of administration or different routes of administration but without the inventions described herein. The invention further provides compositions and methods for improved drug bioavailability profiles as compared to the drug bioavailability profiles for the drugs using the same routes of administration or different routes of administration but without the carriers described herein. The invention further provides compositions and methods for improved drug half-life profiles as compared to the drug half-life profiles for the drugs using the same routes of administration or different routes of administration but without the inventions described herein.

The non-hormonal vitamin D carriers disclosed herein may improve the absorption, half-life, bioavailability, or pharmacokinetic properties of the linked insulin peptides. While not wishing to be bound by theory, the carriers have the properties of binding to the body's natural DBP. DBP may transport the carrier-drug complex from the site of administration to the circulating serum. The vitamin D-DBP interaction may retain the insulin peptides in circulation for an extended period of time. This can prevent its excretion from the body and increase the exposure of the insulin peptide in the body to achieve a longer lasting therapeutic effect. Additionally, a smaller dose of drug may be required when conjugated the carrier when compared to the unmodified form.

The insulin peptide carrier conjugates of the invention typically have about 1, 2, 3, 4, 5, 6, 7, 8, 9, or 10 targeting groups individually attached to an insulin peptide. The structure of each of the targeting groups attached to the insulin peptide may be the same or different. In preferred embodiments, one or more targeting groups are stably or non-releasably attached to the insulin peptide at the N-terminus, C-terminus, or other portion of an insulin peptide. For example, an insulin peptide carrier conjugate may comprise a targeting group attached to the N-terminus and additionally a targeting group attached to a lysine residue. In another embodiment, an insulin peptide carrier conjugate has a targeting group attached to an insulin peptide via a modification such as a sugar residue as part of a glycosylation site, or on an acylation site of a peptide or attached to a phosphorylation site or other natural or non-natural modifications that are familiar to one skilled in the art. Also contemplated are attachment sites using a combination of sites mentioned above. One preferred embodiment of the present invention comprises a targeting group that is attached to the insulin peptide at one specific site on the peptide. In another preferred embodiment, the attachment site on a protein may be a cysteine, lysine, the N-terminus or C-terminus.

In another embodiment, the scaffold is a pharmaceutically acceptable carrier. In preferred embodiments, the scaffold is poly(ethylene glycol), polylysine, polyethyleneimine, poly (propyleneglycol), a peptide, serum albumin, thioredoxin, an immunoglobulin, an amino acid, a nucleic acid, a glycan, a modifying group that contain a reactive linker, a water-soluble polymer, a small carbon chain linker, or an additional therapeutic moiety.

In one embodiment, water-soluble scaffold moieties have some detectable degree of solubility in water. Methods to detect and/or quantify water solubility are well known in the art. Exemplary water-soluble polymers include peptides, saccharides, poly(ethers), poly(amines), poly(carboxylic acids) and the like.

Peptides can have mixed sequences or be composed of a single amino acid, e.g., poly(lysine). An exemplary polysaccharide is poly(sialic acid). An exemplary poly(ether) is poly(ethylene glycol), e.g. m-PEG □Poly(ethyleneimine) is an exemplary polyamine, and poly(acrylic) acid is a representative poly(carboxylic acid). The polymer backbone of the water-soluble polymer can be poly(ethylene glycol) (i.e. PEG). However, it should be understood that other related polymers are also suitable for use in the practice of this invention and that the use of the term PEG or poly(ethylene glycol) is intended to be inclusive and not exclusive in this respect. The term PEG includes poly(ethylene glycol) in any of its forms, including alkoxy PEG difunctional PEG multiarmed PEG forked PEG branched PEG; pendent PEG (i.e. PEG or related polymers having one or more functional groups pendent to the polymer backbone), or PEG with degradable linkages therein. The polymer backbone can be linear or branched.

Branched polymer backbones are generally known in the art. Typically, a branched polymer has a central branch core moiety and a plurality of linear polymer chains linked to the central branch core. PEG is commonly used in branched forms that can be prepared by addition of ethylene oxide to various polyols, such as glycerol, pentaerythritol and sorbitol. The central branch moiety can also be derived from several amino acids, such as lysine. The branched poly (ethylene glycol) can be represented in general form as R(-PEG-OH)m in which R represents the core moiety, such as glycerol or pentaerythritol, and m represents the number of arms. Multi-armed PEG molecules, such as those described in U.S. Pat. No. 5,932,462, which is incorporated by reference herein in its entirety, can also be used as the polymer backbone.

Many other polymers are also suitable for the invention. Polymer backbones that are non-peptidic and water-soluble, with from 2 to about 300 termini, are particularly useful in the invention. Examples of suitable polymers include, but are not limited to, other poly(alkylene glycols), such as poly(propylene glycol) ("PPG"), copolymers of ethylene glycol and propylene glycol and the like, poly(oxyethylated polyol), poly(olefinic alcohol), polyvinylpyrrolidone), polylysine, polyethyleneimine, poly(hydroxypropylmethacrylamide), poly(α-hydroxy acid), poly(vinyl alcohol), polyphosphazene, polyoxazoline, poly(N-acryloylmorpholine), such as described in U.S. Pat. No. 5,629,384, which is incorporated by reference herein in its entirety, and copolymers, terpolymers, and mixtures thereof. Although the molecular weight of each chain of the polymer backbone can vary, it is typically in the range of about 100 Da to about 100,000 Da.

In other embodiments, the scaffold moiety may be a peptide, serum albumin, thioredoxin, an immunoglobulin, an amino acid, a nucleic acid, a glycan, a modifying group that contains a reactive linker, a water-soluble polymer, a small carbon chain linker, or an additional therapeutic peptide. In one embodiment, the scaffold moieties are non-toxic to humans and animals. In another embodiment, the scaffolds are endogenous serum proteins. In another embodiment, the scaffold moieties are water-soluble polymers. In another embodiment, the scaffolds are non-naturally-occurring polymers. In another embodiment, the scaffolds are naturally-occurring moieties that are modified by covalent attachment to additional moieties (e.g., PEG; poly (propylene glycol), poly(aspartate), biomolecules, therapeutic moieties, or diagnostic moieties). The scaffolds and linkers of the invention are stable (i.e. non-releasable). In certain embodiments, however, they may be "releasable" under specific conditions.

The conjugation of hydrophilic polymers, such as PEG; is known in the art. In its most common form, PEG is a linear polymer terminated at each end with hydroxyl groups: HO—CH2CH2O—(CH2CH2O)n-CH2CH2-OH where n typically ranges from about 3 to about 4000. In a preferred embodiment, the PEG has a molecular weight distribution that is essentially homodisperse. In another preferred embodiment, the PEG is a linear polymer. In another preferred embodiment the PEG is a branched polymer.

Many end-functionalized or branched derivatives and various sizes are known in the art and commercially available. By way of example, conjugation of the PEG or PEO may be carried out using the compositions and methods described herein and in U.S. Pat. No. 7,803,777 (Defrees et al.) and U.S. Pat. No. 4,179,337 (Davis et al.), each of which are incorporated by reference herein in their entirety.

In some embodiments, smaller therapeutic peptides such as insulin are paired with smaller scaffold moieties. It is contemplated, however, that insulin could be paired with a larger scaffold moiety. In some embodiments, a scaffold that is approximately equal to or smaller than the molecular weight of insulin results in an efficacious carrier-drug conjugate. Improvements in efficacy may be obtained by empirically adjusting the scaffold size further. Without wishing to be bound by theory, the pharmacokinetic properties and efficacy of the conjugates may be enhanced when a scaffold (in combination with linkers as needed) is big enough to ablate potential steric hindrance of the drug by DBP binding and vice versa. Thus, an insulin peptide is conjugated so that its active region is exposed and available for functional activity and the carrier is able to bind DBP. Additional embodiments provide non-releasable attachments that extend the circulation of insulin peptides. In some embodiments, the scaffold may be selected to be approximately equal to the peptide's molecular weight.

In preferred embodiments, the conjugation of the insulin peptide retains substantially all of its activity following the conjugation. The active region of insulin is known in the art. In other embodiments, the insulin peptide is therapeutically active while remaining linked to the carrier. This embodiment may maximize the time in circulation and as well as its efficacy.

The scaffolds of the present invention, for example, could have a molecular weight of 100 Daltons (Da.), 500 Da., 1000 Da., 2000 Da., 5000 Da., 10,000 Da., 15,000 Da., 20,000 Da., 30,000 Da., 40,000 Da. or 60,000 Da. In one embodiment of the invention, "small" scaffolds may be between about 100 Da. and 20,000 Da. In another embodiment, "large" scaffolds may be greater than about 20,000 Da. to about 200,000 Da. In preferred embodiments, the scaffold moiety is between about 100 Da. and 200,000 Da. In more preferred embodiments, the scaffold is between about 100

Da. and 20,000 Da., 200 Da. and 15,000 Da., 300 Da. and 10,000 Da., 400 Da. and 9,000 Da., 500 Da. and 5,000 Da., 600 Da. and 2,000 Da., 1000 Da. and 200,000 Da., 20,00 Da. and 200,000 Da., 100,000 and 200,000 Da., 5000 Da. and 100,000 Da., 10,000 Da. and 80,000 Da., 20,000 Da. and 60,000 Da., or 20,000 Da. and 40,000 Da. The size of the scaffolds may be varied to maximize absorption, bioavailability, circulating half-life, or efficacy of the conjugated insulin peptide.

Another component of the carrier molecule preferably comprises a coupling group that is used to covalently attach the drug to the scaffold or the carrier. The coupling groups of the invention include an amine-reactive group, a thiol-reactive group, a maleimide group, a thiol group, an aldehyde group, an NHS-ester group, a haloacetyl group, an iodoacetyl group, a bromoacetyl groups, a SMCC group, a sulfo SMCC group, a carbodiimide group and bifunctional cross-linkers such as NHS-maleimido, combinations thereof, or other coupling groups familiar to persons skilled in the art. The coupling groups of the invention can promote thiol linkages, amide linkages, oxime linkages, hydrazone linkages, thiazolidinone linkages or utilize cycloaddition reactions also called click chemistry to couple the carrier to an insulin peptide. In another embodiment, the composition preferably includes a combination of insulin and one or more additional peptides or other molecules attached to the coupling group of the scaffold molecule. The linkers of the invention may be between about 40 and 100 Daltons. In preferred embodiments, the linkers may be between about 40-50, 50-60, 60-70, 70-80, 80-90, or 90-100 Daltons. The linkers may also be varied to affect the stability or releasability of the link between the carrier and the insulin peptides or other molecules.

NHS groups are known to those skilled in the art as being useful for coupling to native peptides and proteins without having to engineer in a site of attachment. NHS groups allow attachment to most proteins and peptides that contain amino acids with amine groups such as a lysine residue. Utilization of NHS groups allows for flexibility in the site of carrier conjugation as protein structure and reaction time can influence the attachment site and number of carrier molecules conjugated to an insulin peptide. By way of example, controlling the molar ratio of NHS-carrier to a therapeutic peptide, one skilled in the art can have some control over the number of carrier molecules attached to the therapeutic peptide thus allowing for more than one carrier to be conjugated to a given therapeutic peptide, if desired.

Conjugation of the carrier to an insulin peptide is achieved by mixing a solution of the molecules together in a specific molar ratio using compatible solutions, buffers or solvents. For example, a molar ratio of about 1:1, 2:1, 4:1, 5:1, 10:1, 20:1, 25:1, 50:1, 100:1, 1000:1, or about 1:2, 1:4, 1:5, 1:10, 1:20 1:25, 1:50, 1:100 or 1:1000 of carrier to an insulin peptide could be used. By varying the ratio, this could result in different numbers of individual carriers attached to the insulin peptide, or could help to select a specific site of attachment. Attachment of the carriers is also pH, buffer, salt and temperature dependent and varying these parameters among other parameters can influence the site of attachment, the number of carriers attached, and the speed of the reaction. For example, by selecting a pH for the reaction at or below pH 6 could help selectively conjugate an aldehyde version of the carrier to the N-terminus of the insulin protein or peptide.

Additionally, in order to retain substantially the same activity of the insulin peptides, conjugation to the carriers will be at a site on the molecules that do not interfere with insulin function. This may require conjugation to the amino terminus, the carboxy terminus, or to an internal reactive amino acid.

In certain embodiments, the present invention provides carriers that include those of formula I:

$$B\text{-}(L)^a\text{-}S\text{-}(M)^b\text{-}C \qquad \qquad I$$

Wherein:
B is a targeting group selected from vitamin D, a vitamin D analog, a vitamin D-related metabolite, an analog of a vitamin D related-metabolite, a peptide that binds DBP, an anti-DBP antibody, an anti-DBP antibody derivative, a nucleotide aptamer that binds DBP, or a small carbon-based molecule that binds DBP;
S is a scaffold moiety, comprising poly(ethylene glycol), polylysine, polyethyleneimine, poly(propyleneglycol), a peptide, serum albumin, thioredoxin, an immunoglobulin, an amino acid, a nucleic acid, a glycan, a modifying group that contains a reactive linker, polylactic acid, a water-soluble polymer, a small carbon chain linker, or an additional therapeutic peptide;
C is an amine-reactive group, a thiol-reactive group, a maleimide group, a thiol group, a disulfide group, an aldehyde group, an NHS-ester group, a 4-nitrophenyl ester, an acylimidazole, a haloacetyl group, an iodoacetyl group, a bromoacetyl groups, a SMCC group, a sulfo SMCC group, a carbodiimide group and bifunctional cross-linkers such as NHS-maleimido or combinations thereof;
$(L)^a$ and $(M)^b$ are linkers independently selected from —$(CH_2)_n$—, —C(O)NH—, —HNC(O)—, —C(O)O—, —OC(O)—, —O—, —S—S—, —S—, —S(O)—, —S(O)$_2$— and —NH—;
a is an integer from 0-4; and
b is an integer from 0-4; and
n is an integer from 0-3.

In preferred embodiments, the present invention provides carriers that include those of formula I:

$$B\text{-}(L)^a\text{-}S\text{-}(M)^b\text{-}C \qquad \qquad I$$

Wherein:
B is a targeting group selected from vitamin D, a vitamin D analog, a vitamin D-related metabolite, an analog of a vitamin D related-metabolite, or a small carbon-based molecule that binds DBP;
S is a scaffold moiety, comprising poly(ethylene glycol), polylysine, poly(propyleneglycol), a peptide, serum albumin, an amino acid, a nucleic acid, a glycan, polylactic acid, a water-soluble polymer, or a small carbon chain linker;
C is a maleimide group, a thiol group, a disulfide group, an aldehyde group, an NHS-ester group, an iodoacetyl group, or a bromoacetyl group;
$(L)^a$ and $(M)^b$ are linkers independently selected from —$(CH_2)_n$—, —C(O)NH—, —HNC(O)—, —C(O)O—, —OC(O)—, —O—, —S—S—, —S—, —S(O)—, —S(O)$_2$— and —NH—;
a is an integer from 0-4; and
b is an integer from 0-4; and
n is an integer from 0-3.

In more preferred embodiments, the present invention provides carriers that include those of formula I:

$$B\text{-}(L)^a\text{-}S\text{-}(M)^b\text{-}C \qquad \qquad I$$

Wherein:
B is a targeting group selected from vitamin D, a vitamin D analog, or a vitamin D-related metabolite;
S is a scaffold moiety, comprising poly(ethylene glycol), polylysine or poly(propyleneglycol);

C is a maleimide group, a disulfide group, an aldehyde group, an NHS-ester group or an iodoacetyl group;

$(L)^a$ and $(M)^b$ are linkers independently selected from —$(CH_2)_n$—, —C(O)NH—, —HNC(O)—, —C(O)O—, —OC(O)—, —O—, —S—S—, —S—, —S(O)—, —S(O)_2$— and —NH—;

a is an integer from 0-4; and
b is an integer from 0-4; and
n is an integer from 0-3.

In most preferred embodiments, the present invention provides carriers that include those of formulas IIa, IIb, and IIc:

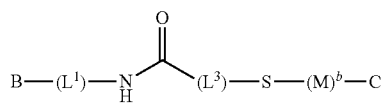

IIa

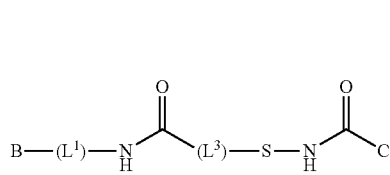

IIb

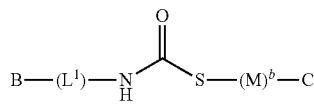

IIc

Wherein:
B is a targeting group selected from vitamin D, a vitamin D analog, or a vitamin D-related metabolite;
S is a scaffold moiety, comprising poly(ethylene glycol), or poly(propyleneglycol); and
C is a maleimide group, a disulfide group, an aldehyde group, an NHS-ester group or an iodoacetyl group;
$L^1$ is —$(CH_2)_n$—;
$L^3$ is —$(CH_2)_o$—;
$(M)^b$ are linkers independently selected from —$(CH_2)_n$—, —C(O)NH—, —HNC(O)—, —C(O)O—, —OC(O)—, —O—, —S—S—, —S—, —S(O)—, —S(O)_2$— and —NH—;
b is an integer from 0-4; and
n is 3; and
o is 1.

In PCT/US2013/031788, which is incorporated herein by reference, conjugation at the C25 position of 25-hydroxy-vitamin D3 is exemplified. The present invention incorporates conjugation at the C3 position of 25-hydroxy-vitamin D3. This gives improved half-life extension and bioavailability compared to the C25 conjugates.

In certain most preferred embodiments of formula IIa, B is represented by formula III, S is poly(ethylene glycol) and $(M)^b$-C is represented by formula IVa.

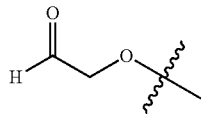

IVa

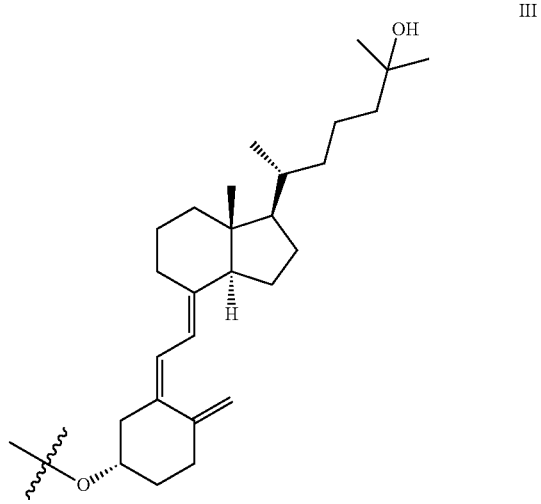

III

In certain most preferred embodiments of formula IIb, B is represented by formula III, S is poly(ethylene glycol) and $(M)^b$-C is represented by formula IVb.

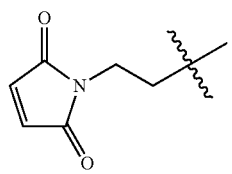

IVb

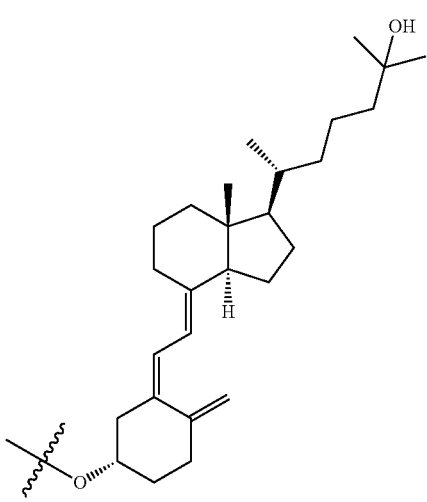

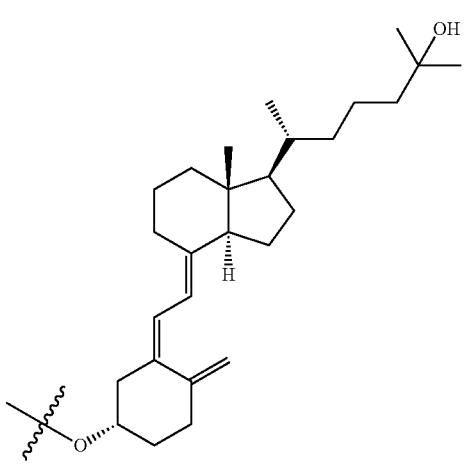

In certain most preferred embodiments of formula IIc, B is represented by formula III, S is poly(ethylene glycol) and (M)$^b$-C is represented by formula IVc.

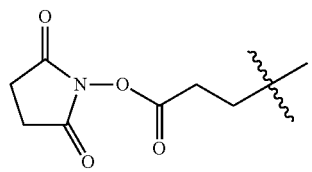

In certain most preferred embodiment, S is between about 100 Da. and 200,000 Da. In other most preferred embodiments, the scaffold moiety is between about 100 Da. and 20,000 Da., 200 Da. and 15,000 Da., 300 Da. and 10,000 Da., 400 Da. and 9,000 Da., 500 Da. and 5,000 Da., 600 Da. and 2,000 Da., 1000 Da. and 200,000 Da., 5000 Da. and 100,000 Da., 10,000 Da. and 80,000 Da., 20,000 Da. and 60,000 Da., or 20,000 Da. and 40,000 Da.

In a specific embodiment, the present invention provides a carrier represented by formula V.

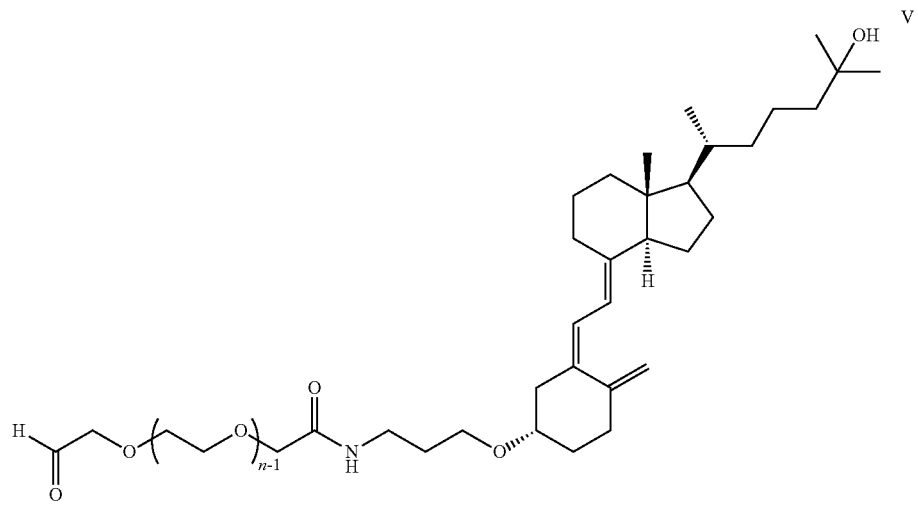

In another specific embodiment, the present invention provides a carrier represented by formula VI.

salt form. Suitable salt forms include, but are not limited to TFA, HCl, HBr, MsOH, TfOH and AcOH.

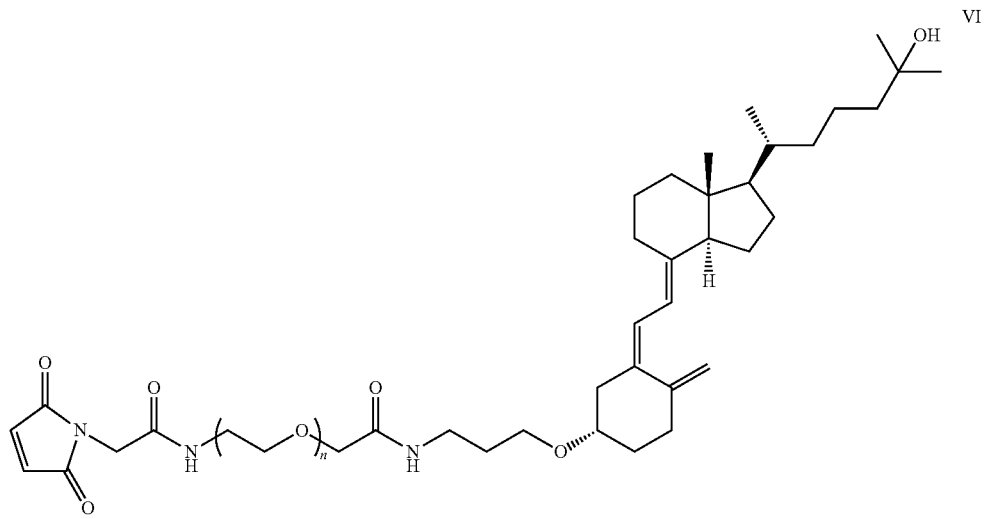

VI

In another specific embodiment, the present invention provides a carrier represented by formula VII.

Any suitable amide coupling agent may be used to form a compound of formula I.

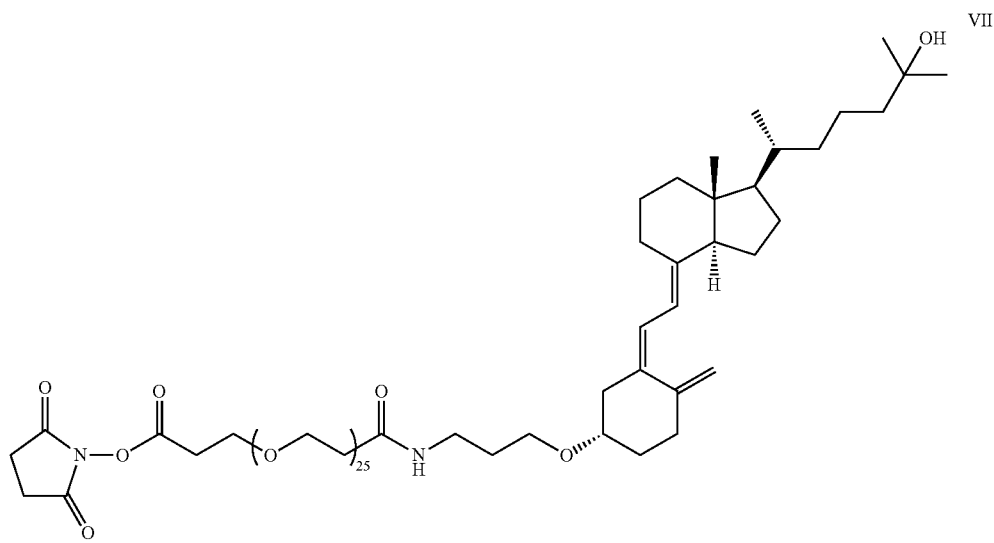

VII

In certain embodiments, the present invention provides a method for producing a carrier of formula I:

$$B\text{-}(L)^a\text{-}S\text{-}(M)^b\text{-}C \qquad I$$

comprising the step of reacting a compound of formula Ia:

$$B\text{-}L^1\text{-}NH_2 \qquad Ia$$

with a compound of formula Ib:

$$HOOC\text{-}L^3\text{-}S\text{-}(M)^b\text{-}C \qquad Ib$$

in the presence of an amide coupling agent,
wherein B, S, C and $L^1$, $L^3$, and $(M)^b$ are defined as above and $L^2$ is —C(O)NH—.

One skilled in the art will recognize that a compound of formula Ia can be used either as a free base or as a suitable Suitable amide coupling agents include, but are not limited to 2-chloromethylpyridinium iodide, BOP, PyBOP, HBTU, HATU, DCC, EDCI, TBTU and T3P. In certain embodiments, the amide coupling agent is used alone. In certain embodiments, the amide coupling agent is used with a co-reagent such as HOBT or DMAP. In certain embodiments, the amide coupling agent is used with a base such as triethylamine or diisopropylethylamine. In certain embodiments, the amide coupling agent is used with both a co-reagent such as HOBT or DMAP and a base such as triethylamine or diisopropylethylamine. One skilled in the art will recognize that co-reagents other than HOBT or DMAP may be used. Furthermore, one skilled in the art will recognize that bases other than triethylamine or diisopropylethylamine may be used.

One skilled in the art will recognize that any suitable leaving group may be coupled with the carboxylic acid of formula Ib in the presence of a suitable coupling agent to form an active ester of formula Ic:

wherein R is a suitable leaving group including, but are not limited to imidazole, HOBT, NHS and 4-nitrophenol. Suitable coupling reagents include, but are not limited to 2-chloromethylpyridinium iodide, BOP, PyBOP, HBTU, HATU, DCC, EDCI, TBTU and T3P. In some embodiments, the present invention provides a method for producing a carrier of formula I:

$$B\text{-}(L)^a\text{-}S\text{-}(M)^b\text{-}C \qquad \qquad I$$

comprising the step of reacting a compound of formula Ia:

$$B\text{-}L^1\text{-}NH_2 \qquad \qquad Ia$$

with a compound of formula Ic:

$$ROOC\text{-}L^3\text{-}S\text{-}(M)_b\text{-}C \qquad \qquad Ic$$

wherein B, S, C, R and $L^1$, $L^3$, and $(M)^b$ are defined as above and $L^2$ is —C(O)NH—.

One skilled in the art will recognize that a compound of formula Ia can be used either as a free base or as a suitable salt form. Suitable salt forms include, but are not limited to TFA, HCl, HBr, MsOH, TfOH and AcOH.

In certain embodiments, the amide coupling is performed with a base such as triethylamine or diisopropylethylamine. One skilled in the art will recognize that bases other than triethylamine or diisopropylethylamine may be used.

In certain other embodiments, the present invention provides a method for producing a carrier of formula IIa:

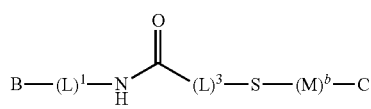

comprising the steps of reacting a compound of formula Ia:

$$B\text{-}L^1\text{-}NH_2 \qquad \qquad Ia$$

with a compound of formula Id:

$$HOOC\text{-}L^3\text{-}S\text{-}(M)^b\text{-}CH_2OH \qquad \qquad Id$$

in the presence of an amide coupling agent forming a compound of formula Ie; and

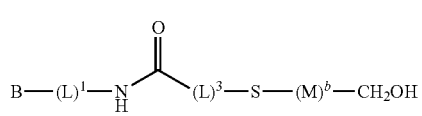

Oxidation of the primary alcohol of formula Ie to an aldehyde of formula IIa;

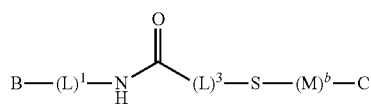

wherein B, S, $L^1$, $L^3$, $(M)^b$, b, n and o are defined as above and $L^2$ is —C(O)NH— and C is an aldehyde group.

Any suitable oxidizing agent may be used to form a compound of formula IIa. Suitable oxidizing agents include, but are not limited to, the Collins reagent, PDC, PCC, oxalyl chloride/DMSO (Swern oxidation), $SO_3$-pyridine/DMSO (Parikh-Doehring oxidation), Dess-Martin periodinane, TPAP/NMO, and TEMPO/NaOCl.

One skilled in the art will recognize that a compound of formula Ia can be used either as a free base or as a suitable salt form. Suitable salt forms include, but are not limited to TFA, HCl, HBr, MsOH, TfOH and AcOH.

Any suitable amide coupling agent may be used to form a compound of formula Ie. Suitable amide coupling agents include, but are not limited to 2-chloromethylpyridinium iodide, BOP, PyBOP, HBTU, HATU, DCC, EDCI, TBTU and T3P. In certain embodiments, the amide coupling agent is used alone. In certain embodiments, the amide coupling agent is used with a co-reagent such as HOBT or DMAP. In certain embodiments, the amide coupling agent is used with a base such as triethylamine or diisopropylethylamine. In certain embodiments, the amide coupling agent is used with both a co-reagent such as HOBT or DMAP and a base such as triethylamine or diisopropylethylamine. One skilled in the art will recognize that co-reagents other than HOBT or DMAP may be used. Furthermore, one skilled in the art will recognize that bases other than triethylamine or diisopropylethylamine may be used.

In certain embodiments, any suitable leaving group can be coupled with a carboxylic acid of formula Id in the presence of a suitable coupling reagent to form an active ester of formula If:

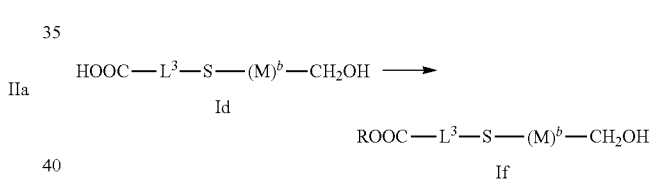

wherein R is a suitable leaving group including, but are not limited to imidazole, HOBT, NHS and 4-nitrophenol. Suitable coupling reagents include, but are not limited to 2-chloromethylpyridinium iodide, BOP, PyBOP, HBTU, HATU, DCC, EDCI, TBTU and T3P.

In some embodiments, the present invention provides a method for producing a carrier of formula Ie:

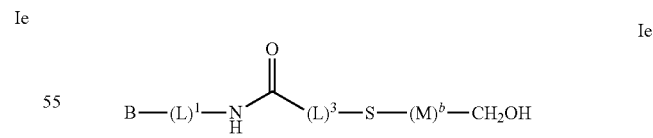

comprising the step of reacting a compound of formula Ia;

$$B\text{-}L^1\text{-}NH_2 \qquad \qquad Ia$$

with a compound of formula If; and $$ROOC\text{-}L^3\text{-}S\text{-}(M)^b\text{-}CH_2OH \qquad \qquad If$$

Oxidation of the primary alcohol of formula Ie to an aldehyde of formula IIa;

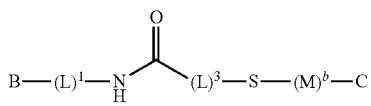

wherein B, S, C, R and $L^1$, $L^3$, and $(M)^b$ are defined as above and $L^2$ is —C(O)NH—.

One skilled in the art will recognize that a compound of formula Ia can be used either as a free base or as a suitable salt form. Suitable salt forms include, but are not limited to TFA, HCl, HBr, MsOH, TfOH and AcOH.

In certain embodiments, the amide coupling is performed with a base such as triethylamine or diisopropylethylamine. One skilled in the art will recognize that bases other than triethylamine or diisopropylethylamine may be used.

Any suitable oxidizing agent may be used to form a compound of formula IIa. Suitable oxidizing agents include, but are not limited to, the Collins reagent, PDC, PCC, oxalyl chloride/DMSO (Swern oxidation), $SO_3$-pyridine/DMSO (Parikh-Doehring oxidation), Dess-Martin periodinane, TPAP/NMO, and TEMPO/NaOCl.

In certain other embodiments, the present invention provides a method for producing a carrier of formula IIc:

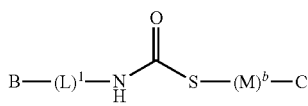

comprising the steps of reacting a compound of formula Ia:

with a compound of formula Ig:

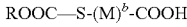

forming a compound of formula Ih; and

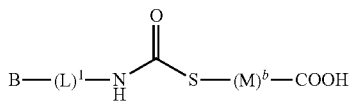

Converting a carboxylic acid of formula Ih to an active ester of formula IIc;

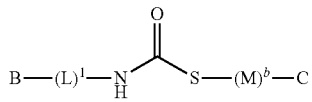

wherein B, S, C, R, $L^1$, $(M)^b$, b, n and o are defined as above and $L^2$ is —C(O)NH—.

One skilled in the art will recognize that a compound of formula Ia can be used either as a free base or as a suitable salt form. Suitable salt forms include, but are not limited to TFA, HCl, HBr, MsOH, TfOH and AcOH.

Any suitable leaving group can be coupled with a carboxylic acid of formula Ih in the presence of a suitable coupling reagent to form an active ester of formula IIc. Suitable leaving groups include, but are not limited to imidazole, HOBT, NHS and 4-nitrophenol. Suitable coupling reagents include, but are not limited to 2-chloromethylpyridinium iodide, BOP, PyBOP, HBTU, HATU, DCC, EDCI, TBTU and T3P.

In some embodiments, an active ester of formula IIc is formed from a carboxylic acid of formula Ih using a combination of a suitable leaving group and a coupling reagent.

In some embodiments, an active ester of formula IIc is formed from a carboxylic acid of formula Ih using a single reagent that produces a leaving group and also effects a coupling reaction. Such reagents include, but are not limited to 1,1'-carbonyldiimidazole, N,N'-disuccinimidyl carbonate, 4-nitrophenyl trifluoroacetate and HBTU. In some embodiments, the single reagent is used alone. In other embodiments, the single reagent is used with an acyl transfer catalyst. Such acyl transfer catalysts include, but are not limited to DMAP and pyridine. One skilled in the art will recognize that additional acyl transfer catalysts may be used.

In a specific embodiment, the present invention provides a method for producing a carrier represented by formula V:

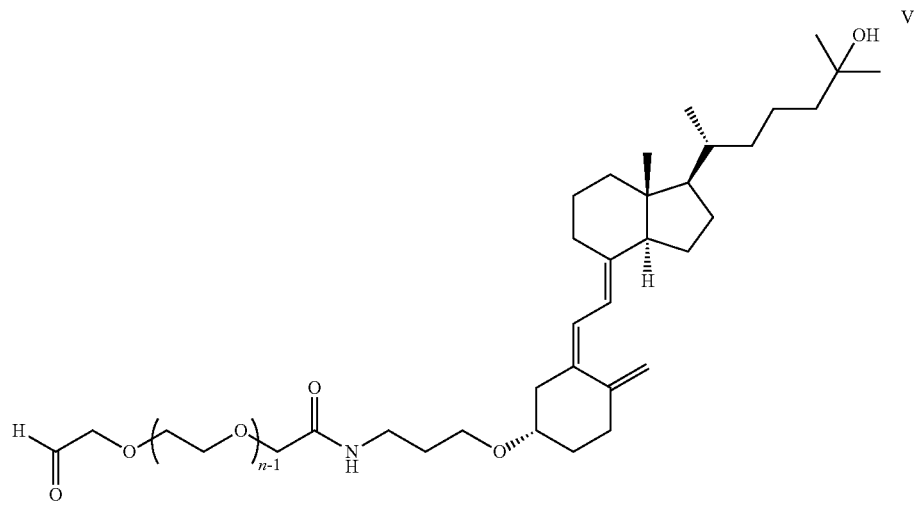

comprising the step of reacting a compound of formula Va:
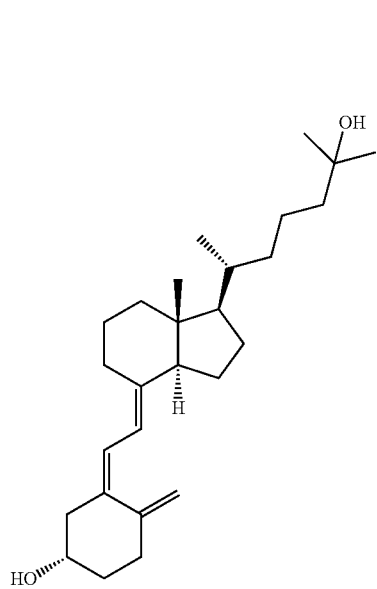
with a compound of formula Vb:
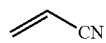
to form a compound of formula Vc;
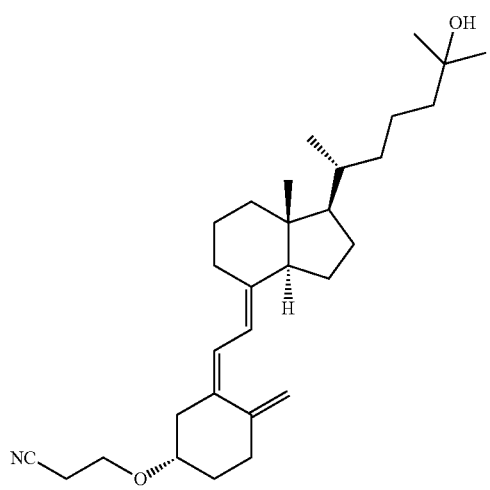
Reduction of the nitrile group to form the amine of formula Vd;
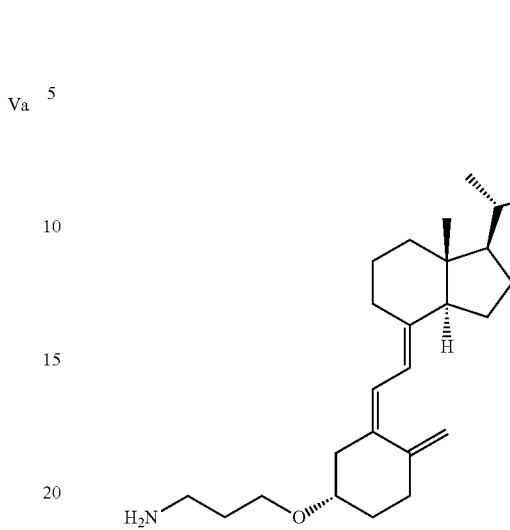
Reaction of the compound of formula Vd with a compound of formula Ve;
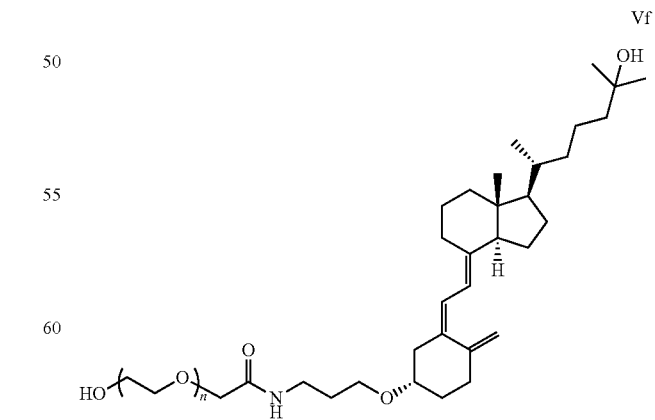
To form a compound of the formula Vf
Oxidation of the primary alcohol of formula Vf to form the aldehyde of formula V.

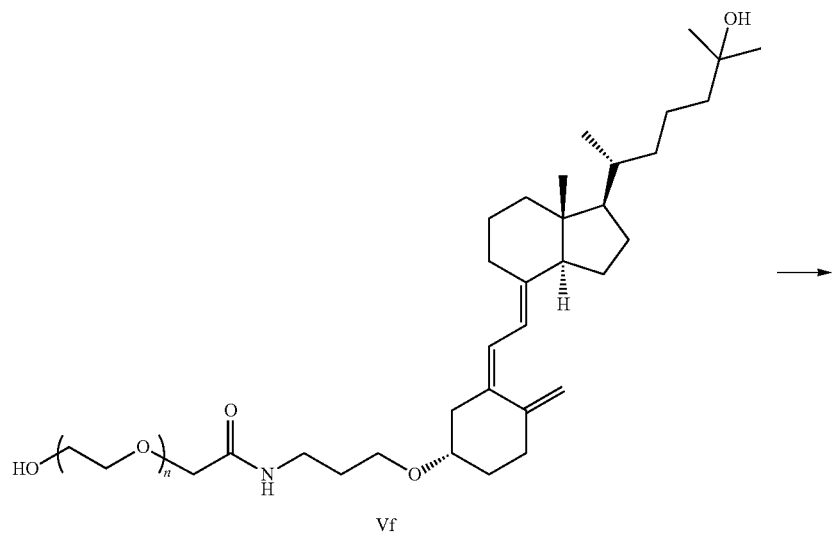
Vf
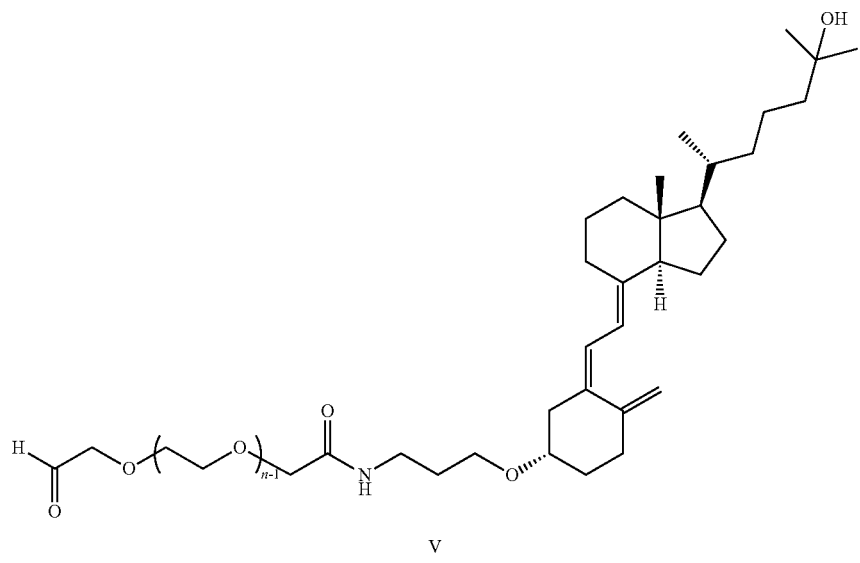
V

In some embodiments, the reaction of a compound of formula Vb with a compound of formula Va is promoted by addition of Triton B. One skilled in the art will recognize that other reagents may be used to promote nucleophilic addition to acrylonitrile.

In some embodiments, reduction of the nitrile of formula Vc to the amine of formula Vd is performed using $AlCl_3$/LAH. One skilled in the art will recognize that other reduction reagents may be used including sodium, $H_2$/Pd, $H_2$/Raney nickel, and diborane.

One skilled in the art will recognize that a compound of formula Vd can be used either as a free base or as a suitable salt form. Suitable salt forms include, but are not limited to TFA, HCl, HBr, MsOH, TfOH and AcOH.

In certain embodiments, a base such as triethylamine or diisopropylethylamine is used to promote coupling of the NHS-ester of formula Ve with the amine of formula Vd. One skilled in the art will recognize that bases other than triethylamine or diisopropylethylamine may be used.

Any suitable oxidizing agent may be used to form a compound of formula V. Suitable oxidizing agents include, but are not limited to, the Collins reagent, PDC, PCC, oxalyl chloride/DMSO (Swern oxidation), $SO_3$-pyridine/DMSO (Parikh-Doehring oxidation), Dess-Martin periodinane, TPAP/NMO, and TEMPO/NaOCl.

In another specific embodiment, the present invention provides a method for producing a carrier represented by formula VI:

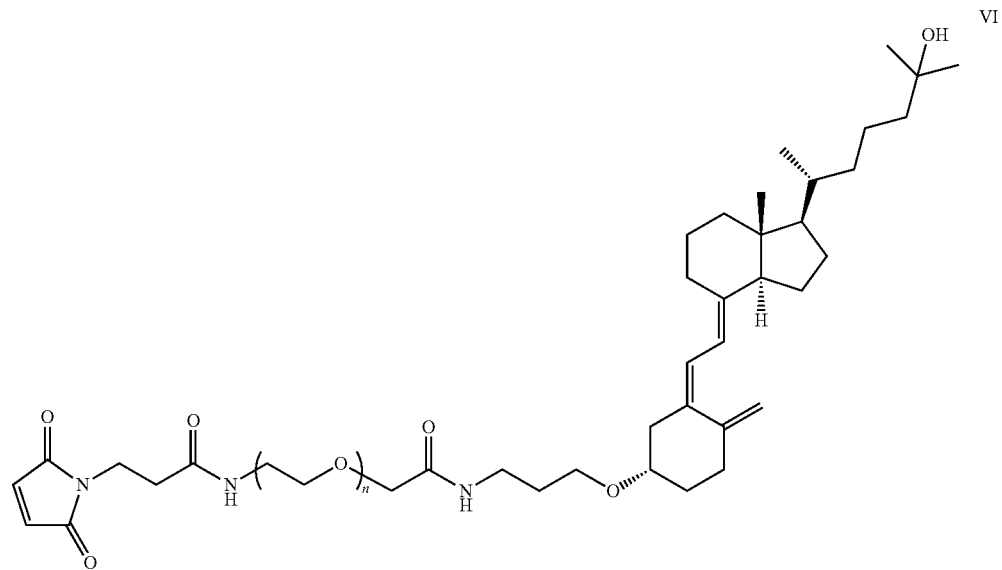

comprising the steps of reacting a compound of formula Vd:

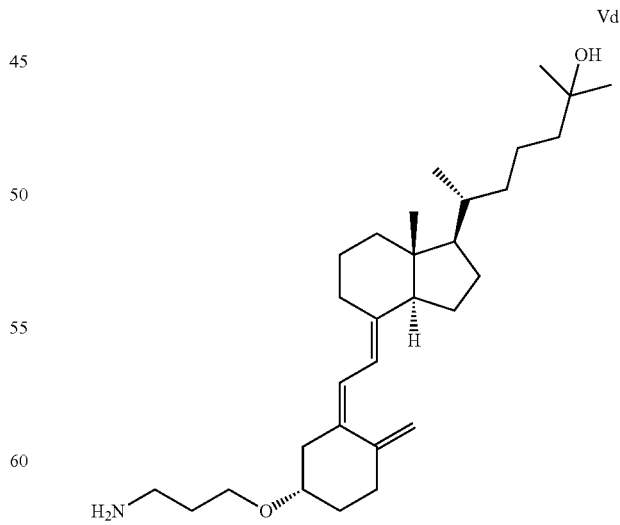

in the presence of an amide coupling agent with a compound of formula VIa:

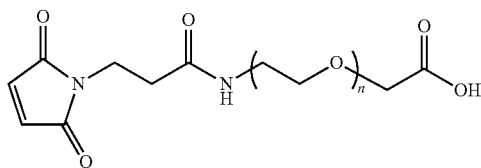

VIa

One skilled in the art will recognize that a compound of formula Vd can be used either as a free base or as a suitable salt form. Suitable salt forms include, but are not limited to TFA, HCl, HBr, MsOH, TfOH and AcOH.

Any suitable amide coupling agent may be used to form a compound of formula VI. Suitable amide coupling agents include, but are not limited to 2-chloromethylpyridinium iodide, BOP, PyBOP, HBTU, HATU, DCC, EDCI, TBTU and T3P. In certain embodiments, the amide coupling agent is used alone. In certain embodiments, the amide coupling agent is used with a co-reagent such as HOBT or DMAP. In certain embodiments, the amide coupling agent is used with a base such as triethylamine or diisopropylethylamine. In certain embodiments, the amide coupling agent is used with both a co-reagent such as HOBT or DMAP and a base such as triethylamine or diisopropylethylamine. One skilled in the art will recognize that co-reagents other than HOBT or DMAP may be used. Furthermore, one skilled in the art will recognize that bases other than triethylamine or diisopropylethylamine may be used.

In another specific embodiment, the present invention provides a method for producing a carrier represented by formula VII:

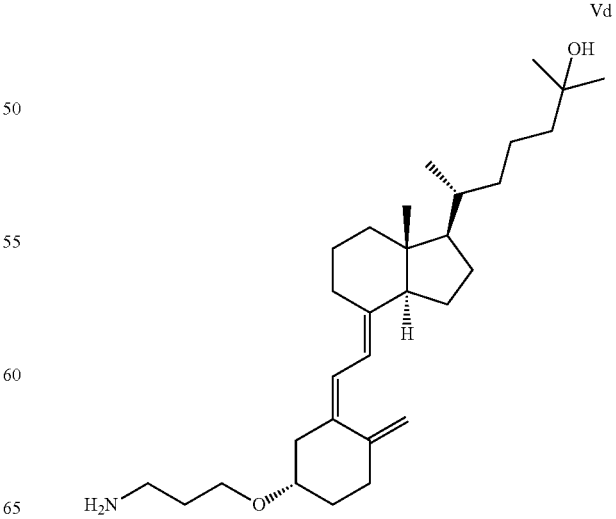

comprising the steps of reacting a compound of formula Vd:

with a compound of formula VIIa:

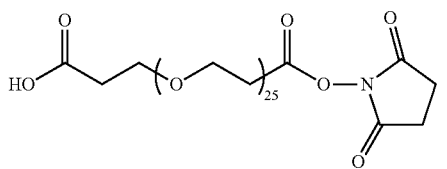

forming a compound of formula VIIb; and

In certain embodiments, a base such as triethylamine or diisopropylethylamine is used to promote coupling of the NHS-ester of formula VIIa with the amine of formula Va. One skilled in the art will recognize that bases other than triethylamine or diisopropylethylamine may be used.

NHS can be coupled with a carboxylic acid of formula VIIb in the presence of a suitable coupling reagent to form an active ester of formula VII. Suitable coupling reagents include, but are not limited to 2-chloromethylpyridinium iodide, BOP, PyBOP, HBTU, HATU, DCC, EDCI, TBTU, and T3P.

In some embodiments, an active ester of formula VII is formed from a carboxylic acid of formula VIIb using a combination of NHS and a coupling reagent.

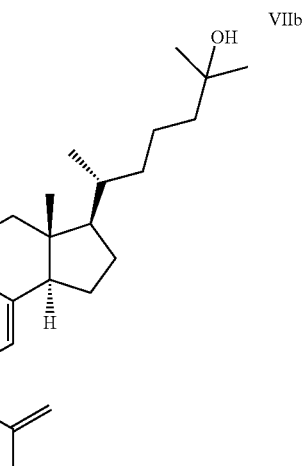
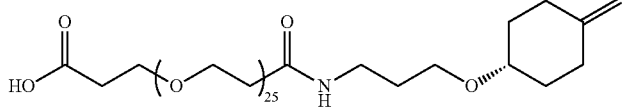

Converting a carboxylic acid of formula VIIb to an active ester of formula VII;

In some embodiments, an active ester of formula VII is formed from a carboxylic acid of formula VIIb using a

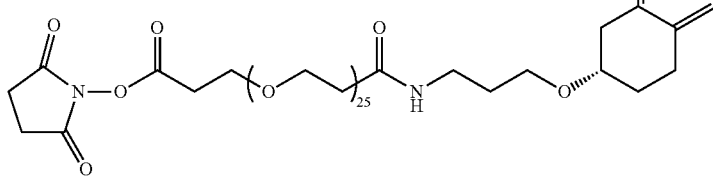

One skilled in the art will recognize that a compound of formula Vd can be used either as a free base or as a suitable salt form. Suitable salt forms include, but are not limited to TFA, HCl, HBr, MsOH, TfOH and AcOH.

single reagent that produces a leaving group and also effects a coupling reaction. Such reagents include, but are not limited to, N,N'-disuccinimidyl carbonate. In some embodiments, the single reagent is used alone. In other embodiments the reagent is used with an acyl transfer catalyst. Such acyl transfer catalysts include, but are not limited to DMAP and pyridine. One skilled in the art will recognize that additional acyl transfer catalysts may be used.

One skilled in the art will recognize that there are other methods to conjugate a linker and scaffold to the C3 position of vitamin D derivatives and analogues. For example, the C3 hydroxy group may be acylated by various groups as practiced by N. Kobayashi, K. Ueda, J. Kitahori, and K. Shimada, *Steroids*, 57, 488-493 (1992); J. G Haddad, et al., *Biochemistry*, 31, 7174-7181 (1992); A. Kutner, R. P. Link, H. K. Schnoes, H. F. DeLuca, *Bioorg. Chem.*, 14, 134-147 (1986); and R. Ray, S. A. Holick, N. Hanafin, and M. F. Holick, *Biochemistry*, 25, 4729-4733 (1986). The foregoing references are incorporated by reference in their entirety. One skilled in the art will recognize that these chemistries could be modified to synthesize compounds of the formula I:

$$B\text{-}(L)^a\text{-}S\text{-}(M)^b\text{-}C \qquad \qquad I$$

wherein B, S, C, $(L)^a$, and $(M)^b$ are defined as above.

If desired, insulin peptide carrier conjugates having different molecular weights can be isolated using gel filtration chromatography and/or ion exchange chromatography. Gel filtration chromatography may be used to fractionate different insulin peptide carrier conjugates (e.g., 1-mer, 2-mer, 3-mer, and so forth, wherein "1-mer" indicates one targeting group molecule per insulin peptide, "2-mer" indicates two targeting groups attached to an insulin peptide, and so on) on the basis of their differing molecular weights (where the difference corresponds essentially to the average molecular weight of the targeting group).

Gel filtration columns suitable for carrying out this type of separation include Superdex and Sephadex columns available from Amersham Biosciences (Piscataway, N.J.). Selection of a particular column will depend upon the desired fractionation range desired. Elution is generally carried out using a suitable buffer, such as phosphate, acetate, or the like. The collected fractions may be analyzed by a number of different methods, for example, (i) optical density (OD) at 280 nm for protein content, (ii) bovine serum albumin (BSA) protein analysis, and (iii) sodium dodecyl sulfate polyacrylamide gel electrophoresis (SDS PAGE).

Separation of insulin peptide carrier conjugates can also be carried out by reverse phase chromatography using a reverse phase-high performance liquid chromatography (RP-HPLC) C18 column (Amersham Biosciences or Vydac) or by ion exchange chromatography using an ion exchange column, e.g., a DEAE- or CM-Sepharose ion exchange column available from Amersham Biosciences. The resulting purified compositions are preferably substantially free of the non-targeting group-conjugated insulin peptide. In addition, the compositions preferably are substantially free of all other non-covalently attached targeting groups.

As described herein, the carriers of the invention may be non-hormonal 25-hydroxy vitamin D or analogs thereof having a coupling group on the 3' carbon. "25-hydroxy vitamin D analogs" as used herein includes both naturally-occurring vitamin D metabolite forms as well as other chemically-modified forms. The carriers of the invention do not include an active (i.e. hormonal) form of vitamin D (typically having a hydroxyl group at the 1 carbon). These compounds are based on the vitamin D structure and retain partial function of vitamin D (i.e. they interact with DBP, albeit at varying affinities. The following list exemplifies vitamin D analog forms known in the art. They may, however, be hormonal or have the C1 hydroxyl group. They are presented here solely for their chemical properties as vitamin D analogs, not for their functional hormonal properties: OCT, a chemically synthesized of 1,25(OH)2D3 with an oxygen atom at the 22 position in the side chain (Abe et. al., FEBS Lett. 226:58-62 (1987)); Gemini vitamin D analog, 1α,25-dihydroxy-20R-21(3-hydroxy-3-deuteromethyl-4,4,4-trideuterobutyl)-23-yne-26,27-hexafluoro-cholecalciferol (BXL0124) (So et al., Mol Pharmacol. 79(3):360-7 (2011)); Paricalcitol, a vitamin D2 derived sterol lacking the carbon-19 methylene group found in all natural vitamin D metabolites (Slatopolsky et al., Am J. Kidney Dis. 26: 852 (1995)); Doxercalciferol (1α-hydroxyvitamin D2), like alfacalcidol (1α-hydroxyvitamin D3), is a prodrug which is hydroxylated in the liver to 1α,25(OH)2D2, however, unlike alfacalcidol, doxercalciferol is also 24-hydroxylated to produce 1α,24(S)—(OH)2D2 (Knutson et al., Biochem Pharmacol 53: 829 (1997)); Dihydrotachysterol2 (DHT2), hydroxylated in vivo to 25(OH)DHT2, 1,25(OH)2DHT2 (McIntyre et al., Kidney Int. 55: 500 (1999)), ED-71, and eldecalcitol. See also Erben and Musculoskel, Neuron Interact. 2(1):59-69 (2001) and Steddon et al. Nephrol. Dial. Transplant. 16 (10): 1965-1967 (2001). The foregoing references are incorporated by reference in their entirety.

In another embodiment, the carrier further comprises a pharmaceutically acceptable scaffold moiety covalently attached to the targeting group and the insulin peptide. The scaffold moiety of the carriers of the invention does not necessarily participate in but may contribute to the function or improve the pharmacokinetic properties of the insulin peptide. The scaffolds of the invention do not substantially interfere with the binding of the targeting group to DBP. Likewise, the scaffolds of the invention do not substantially interfere with structure or function of the insulin peptide. The length of the scaffold moiety is dependent upon the character of the targeting group and the insulin peptide. One skilled in the art will recognize that various combinations of atoms provide for variable length molecules based upon known distances between various bonds (Morrison, and Boyd, Organic Chemistry, 3rd Ed, Allyn and Bacon, Inc., Boston, Mass. (1977), incorporated herein by reference). Other scaffolds contemplated by the invention include peptide linkers, protein linkers such as human serum albumin or immunoglobulin family proteins or fragments thereof, nucleic acid linkers, small carbon chain linkers, carbon linkers with oxygen or nitrogen interspersed, or combinations thereof. In preferred embodiments, the linkers are non-releasable or stable.

The invention comprises insulin, a therapeutic peptide. The term peptide is meant to include a string of amino acids. The amino acids in the peptides of the invention may be naturally-occurring or non-naturally-occurring. The peptides of the invention may be synthesized chemically or biologically, and can include cysteine-rich peptides, circular peptides, stapled peptides, peptides that include D- or L-amino acids and mixtures thereof, peptidomimetics, peptide-nucleic acids (PNAs), and combinations thereof. The invention contemplates synthetic insulin analogs that would be improved as clinical products through further modification by the methods described herein. In some embodiments, the insulin peptides of the invention are or have at least a 90% sequence identity to SEQ ID NO: 1, 2, or 5-8.

The invention contemplates branched or cyclic insulin derivatives. Cyclic, branched and branched circular peptides result from post-translational natural processes and are also made by suitable synthetic methods. In some embodiments, any peptide product described herein comprises a peptide analog described above that is then covalently attached to an alkyl-glycoside surfactant moiety.

Other embodiments include insulin peptide chains that are comprised of natural and unnatural amino acids or analogs of natural amino acids. As used herein, peptide and/or protein "analogs" comprise non-natural amino acids based on natural amino acids, such as tyrosine analogs, which includes para-substituted tyrosines, ortho-substituted tyrosines, and meta-substituted tyrosines, wherein the substituent on the tyrosine comprises an acetyl group, a benzoyl group, an amino group, a hydrazine, an hydroxyamine, a thiol group, a carboxy group, a methyl group, an isopropyl group, a C2-C20 straight chain or branched hydrocarbon, a saturated or unsaturated hydrocarbon, an O-methyl group, a polyether group, a halogen, a nitro group, or the like.

Additional embodiments include insulin peptide chains having modified amino acids. Examples include acylated amino acids at the ϵ-position of lysine, amino acids with fatty acids such as octanoic, decanoic, dodecanoic, tetradecanoic, hexadecanoic, octadecanoic, 3-phenylpropanoic acids and the like, or with saturated or unsaturated alkyl chains (Zhang, L. and Bulaj, G (2012) Curr Med Chem 19: 1602-1618, incorporated herein by reference in its entirety).

The invention further contemplates insulin peptide chains comprising natural and unnatural amino acids or analogs of natural amino acids. In some embodiments, peptide or protein "analogs" comprise non-natural amino acids based on natural amino acids, such as tyrosine analogs, which includes para-substituted tyrosines, ortho-substituted tyrosines, and meta-substituted tyrosines, wherein the substituent on the tyrosine comprises an acetyl group, a benzoyl group, an amino group, a hydrazine, an hydroxyamine, a thiol group, a carboxy group, a methyl group, an isopropyl group, a C2-C20 straight chain or branched hydrocarbon, a saturated or unsaturated hydrocarbon, an O-methyl group, a polyether group, a halogen, a nitro group, or the like. Examples of tyrosine analogs include 2,4-dimethyl-tyrosine (Dmt), 2,4-diethyl-tyrosine, O-4-allyl-tyrosine, 4-propyl-tyrosine, Ca-methyl-tyrosine and the like. Examples of lysine analogs include ornithine (Orn), homo-lysine, Ca-methyl-lysine (CMeLys), and the like. Examples of phenylalanine analogs include, but are not limited to, meta-substituted phenylalanines, wherein the substituent comprises a methoxy group, a C1-C20 alkyl group, for example a methyl group, an allyl group, an acetyl group, or the like. Specific examples include, but are not limited to, 2,4,6-trimethyl-L-phenylalanine (Tmp), O-methyl-tyrosine, 3-(2-naphthyl)alanine (Nal(2)), 3-(1-naphthyl)alanine (Nal(1)), 3-methyl-phenylalanine, 1,2,3,4-tetrahydroisoquinoline-3-carboxylic acid (Tic), fluorinated phenylalanines, isopropyl-phenylalanine, p-azido-phenylalanine, p-acyl-phenylalanine, p-benzoyl-phenylalanine, p-iodo-phenylalanine, p-bromophenylalanine, p-amino-phenylalanine, and isopropyl-phenylalanine, and the like.

Also contemplated within the scope of embodiments are insulin peptide chains containing nonstandard or unnatural amino acids known to the art, for example, C-alpha-disubstituted amino acids such as Aib, Ca-diethylglycine (Deg), aminocyclopentane-1-carboxylic acid (Ac4c), aminocyclopentane-1-carboxylic acid (Ac5c), and the like. Such amino acids frequently lead to a restrained structure, often biased toward an alpha helical structure (Kaul, R. and Balaram, P. (1999) Bioorg Med Chem 7: 105-117, incorporated herein by reference in its entirety). Additional examples of such unnatural amino acids useful in analog design are homo-arginine (Har) and the like. Substitution of reduced amide bonds in certain instances leads to improved protection from enzymatic destruction or alters receptor binding. By way of example, incorporation of a Tic-Phe dipeptide unit with a reduced amide bond between the residues (designated as Tic-F[CH2-NH]ˆ-Phe) reduces enzymatic degradation.

In some embodiments, modifications at the amino or carboxyl terminus may optionally be introduced into the present peptides or proteins (Nestor, J. J., Jr. (2009) Current Medicinal Chemistry 16: 4399-4418). For example, the present peptides or proteins can be truncated or acylated on the N-terminus (Gourlet, P., et al. (1998) Eur J Pharmacol 354: 105-111, Gozes, I. and Furman, S. (2003) Curr Pharm Des 9: 483-494), the contents of which is incorporated herein by reference in their entirety). Other modifications to the N-terminus of peptides or proteins, such as deletions or incorporation of D-amino acids such as D-Phe result in potent and long acting agonists or antagonists when substituted with the modifications described herein such as long chain alkyl glycosides.

Thus, the invention provides insulin peptide analogs wherein the native insulin peptide is modified by acetylation, acylation, PEGylation, ADP-ribosylation, amidation, covalent attachment of a lipid or lipid derivative, covalent attachment of phosphotidylinositol, cross-linking, cyclization, disulfide bond formation, demethylation, formation of covalent cross-link formation of cysteine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, glycosylation, lipid attachment, sulfation, gamma-carboxylation of glutamic acid residues, hydroxylation and ADP-ribosylation, selenoylation, sulfation, transfer-RNA mediated addition of amino acids to proteins, such as arginylation, and ubiquitination. See, for instance, (Nestor, J. J., Jr. (2007) Comprehensive Medicinal Chemistry II 2: 573-601, Nestor, J. J., Jr. (2009) Current Medicinal Chemistry 16: 4399-4418, Uy, R. and Wold, F. (1977) Science 198:890-6, Seifter, S. and Englard, S. (1990) Methods Enzymol 182: 626-646, Rattan, S. I., et al. (1992) Ann NY Acad Sci 663: 48-62). The foregoing references are incorporated by reference in their entirety.

Glycosylated insulin peptides may be prepared using conventional Fmoc chemistry and solid phase peptide synthesis techniques, e.g., on resin, where the desired protected glycoamino acids are prepared prior to peptide synthesis and then introduced into the peptide chain at the desired position during peptide synthesis. Thus, the insulin peptide polymer conjugates may be conjugated in vitro. The glycosylation may occur before deprotection. Preparation of amino acid glycosides is described in U.S. Pat. No. 5,767,254, WO 2005/097158, and Doores, K., et al., Chem. Commun., 1401-1403, 2006, which are incorporated herein by reference in their entirety. For example, alpha and beta selective glycosylations of serine and threonine residues are carried out using the Koenigs-Knorr reaction and Lemieux's in situ anomerization methodology with Schiff base intermediates. Deprotection of the Schiff base glycoside is then carried out using mildly acidic conditions or hydrogenolysis. A composition, comprising a glycosylated insulin peptide conjugate is made by stepwise solid phase peptide synthesis involving contacting a growing peptide chain with protected amino acids in a stepwise manner, wherein at least one of the protected amino acids is glycosylated, followed by water-soluble polymer conjugation. Such compositions may have a purity of at least 95%, at least 97%, or at least 98%, of a single species of the glycosylated and conjugated insulin peptide.

Monosaccharides that may by used for introduction at one or more amino acid residues of the insulin peptides, defined and/or disclosed herein, include glucose (dextrose), fructose, galactose, and ribose. Additional monosaccharides suitable for use include glyceraldehydes, dihydroxyacetone, erythrose, threose, erythrulose, arabinose, lyxose, xylose, ribulose, xylulose, allose, altrose, mannose, N-Acetylneuraminic acid, fucose, N-Acetylgalactosamine, and N-Acetylglucosamine, as well as others. Glycosides, such as mono-, di-, and trisaccharides for use in modifying an insulin peptide, one or more amino acid residues of the insulin peptides defined and/or disclosed herein include sucrose, lactose, maltose, trehalose, melibiose, and cellobiose, among others. Trisaccharides include acarbose, raffinose, and melezitose.

In further embodiments of the invention, the insulin peptides defined and/or disclosed herein may be chemically coupled to biotin. The biotin/insulin peptide can then bind to avidin.

Some aspects of the assembly of carriers utilizes chemical methods that are well-known in the art. For example, Vitamin E-PEG is manufactured by Eastman Chemical, Biotin-PEG is manufactured by many PEG manufacturers such as Enzon, Nektar and NOF Corporation. Methods of producing PEG molecules with some vitamins and other therapeutic peptides linked to them follow these and other chemical methods known in the art. The attachment of PEG to an oligonucleotide or related molecule occurs, for example, as the PEG2-N-hydroxysuccinimide ester coupled to the oligonucleotide through the 5' amine moiety. Several coupling methods are contemplated and include, for example, NHS coupling to amine groups such as a lysine residue on a peptide, maleimide coupling to sulfhydryl group such as on a cysteine residue, iodoacetyl coupling to a sulfhydryl group, pyridyldithiol coupling to a sulfhydryl group, hydrazide for coupling to a carbohydrate group, aldehyde for coupling to the N-terminus, or tetrafluorophenyl ester coupling that is known to react with primary or secondary amines. Other possible chemical coupling methods are known to those skilled in the art and can be substituted. By way of example, conjugation using the coupling groups of the invention may be carried out using the compositions and methods described in WO93/012145 (Atassi et al.) and also see U.S. Pat. No. 7,803,777 (Defrees et al.), incorporated by reference herein in their entirety.

Exemplary drug formulations of the invention include aqueous solutions, organic solutions, powder formulations, solid formulations and a mixed phase formulations.

Pharmaceutical compositions of this invention comprise any of the compounds of the present invention, and pharmaceutically acceptable salts thereof, with any pharmaceutically acceptable carrier, adjuvant or vehicle. Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium tri silicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Pharmaceutically acceptable salts retain the desired biological activity of the insulin composition without toxic side effects. Examples of such salts are (a) acid addition salts formed with inorganic acids, for example, hydrochloric acid, hydrobromic acid, sulfuric acid, phosphoric acid, nitric acid and the like/and salts formed with organic acids such as, for example, acetic acid, trifluoroacetic acid, tartaric acid, succinic acid, maleic acid, fumaric acid, gluconic acid, citric acid, malic acid, ascorbic acid, benzoic acid, tanic acid, pamoic acid, alginic acid, polyglutamic acid, naphthalenesulfonic acid, naphthalene disulfonic acid, polygalacturonic acid and the like; (b) base addition salts or complexes formed with polyvalent metal cations such as zinc, calcium, bismuth, barium, magnesium, aluminum, copper, cobalt, nickel, cadmium, and the like; or with an organic cation formed from N,N'-dibenzylethylenediamine or ethlenediamine; or (c) combinations of (a) and (b), e.g. a zinc tannate salt and the like.

The pharmaceutical compositions of this invention may be administered by subcutaneous, transdermal, oral, parenteral, inhalation, ocular, topical, rectal, nasal, buccal (including sublingual), vaginal, or implanted reservoir modes. The pharmaceutical compositions of this invention may contain any conventional, non-toxic, pharmaceutically-acceptable carriers, adjuvants or vehicles. The term parenteral as used herein includes subcutaneous, intracutaneous, intravenous, intramuscular, intraarticular, intrasynovial, intrasternal, intrathecal, intralesional, and intracranial injection or infusion techniques.

Also contemplated, in some embodiments, are pharmaceutical compositions comprising insulin and analogs or metabolites thereof as described herein, or pharmaceutically acceptable salt thereof, in a mixture with a pharmaceutically acceptable, non-toxic component. As mentioned above, such compositions may be prepared for parenteral administration, particularly in the form of liquid solutions or suspensions; for oral or buccal administration, particularly in the form of tablets or capsules; for intranasal administration, particularly in the form of powders, nasal drops, evaporating solutions or aerosols; for inhalation, particularly in the form of liquid solutions or dry powders with excipients, defined broadly; for transdermal administration, particularly in the form of a skin patch or microneedle patch; and for rectal or vaginal administration, particularly in the form of a suppository.

The compositions may conveniently be administered in unit dosage form and may be prepared by any of the methods well-known in the pharmaceutical art, for example, as described in Remington's Pharmaceutical Sciences, 17th ed., Mack Publishing Co., Easton, Pa. (1985), incorporated herein by reference in its entirety. Formulations for parenteral administration may contain as excipients sterile water or saline alkylene glycols such as propylene glycol, polyalkylene glycols such as polyethylene glycol, saccharides, oils of vegetable origin, hydrogenated napthalenes, serum albumin or other nanoparticles (as used in Abraxane™, American Pharmaceutical Partners, Inc. Schaumburg, Ill.), and the like. For oral administration, the formulation can be enhanced by the addition of bile salts or acylcarnitines. Formulations for nasal administration may be solid or solutions in evaporating solvents such as hydrofluorocarbons, and may contain excipients for stabilization, for example, saccharides, surfactants, submicron anhydrous alpha-lactose or dextran, or may be aqueous or oily solutions for use in the form of nasal drops or metered spray. For buccal administration, typical excipients include sugars, calcium stearate, magnesium stearate, pregelatinated starch, and the like.

Delivery of modified insulin peptides described herein to a subject over prolonged periods of time, for example, for periods of one week to one year, may be accomplished by a single administration of a controlled release system containing sufficient active ingredient for the desired release period. Various controlled release systems, such as monolithic or reservoir-type microcapsules, depot implants, polymeric hydrogels, osmotic pumps, vesicles, micelles, liposomes, transdermal patches, iontophoretic devices and alternative injectable dosage forms may be utilized for this purpose. Localization at the site to which delivery of the active ingredient is desired is an additional feature of some controlled release devices, which may prove beneficial in the treatment of certain disorders.

In certain embodiments for transdermal administration, delivery across the barrier of the skin would be enhanced using electrodes (e.g. iontophoresis), electroporation, or the application of short, high-voltage electrical pulses to the skin, radiofrequencies, ultrasound (e.g. sonophoresis), microprojections (e.g. microneedles), jet injectors, thermal ablation, magnetophoresis, lasers, velocity, or photomechanical waves. The drug can be included in single-layer drug-in-adhesive, multi-layer drug-in-adhesive, reservoir, matrix, or vapor style patches, or could utilize patchless technology. Delivery across the barrier of the skin could also be enhanced using encapsulation, a skin lipid fluidizer, or a hollow or solid microstructured transdermal system (MTS, such as that manufactured by 3M), jet injectors. Additives to the formulation to aid in the passage of insulin peptides through the skin include prodrugs, chemicals, surfactants, cell penetrating peptides, permeation enhancers, encapsulation technologies, enzymes, enzyme inhibitors, gels, nanoparticles and peptide or protein chaperones.

One form of controlled-release formulation contains the insulin peptide or its salt dispersed or encapsulated in a slowly degrading, non-toxic, non-antigenic polymer such as copoly(lactic/glycolic) acid, as described in the pioneering work of Kent et al., U.S. Pat. No. 4,675,189, incorporated by reference herein. The peptides may also be formulated in cholesterol or other lipid matrix pellets, or silastomer matrix implants. Additional slow release, depot implant or injectable formulations will be apparent to the skilled artisan. See, for example, Sustained and Controlled Release Drug Delivery Systems, J R Robinson ed., Marcel Dekker Inc., New York, 1978; and Controlled Release of Biologically Active Agents, R W Baker, John Wiley & Sons, New York, 1987. The foregoing are incorporated by reference in their entirety.

An additional form of controlled-release formulation comprises a solution of biodegradable polymer, such as copoly(lactic/glycolic acid) or block copolymers of lactic acid and PEG; is a bioacceptable solvent, which is injected subcutaneously or intramuscularly to achieve a depot formulation. Mixing of the insulin peptides described herein with such a polymeric formulation is suitable to achieve very long duration of action formulations.

When formulated for nasal administration, the absorption across the nasal mucous membrane may be further enhanced by surfactants, such as, for example, glycocholic acid, cholic acid, taurocholic acid, ethocholic acid, deoxycholic acid, chenodeoxycholic acid, dehdryocholic acid, glycodeoxycholic acid, cycledextrins and the like in an amount in the range of between about 0.1 and 15 weight percent, between about 0.5 and 4 weight percent, or about 2 weight percent. An additional class of absorption enhancers reported to exhibit greater efficacy with decreased irritation is the class of alkyl maltosides, such as tetradecylmaltoside (Arnold, J J et al., 2004, J Pharm Sci 93: 2205-13; Ahsan, F et al., 2001, Pharm Res 18:1742-46) and references therein, all of which are hereby incorporated by reference.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant such as Ph. Helv or a similar alcohol.

The pharmaceutical compositions of this invention may be orally administered in any orally acceptable dosage form including, but not limited to, capsules, tablets, and aqueous suspensions and solutions. In the case of tablets for oral use, carriers that are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient that is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Formulations for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in another formulation. Suitable formulations include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topical transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

When formulated for delivery by inhalation, a number of formulations offer advantages. Adsorption of the insulin peptide to readily dispersed solids such as diketopiperazines (for example, Technosphere particles (Pfutzner, A and Forst, T, 2005, Expert Opin Drug Deliv 2:1097-1106)) or similar structures gives a formulation that results in rapid initial uptake of the insulin peptide. Lyophilized powders, especially glassy particles, containing the insulin peptide and an excipient are useful for delivery to the lung with good bioavailability, for example, see Exubera® (inhaled insulin by Pfizer).

Dosage levels of between about 0.01 and about 100 mg/kg body weight per day, preferably 0.5 and about 50 mg/kg body weight per day of the active ingredient compound are useful in the prevention and treatment of disease. Such administration can be used as a chronic or acute therapy. The amount of drug that may be combined with the carrier to produce a single dosage form will vary depending upon the host treated and the particular mode of administration. A typical preparation will contain from about 5% to about 95% active compound (w/w). Preferably, such preparations contain from about 20% to about 80% active compound.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence of disease symptoms.

As the skilled artisan will appreciate, lower or higher doses than those recited above may be required. Specific dosage and treatment regimens for any particular patient will depend upon a variety of factors, including the activity of the specific compound employed, the age, body weight, general health status, gender, diet, time of administration, rate of excretion, drug combination, the severity and course of an infection, the patient's disposition to the infection and the judgment of the treating physician.

The carrier-drug conjugates described herein provide advantages to drug manufacturers and patients over unmodified drugs. Specifically, the carrier-drug conjugate or formulation will be a more potent, longer lasting, and require smaller and less frequent dosing. This translates into lowered healthcare costs and more convenient drug administration schedules for patients. The carrier-drug conjugates can also provide subcutaneous or transdermal routes of administration as alternatives to intravenous injection. These routes can be self-administered by patients and thus improve patient compliance.

In yet another aspect of the invention, the levels of DBP can be increased as part of the carrier-drug therapy. It has been reported that estrogen can increase DBP levels (Speeckaert et al., Clinica Chimica Acta 371:33). It is contemplated here that levels of DBP can be increased by administration of estrogen for more effective delivery of carrier-drug conjugates.

In yet another aspect of the invention, it is contemplated that the carrier can be used to deliver drugs transdermally. Since DBP normally transports UV activated vitamin D at locations close to the surface of the skin, the use of a transdermal delivery system with the carrier becomes feasible.

In order that the invention described herein may be more fully understood, the following examples are set forth. It should be understood that these examples are for illustrative purposes only and are not to be construed as limiting this invention in any manner. In particular, the compositions and methods disclosed herein function with all non-hormonal forms of vitamin D, including homologs, analogs, and metabolites thereof. This includes vitamin D3 as used in the examples below.

EXAMPLES

Example 1

Preparation of Exemplary Carriers for Coupling Insulin Peptides to Non-Hormonal Vitamin D at the C25 Position Exemplary carriers were prepared containing vitamin D and 2 kDa PEG scaffolds. One exemplary carrier was thiol-reactive and comprised vitamin D-PEG with a maleimide reactive group at the C25 position. Another exemplary carrier was amine-reactive and comprised vitamin D-PEG with an NHS-reactive group. These reagents were prepared as described in WO2013172967 (Soliman et al.), incorporated herein by reference in its entirety.

Example 2

Preparation of an Exemplary Amino-Terminal Reactive Carrier for Coupling Insulin Peptides to Non-Hormonal Vitamin D at the C3 Position An exemplary amino-terminal reactive carrier was prepared containing an aldehyde reactive group connected to the C3 position of vitamin D and a 2 kDa PEG scaffold (VitD-(3)-PEG$_{2k}$-aldehyde). The aldehyde on the carrier in this example was used to conjugate to a free amino-terminus on the proteins and peptides disclosed in the examples below. The synthesis is outlined in FIG. 1.

Briefly, (S,Z)-3-((E)-2-((1R,3aS,7aR)-1-((R)-6-hydroxy-6-methylheptan-2-yl)-7a-methylhexahydro-1H-inden-4 (2H)-ylidene)ethylidene)-4-methylenecyclohexanol (compound Va, 20 mg, 0.049 mmol, 1 equiv.) purchased from Toronto Research Chemicals, catalog number C125700, also known as calcifediol and 25-hydroxyvitamin D) was dissolved in a mixture of anhydrous tert-butanol and acetonitrile (10:1, 1 mL), cooled to 4° C. Acrylonitrile (26.6 mg, 0.5 mmol, 10 equiv., was added to it followed by Triton B, 40% aqueous solution, 10 µL). The mixture was stirred at 4° C. for 2.5 h. The reaction was quenched with cold 2% HCl (10 mL), the aqueous phase was extracted with ether (2×10 mL), dried (MgSO$_4$) and evaporated to obtain the crude product. This material was purified by flash chromatography (TLC, silica gel, 50% ethyl acetate in hexanes) with 5-20% EtOAc/hexanes as eluent to isolate the desired product, 3-(((S,Z)-3-((E)-2-((1R,3aS,7aR)-1-((R)-6-hydroxy-6-methylheptan-2-yl)-7a-methylhexahydro-1H-inden-4(2H)-ylidene) ethylidene)-4-methylenecyclohexyl)oxy)propanenitrile, compound Vc (15 mg, 68%) as a white solid (R$_f$ 0.2 silica gel, 40% EtOAc in hexanes). NMR analysis did not show any appreciable amount of solvents.

To a solution of aluminum chloride (66 mg, 0.495 mmol) in anhydrous ether (2 mL) at 0° C. under argon was added a solution of lithium aluminum hydride (1M in ether, 19 mg, 0.5 mL, 0.5 mmol) dropwise. The mixture was stirred for 5 min., a solution of compound Vc (15 mg, 0.033 mmol) in ether (3 mL) was added to it dropwise, the reaction mixture was stirred at 0° C. for 5 min and then at room temperature for 1 h. The reaction was monitored by MS and TLC (silica gel, 10% MeOH/CHCl$_3$/0.1% NH$_4$OH). Ethyl acetate (1 mL) and water (1 mL) were added to the reaction mixture followed by 5% NaOH (5 mL). The organic phase was separated, and the aqueous phase was extracted with ethyl acetate (5 mL) and ether (5 mL). The combined organic phases were washed with brine (5 mL), dried (Na$_2$SO$_4$) and evaporated on a rotavap to afford the desired amine, (R)-6-((1R,3aS,7aR,E)-4-((Z)-2-((S)-5-(3-aminopropoxy)-2-methylenecyclohexylidene)ethylidene)-7a-methyloctahydro-1H-inden-1-yl)-2-methylheptan-2-ol, compound Vd (12.5 mg, 82%) as a pale yellow oil. R$_f$ 0.2 (silica gel, 20% MeOH/DCM/0.2% NH$_4$OH). The NMR analysis revealed the presence ~8% of ethyl acetate.

Compound Vd (12.5 mg, 0.0273 mmol, 1 equiv.), compound Ve (hydroxyl PEG NHS ester, MW 2000 with n≅45 where n is the number of repeating CH$_2$CH$_2$O units, Jenkem Technology USA #A-5076, 43 mg, 0.0216 mmol, 0.8 equiv.) were dissolved in anhydrous dichloromethane (0.1 mL). Triethylamine (12 mg, 16 µl, 0.11 mmol, 4 equiv.) was added and the reaction mixture was stirred for 20 h at room temperature under nitrogen. The sample was dried under a stream of nitrogen to afford the crude compound Vf, which was purified by flash chromatography using 5-10% MeOH/dichloromethane as eluent to isolate the desired product Vf as a white foam (30 mg, 38%). R$_f$ 0.4 (silica gel, 10% methanol in dichloromethane). $^1$H NMR analysis of the isolated material confirmed its identity and purity.

To a solution of compound Vf (30 mg, 0.0123 mmol, 1 equiv.), tetrapropylammonium perruthenate (1.0 mg, 0.00284, 0.23 equiv.) and N-methylmorpholine-N-Oxide (4.3 mg, 0.0369 mmol, 3 equiv.) in 2 mL of dry dichloromethane was added powdered 4 A° molecular sieves (500 mg) and the reaction mixture was flushed with N$_2$. The reaction flask was covered with aluminum foil to avoid light and it was stirred at room temperature for 36 h. Since the R$_f$ of both starting material and product is same on TLC (silicagel, 10% MeOH/dichloromethane), formation of the product was confirmed by examining the $^1$HNMR of an aliquot. The reaction mixture was filtered through the pad of Celite in a pipette with dichloromethane (15 mL) and N$_2$ pressure. The combined organics were concentrated under a flow of N$_2$ and dried on high vacuum for 2 h to get 35 mg (100%) of the crude product TLC (R$_f$: 0.3, 10% MeOH/dichloromethane, staining with PMA). A second run of reaction under the exactly same conditions yielded another 35 mg of the product. $^1$H NMR of the product from both batches is same and hence combined to get 70 mg of compound V, VitD-(3)-PEG$_{2k}$-aldehyde.

Example 3

Preparation of an Exemplary Thiol-Reactive Carrier for Coupling Insulin Peptides to Non-Hormonal Vitamin D at the C3 Position An exemplary thiol-reactive carrier comprising vitamin D with a maleimide reactive group connected to the C3 position of vitamin D (VitD-(3)-PEG$_{2k}$-maleimide) was prepared. The maleimide on the carrier in this example was used to conjugate to a free thiol on the protein and peptide in the examples below. The synthesis is outlined in FIG. 2.

Briefly, compound Vd (23 mg, 0.05 mmol, 1 equiv.) prepared as in Example 2, compound VIa (Creative Pegworks cat. # PHB-956, MAL-PEG-COOH, 2k with n≅45 where n is the number of repeating CH$_2$CH$_2$O units, 79 mg, 0.0395 mmol, 0.8 equiv.) and 2-chloro-1-methylpyridinium iodide (32 mg, 0.125 mmol, 2.5 equiv.) were dissolved in anhydrous dichloromethane (1 mL). Triethylamine (20.4 mg, 28 µl, 0.2 mmol, 4 equiv.) was added and the reaction mixture was stirred for 4 h at room temperature under nitrogen. The reaction mixture was diluted with dichloromethane (20 mL), washed with 5% aqueous citric acid (20 mL), saturated aqueous sodium bicarbonate (20 mL), and brine (20 mL). The organic layer was dried over anhydrous sodium sulfate, filtered and concentrated at 30° C. The sample was purified by silica gel (10 g) flash chromatography. The column was eluted with 1-10% MeOH/dichloromethane. Fractions containing pure product were combined together and evaporated on a rotavap, while maintaining the temperature at 30° C. The sample was dried under a stream of nitrogen to afford compound VI, VitD-(3)-PEG$_{2k}$-maleimide as a brown gum (58 mg, 48%) (R$_f$ 0.25, silica gel, 10% methanol in dichloromethane) $^1$H NMR analysis of the isolated material confirmed its identity and purity.

Example 4

Figure 3:
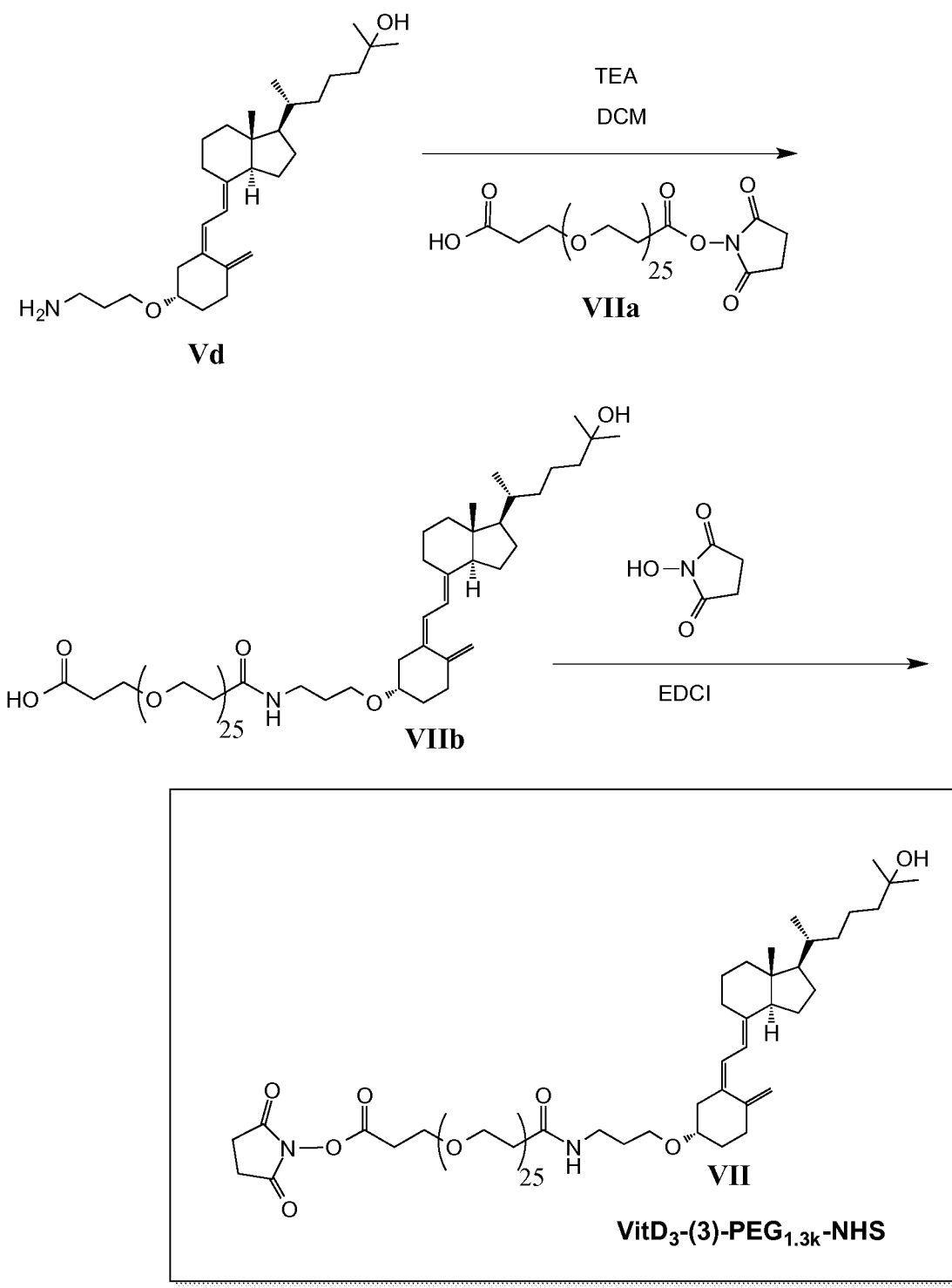
FIG. 3: Reaction scheme showing the chemical structure and syntheses used to generate a carrier, a vitamin D-(3)-PEG$_{1.3k}$-NHS adduct. The carrier was generated by conjugating 1) a vitamin D analog, 2) a PEG scaffold, and 3) an NHS coupling group.

Preparation of an Exemplary Amine-Reactive Carrier for Coupling Insulin Peptides to Non-Hormonal Vitamin D at the C3 Position An exemplary amine-reactive carrier comprising vitamin D with an NHS reactive group connected to the C3 position of vitamin D (VitD-(3)-PEG$_{1.3k}$-NHS) was prepared. The NHS on the carrier in this example was used to conjugate to a free thiol on the protein and peptide in the examples below. The synthesis is outlined in FIG. 3.

Briefly, compound Vd (20 mg, 0.044 mmol, 1 equiv.) and compound VIIa (Quanta Biodesign cat. #10140, with n=25 where n is the number of repeating CH$_2$CH$_2$O units, 44 mg, 0.0346 mmol, 0.8 equiv.) were dissolved in anhydrous dichloromethane (1 mL). Triethylamine (22.0 mg, 31 µl, 0.22 mmol, 5 equiv.) was added and the reaction mixture was stirred for 24 h at room temperature under nitrogen. The reaction mixture was diluted with dichloromethane (20 mL), washed with 5% aqueous citric acid (20 mL), and brine (20 mL). The organic layer was dried over anhydrous sodium sulfate, filtered and concentrated while maintaining the temperature at 30° C. The sample was purified by silica gel (10 g) flash chromatography. The column was eluted with 1-10% MeOH/dichloromethane. Fractions containing pure product were combined together and evaporated on a rotavap, while maintaining the temperature below 30° C. The sample was dried under a stream of nitrogen to afford compound VIIb as a brown gum (33 mg, 56%) (R$_f$ 0.20, silica gel, 10% methanol in dichloromethane). $^1$H NMR analysis of the isolated material confirmed its identity.

Compound VIIb (31 mg, 0.018 mmol, 1 equiv.), N-hydroxysuccinimide (6.3 mg, 0.055 mmol, 3 equiv.), and EDCI (8.6 mg, 0.045 mmol, 2.5 eq.) were dissolved in anhydrous THF (2 mL). Triethylamine (7.4 mg, 10 µL, 0.073 mmol, 4 equiv.) was added and the reaction mixture was stirred for 24 h at room temperature under nitrogen. The reaction mixture was diluted with dichloromethane (20 mL) and washed with 5% aqueous citric acid (20 mL), and brine (20 mL). The organic layer was dried over anhydrous sodium sulfate, filtered and concentrated while maintaining the temperature at 30° C. The sample was dried under a stream of nitrogen to afford compound VII, VitD-(3)-PEG$_{1.3k}$-NHS, as a brown gum (38.6 mg, >100%) (R$_f$ 0.25, silica gel, 10% methanol in dichloromethane). $^1$H NMR analysis of the isolated material confirmed its identity and purity.

Example 5

Preparation of Insulin Coupled to Non-Hormonal Vitamin D at the C25 and C3 Positions In this example, the VitD-(25)-PEG$_{2k}$-NHS was conjugated to human insulin comprising the A chain (SEQ ID NO:1) and B chain (SEQ ID NO:2) to prepare a therapeutic for treating diabetes. The insulin A chain contains a cys6-cys11 intra-chain disulfide linkage. The cys7 on the A chain is linked to cys7 of the B chain by an inter-chain disulfide linkage. The cys20 on the A chain is linked to cys19 of the B chain, also by an inter-chain disulfide linkage. The NHS reactive group targets the carrier to amino reactive side chains on residues such as lysine when reacted as described below. Thus, this reaction in this example targeted lysine 29 on the insulin B-chain. Insulin (Sigma Aldrich, St. Louis, Mo., Catalog #I2643) was resuspended in a 1:1 mixture of DMSO and 1M HEPES+0.85% NaCl, pH=8 at a concentration of 5 mg/ml. VitD-(25)-PEG$_{2k}$-NHS carrier dissolved in DMSO at a concentration of 5 mg/ml 1.4 to 4 molar equivalents relative to insulin was added. The final concentration of insulin was brought to 1 mg/ml in dH$_2$O and the reaction was allowed to proceed for 1 hour at room temperature. The insulin conjugates were confirmed by SDS-PAGE.

In this example, the VitD-(3)-PEG$_{1.3k}$-NHS is conjugated to human insulin to prepare a therapeutic for treating diabetes. Insulin (Sigma Aldrich, St. Louis, Mo., Catalog #I2643) is resuspended in a 1:1 mixture of DMSO and 1M HEPES+0.85% NaCl, pH=8 at a concentration of 5 mg/ml. VitD-(2)-PEG$_{1.3k}$-NHS carrier is dissolved in DMSO at a concentration of 5 mg/ml 1.4 to 4 molar equivalents relative to insulin was added. The final concentration of insulin is brought to 1 mg/ml in dH$_2$O and the reaction is allowed to proceed for 1 hour at room temperature. The insulin conjugates are confirmed by SDS-PAGE.

Pharmacokinetic experiments, in vitro bioactivity assays measuring the uptake of glucose by adipocytes, and evaluation in vivo of the blood glucose lowering ability in diabetic rat models are performed as described in EP2085406, incorporated herein by reference in its entirety.

Example 6

Preparation of Insulin Coupled to Non-Hormonal Vitamin D at the C25 and C3 Positions Synthesis of VitD-(25)-PEG$_{2K}$-insulin In this example, the VitD-(25)-PEG$_{2K}$-NHS from Example 1 was conjugated to human insulin comprising the A chain (SEQ ID NO:1) and B chain (SEQ ID NO:2) to prepare a therapeutic for treating diabetes. A 2 KDa PEG scaffold was conjugated to the carbon 25 atom on the vitamin D molecule. This carrier was conjugated to lysine 29 on the insulin B-chain. Insulin (Sigma Aldrich, St. Louis, Mo., Catalog #I2643) was resuspended in a 95:5 mixture of DMSO and triethylamine (TEA) at a concentration of 10 mg/ml. VitD-(25)-PEG$_{2K}$-NHS carrier was dissolved in a 95:5 mixture of DMSO and TEA at a concentration of 10 mg/ml. 1.3-1.6 molar equivalents of the VitD-(25)-PEG$_{2K}$-NHS carrier was added to 1.0 molar equivalents of insulin and the reaction was allowed to proceed at room temperature for 2-16 hours in the dark. Two volumes of deionized water were added to the reaction mixture, and the pH was adjusted to between 8 and 9 by the addition of 2N HCl. SDS-PAGE analysis showed that insulin conjugated to one VitD-(25)-PEG$_{2K}$ carrier was the major product but unmodified insulin and insulin conjugated to two carriers were also present. The desired insulin conjugate with one carrier was purified by anion exchange chromatography (HiTrap Q HP column, GE Healthcare) in buffer A (20 mM Tris pH=8.5, 50% ethanol) with a 20 minute gradient to 60% buffer B (20 mM Tris pH=8.5, 1 M NaCl, 50% ethanol). The insulin conjugate was confirmed by SDS-PAGE and MALDI-TOF mass spectrometry.

Synthesis of VitD-(3)-PEG$_{1.2K}$-Insulin

In this example, the VitD-(3)-PEG$_{1.3K}$-NHS (VII) from Example 4 was conjugated to human insulin at lysine 29 on the B-chain to prepare a therapeutic for treating diabetes. As a result of the conjugation reaction, the scaffold was a 1.2 kDa PEG It was attached to vitamin D on the 3 position. The reaction was performed in a similar manner as described above for the VitD-(25)-PEG$_{2K}$-NHS carrier. The desired insulin conjugate with one VitD-(3)-PEG$_{1.2K}$-carrier was purified by anion exchange chromatography (HiTrap Q HP column, GE Healthcare) in buffer A (20 mM Tris pH=8.5, 50% methanol) with a 20 minute gradient to 30% buffer B (20 mM Tris pH=8.5, 1 M NaCl, 50% methanol). The insulin conjugate was confirmed by SDS-PAGE analysis.

Synthesis of 20K-PEG-Insulin

In this example, 20 kD PEG-NHS was conjugated to human insulin to prepare a benchmark therapeutic for treating diabetes (see EP2288375). The reaction was performed in a similar fashion as described above, except 0.7 molar equivalents of methoxy PEG succinimidyl carboxymethyl ester, MW 20000 (Jenkem Cat. No. M-SCM-20K) dissolved in 95:5 acetonitrile: TEA at a concentration of 100 mg/ml was reacted with 1.0 molar equivalent of insulin dissolved in 95:5 DMSO:TEA at a concentration of 10 mg/ml. The desired insulin conjugate with one 20 kD PEG conjugate was purified by anion exchange chromatography (HiTrap Q HP column, GE Healthcare) in buffer A (20 mM Tris pH=8.5) with a 15 minute gradient to 100% buffer B (20 mM Tris pH=8.5, 1 M NaCl). The insulin conjugate was confirmed by SDS-PAGE analysis.

Activity of Insulin Constructs in Cell-Based INSRb Receptor Assay:

Unmodified insulin, 20K-PEG-insulin, VitD-(25)-PEG$_{2K}$-insulin, and VitD-(3)-PEG$_{1.2K}$-insulin were analyzed using the PathHunter® U2OS INSRb Functional Assay (Discover RX, Inc., Freemont, Calif., Cat. No. 93-0466C3). U-2 OS cells expressing the insulin receptor, isoform B, measures the activation of this receptor by recruiting an SH2 fusion protein that is dependent on receptor phosphorylation. This leads to complementation of two fragments of the beta-galactosidase enzyme. FIG. 4 compares the functional activity of insulin vs. the three modified peptides. The curves were fit with a four parameter logistic function in order to determine the EC$_{50}$ values (Table 1). The results show that all the compounds have activity against the insulin receptor INSRb in this assay.

TABLE 1

| Compound | EC$_{50}$ |
|---|---|
| Insulin | 7.9 ng/ml |
| 20K-PEG-insulin | 26.3 ng/ml |
| VitD-(25)-PEG$_{2K}$-insulin | 15.8 ng/ml |
| VitD-(3)-PEG$_{1.2K}$-insulin | 282.2 ng/ml |

It was observed that the smaller PEG size in VitD-(3)-PEG$_{1.2K}$-insulin resulted in a lower solubility in solution and the cell-based assay than the insulin conjugates with 2 kDa or 20 kDa PEG This molecule, however, showed a higher solubility in serum that likely resulted from DBP binding. For example, when VitD-(3)-PEG$_{1.2K}$-insulin was diluted in PBS buffer, quantitation by ELISA yielded a four-fold lower value than when a similar dilution was performed in either serum or a Tween 20-containing buffer. As discussed below, this conjugate showed the best pharmacokinetic profile and glucose reduction in vivo.

Figure 5B:
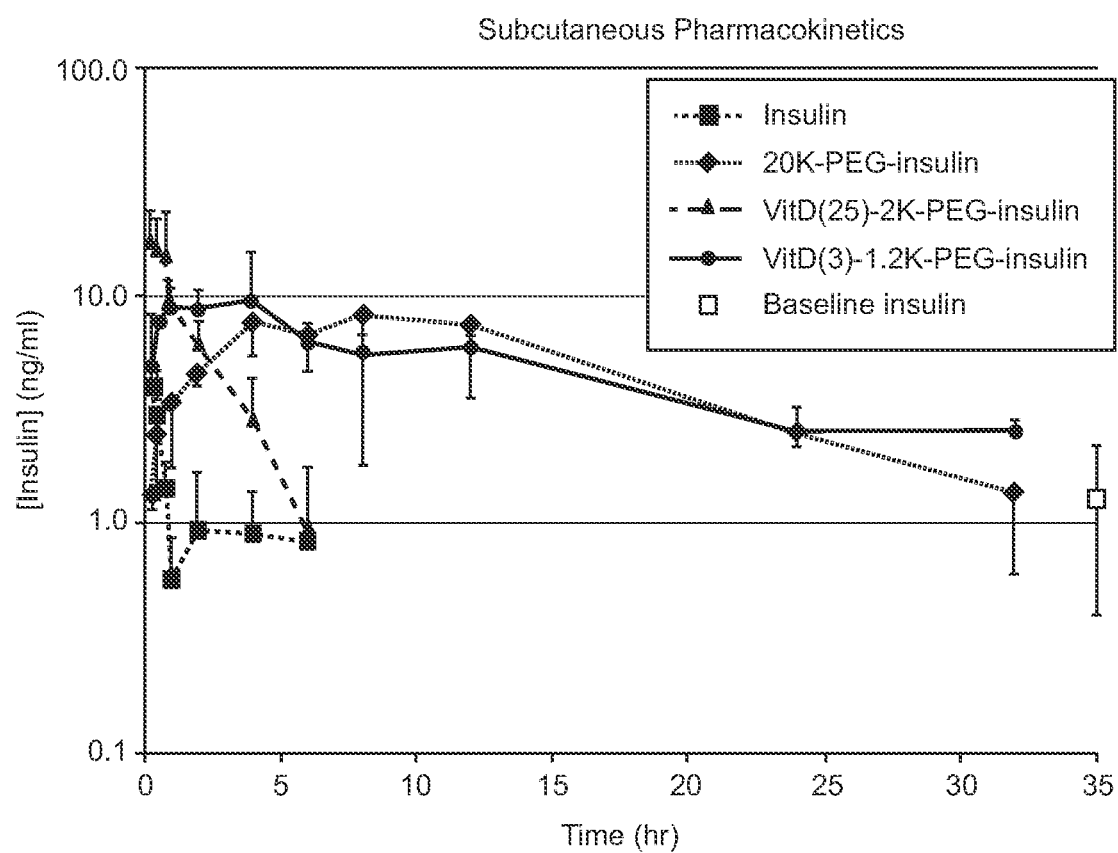

Pharmacokinetic and Pharmacodynamics Properties of Insulin and Insulin Conjugates:

Groups of three rats each were injected either intravenously or subcutaneously with insulin, VitD-(25)-PEG$_{2K}$-insulin, 20K-PEG-insulin, or VitD-(3)-PEG$_{1.2K}$-insulin at a dose of 0.02 mg/kg (0.58 IU/kg) (iv) or 0.04 mg/kg (1.15 IU/kg) (sc). Plasma samples were taken at 5 minutes (iv only), 0.5, 1, 2, 4, 6, 8, 24, 32, 48, and 56 hours and analyzed for the quantity of insulin and glucose. Insulin was measured by the SPI-BIO Insulin (mouse/rat) EIA kit (Cayman Chemicals, Ann Arbor, Mich. Cat. No. 589501). All of the modified insulin derivatives had improved pharmacokinetic profiles when compared to native insulin (FIGS. 5A and 5B). Unmodified insulin decayed to near-background levels within 15-30 minutes of iv injection and 45-60 minutes of sc injection. The 20K-PEG-insulin and VitD-(25)-PEG$_{2K}$-insulin improved the in vivo half life. The VitD-(3)-PEG$_{1.2K}$-insulin, however, showed the most dramatic pharmacokinetic properties. This demonstrates that conjugation of the carrier to the C3 position of vitamin D is preferred to conjugation at the C25 position. Also, VitD-(3)-PEG$_{1.2K}$-insulin was superior to 20K-PEG-insulin. This demonstrated that the vitamin D moiety provides a significant benefit in extending the half-life of insulin.

Figure 6:
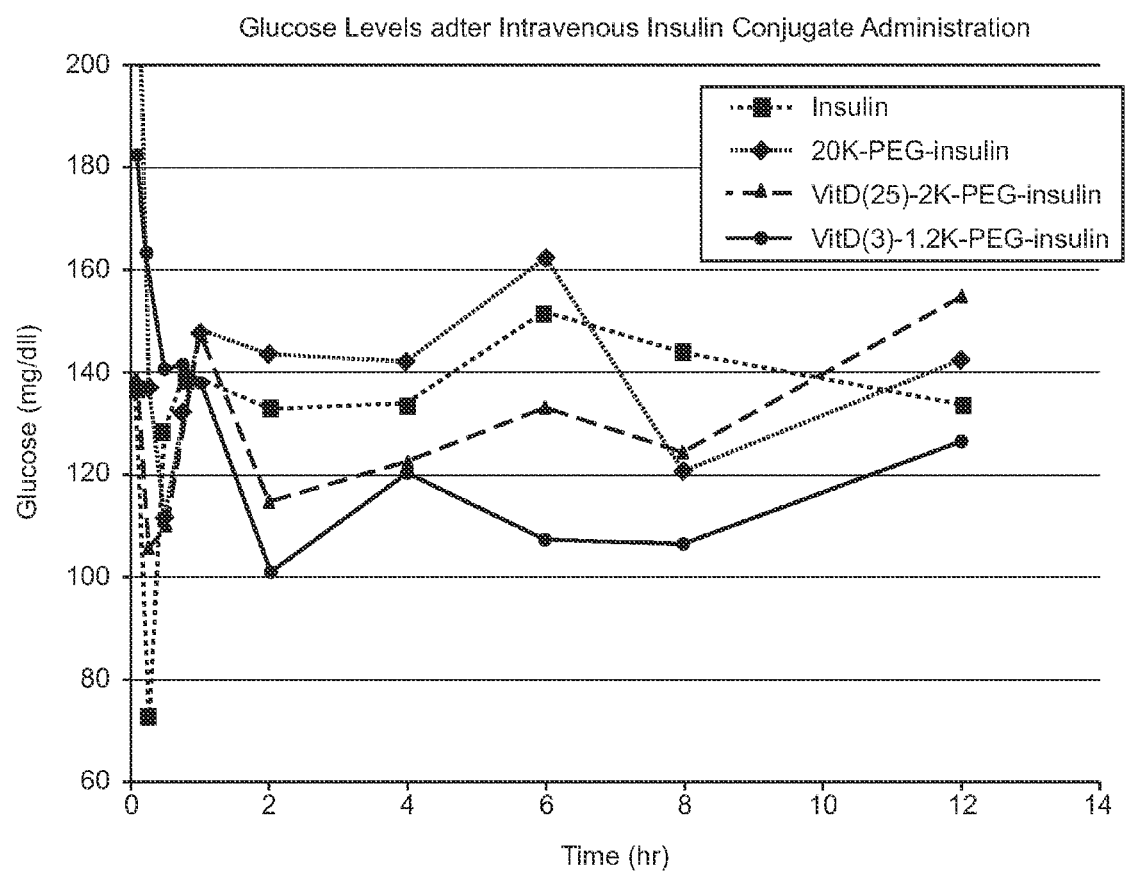
FIG. 6: Blood glucose lowering pharmacodynamics of insulin conjugates compared to native insulin upon intravenous administration at time=0 hr.

VitD-(3)-PEG$_{1.2K}$-insulin was highly effective at stably reducing blood glucose levels in vivo. Blood glucose levels were determined in rats injected with free glucose and the conjugates using the Amplex Red Glucose/Glucose Oxidase Assay Kit (Invitrogen, Carlsbad, Calif., Cat. No. A22189). FIG. 6 shows that free insulin caused a sharp drop in glucose levels lasting 30 minutes. In contrast, VitD-(3)-PEG$_{1.2K}$-insulin and VitD-(25)-PEG$_{2K}$-insulin stably reduced blood glucose levels for approximately eight hours. VitD-(3)-PEG$_{1.2K}$-insulin caused a larger and more sustained drop in glucose levels than VitD-(25)-PEG$_{2K}$-insulin. The PEG20K-insulin conjugate did not display significant glucose lowering ability for an extended time.

EXEMPLARY SEQUENCES (human insulin A Chain)
SEQ ID NO: 1
GIVEQCCTSICSLYQLENYCN SEQ ID NO: 2: (human insulin B Chain)
FVNQHLCGSHLVEALYLVCGERGFFYTPKT (Vitamin D Binding Protein (DBP))
SEQ ID NO: 3
MKRVLVLLLAVAFGHALERGRDYEKNKVCKEFSHLGKEDFTSLSLVLYSR

KFPSGTFEQVSQFVKEVVSFTEACCAEGADPDCYDTRTSAFSAKSCESNS

PFPVHPGTAECCTKEGFERKLCMAALKHQPQEFPTYVEPTNDEICEAFRK

DPKEYANQFMWEYSTNYGQAPLSLLVSYTKSYLSMVGSCCTSASPTVCFL

KERLQLKHLSLLTTLSNRVCSQYAAYGEKKSRLSNLIKLAQKVPTADLED

VLPLAEDITNILSKCCESASEDCMAKELPEHTVKLCDNLSTKNSKFEDCC

QEKTAMDVFVCTYFMPAAQLPELPDVELPTNKDVCDPGNTKVMDKYTFEL

SRRTHLPEVFLSKVLEPTLKSLGECCDVEDSTTCFNAKGPLLKKELSSFI

DKGQELCADYSENTFTEYKKKLAERLKAKLPDATPTELAKLVNKHSDFAS

NCCSINSPPLYCDSEIDAELKNIL (Vitamin D Binding Protein (DBP))
SEQ ID NO: 4
TTTAATAATAATTCTGTGTTGCTTCTGAGATTAATAATTGATTAATTCAT

AGTCAGGAATCTTTGTAAAAAGGAAACCAATTACTTTTGGCTACCACTTT

TACATGGTCACCTACAGGAGAGAGGAGGTGCTGCAAGACTCTCTGGTAGA

AAAATGAAGAGGGTCCTGGTACTACTGCTTGCTGTGGCATTTGGACATGC

TTTAGAGAGAGGCCGGGATTATGAAAAGAATAAAGTCTGCAAGGAATTCT

CCCATCTGGGAAAGGAGGACTTCACATCTCTGTCACTAGTCCTGTACAGT

AGAAAATTTCCCAGTGGCACGTTTGAACAGGTCAGCCAACTTGTGAAGGA

AGTTGTCTCCTTGACCGAAGCCTGCTGTGCGGAAGGGGCTGACCCTGACT

GCTATGACACCAGGACCTCAGCACTGTCTGCCAAGTCCTGTGAAAGTAAT

TCTCCATTCCCCGTTCACCCAGGCACTGCTGAGTGCTGCACCAAAGAGGG

CCTGGAACGAAAGCTCTGCATGGCTGCTCTGAAACACCAGCCACAGGAAT

TCCCTACCTACGTGGAACCCACAAATGATGAAATCTGTGAGGCGTTCAGG

AAAGATCCAAAGGAATATGCTAATCAATTTATGTGGGAATATTCCACTAA

TTACGGACAAGCTCCTCTGTCACTTTTAGTCAGTTACACCAAGAGTTATC

TTTCTATGGTAGGGTCCTGCTGTACCTCTGCAAGCCCAACTGTATGCTTT

TTGAAAGAGAGACTCCAGCTTAAACATTTATCACTTCTCACCACTCTGTC

AAATAGAGTCTGCTCACAATATGCTGCTTATGGGGAGAAGAAATCAAGGC

TCAGCAATCTCATAAAGTTAGCCCAAAAAGTGCCTACTGCTGATCTGGAG

GATGTTTTGCCACTAGCTGAAGATATTACTAACATCCTCTCCAAATGCTG

TGAGTCTGCCTCTGAAGATTGCATGGCCAAAGAGCTGCCTGAACACACAG

TAAAACTCTGTGACAATTTATCCACAAAGAATTCTAAGTTTGAAGACTGT

TGTCAAGAAAAACAGCCATGGACGTTTTGTGTGCACTTACTTCATGCC

AGCTGCCCAACTCCCCGAGCTTCCAGATGTAGAGTTGCCCACAAACAAAG

ATGTGTGTGATCCAGGAAACACCAAAGTCATGGATAAGTATACATTTGAA

CTAAGCAGAAGGACTCATCTTCCGGAAGTATTCCTCAGTAAGGTACTTGA

GCCAACCCTAAAAAGCCTTGGTGAATGCTGTGATGTTGAAGACTCAACTA

CCTGTTTTAATGCTAAGGGCCCTCTACTAAAGAAGGAACTATCTTCTTTC

ATTGACAAGGGACAAGAACTATGTGCAGATTATTCAGAAAATACATTTAC

```
TGAGTACAAGAAAAAACTGGCAGAGCGACTAAAAGCAAAATTGCCTGATG

CCACACCCACGGAACTGGCAAAGCTGGTTAACAAGCACTCAGACTTTGCC

TCCAACTGCTGTTCCATAAACTCACCTCCTCTTTACTGTGATTCAGAGAT

TGATGCTGAATTGAAGAATATCCTGTAGTCCTGAAGCATGTTTATTAACT

TTGACCAGAGTTGGAGCCACCCAGGGGAATGATCTCTGATGACCTAACCT

AAGCAAAACCACTGAGCTTCTGGGAAGACAACTAGGATACTTTCTACTTT

TTCTAGCTACAATATCTTCATACAATGACAAGTATGATGATTTGCTATCA

AAATAAATTGAAATATAATGCAAACCATAAAAAAAAAAAAAAAAAAAAA
A (Insulin analog A chain sequence 3)
                                        SEQ ID NO: 5
GIVEQCCTSICSLYQLENYCG
```

```
(Insulin analog B chain sequence 1)
                                        SEQ ID NO: 6
FVNQHLCGSHLVEALYLVCGERGFFYTKPT (Insulin analog B chain sequence 2)
                                        SEQ ID NO: 7
FVNQHLCGSHLVEALYLVCGERGFFYTPDT (Insulin analog B chain sequence 3)
                                        SEQ ID NO: 8
FVNQHLCGSHLVEALYLVCGERGFFYTPKTKK
```

All publications and patent documents disclosed or referred to herein are incorporated by reference in their entirety. The foregoing description has been presented only for purposes of illustration and description. This description is not intended to limit the invention to the precise form disclosed. It is intended that the scope of the invention be defined by the claims appended hereto.

What is claimed:

1. A carrier-drug conjugate, comprising a targeting group that is a non-hormonal vitamin D not hydroxylated at the carbon 1 position, conjugated to an insulin peptide at the carbon 3 position of said non-hormonal vitamin D targeting group.

2. The carrier-drug conjugate of claim 1, wherein said targeting group is conjugated to said insulin peptide via a scaffold that is poly(ethylene glycol).

3. A pharmaceutical composition, comprising a carrier-drug conjugate comprising a targeting group that is a non-hormonal vitamin D not hydroxylated at the carbon 1 position, conjugated via a scaffold at the carbon 3 position to an insulin comprising a first peptide having an amino acid sequence with at least a 90% sequence identity to SEQ ID NO:1 and a second peptide having an amino acid sequence with at least a 90% sequence identity to SEQ ID NO: 2.

4. The pharmaceutical composition of claim 3, wherein said first peptide has the amino acid sequence of SEQ ID NO:1.

5. The pharmaceutical composition of claim 3, wherein said first peptide has the amino acid sequence of SEQ ID NO:5.

6. The pharmaceutical composition of claim 3, wherein said second peptide has the amino acid sequence of SEQ ID NO:2.

7. The pharmaceutical composition of claim 3, wherein said second peptide has the amino acid sequence of SEQ ID NO:6.

8. The pharmaceutical composition of claim 3, wherein said second peptide has the amino acid sequence of SEQ ID NO:7.

9. The pharmaceutical composition of claim 3, wherein said second peptide has the amino acid sequence of SEQ ID NO:8.

10. The pharmaceutical composition of claim 3, wherein said scaffold is poly(ethylene glycol).

11. A pharmaceutical composition, comprising:
  a) an insulin peptide,
  b) a stably attached scaffold, c) a targeting group that is a non-hormonal vitamin D not hydroxylated at the carbon 1 position, conjugated at the carbon 3 position, wherein after administration to a first test subject, said insulin peptide has a half-life measured by an enzyme immunoassay (EIA) of blood samples taken at a plurality of time points that is greater than a half-life of said insulin peptide administered to a second test subject without said stably attached scaffold moiety and targeting group as measured by said EIA of blood samples taken at said plurality of time points.

12. The pharmaceutical composition of claim 11, wherein said administration to said first and second subjects is accomplished by subcutaneous injection.

13. The pharmaceutical composition of claim 11, wherein said insulin peptide stably attached to said scaffold and targeting group retains about the same activity as said insulin peptide not stably attached to said scaffold and targeting group as measured by a functional assay.

14. The pharmaceutical composition of claim 11, wherein the scaffold has a mass of about 500 Da to 5,000 Da.

15. The pharmaceutical composition of claim 11, wherein said scaffold is approximately the same mass as the insulin peptide.

16. A carrier-drug conjugate, comprising a targeting group that is vitamin D that is not hydroxylate at the carbon 1 position non-releasably conjugated to a first insulin peptide, wherein said insulin peptide is conjugated at the carbon 3 position of said vitamin D targeting group.

17. The carrier-drug conjugate of claim 16, wherein said vitamin D is non-hormonal.

18. The carrier-drug conjugate of claim 16, wherein said insulin peptide retains about the same activity as said insulin peptide not conjugated to said targeting group as measured by a functional assay.

19. The carrier-drug conjugate of claim 16, further comprising a scaffold that is poly(ethylene glycol).

20. The carrier-drug conjugate of claim 19, wherein said scaffold is approximately the same mass as the insulin peptide.

21. The carrier-drug conjugate of claim 16, wherein said first insulin peptide has a 90% sequence identity to SEQ ID NO:1.

22. The carrier-drug conjugate of claim 21, further comprising a second insulin peptide having a 90% sequence identity to SEQ ID NO:2.

* * * * *